(12) United States Patent
Velasquez et al.

(10) Patent No.: US 9,849,447 B2
(45) Date of Patent: Dec. 26, 2017

(54) CATALYSTS FOR THE DEHYDRATION OF HYDROXYPROPIONIC ACID AND ITS DERIVATIVES

(71) Applicant: The Procter & Gamble Company, Cincinnati, OH (US)

(72) Inventors: Juan Esteban Velasquez, Cincinnati, OH (US); Dimitris Ioannis Collias, Mason, OH (US); Jane Ellen Godlewski, Loveland, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 15/249,712

(22) Filed: Aug. 29, 2016

(65) Prior Publication Data

US 2017/0056863 A1    Mar. 2, 2017

Related U.S. Application Data

(60) Provisional application No. 62/211,008, filed on Aug. 28, 2015.

(51) Int. Cl.
| | |
|---|---|
| *B01J 27/195* | (2006.01) |
| *B01J 27/18* | (2006.01) |
| *B01J 27/16* | (2006.01) |
| *B01J 37/04* | (2006.01) |
| *B01J 37/08* | (2006.01) |
| *B01J 23/20* | (2006.01) |
| *B01J 35/02* | (2006.01) |
| *B01J 37/00* | (2006.01) |
| *C07C 51/00* | (2006.01) |

(52) U.S. Cl.
CPC ............. *B01J 27/195* (2013.01); *B01J 23/20* (2013.01); *B01J 27/16* (2013.01); *B01J 27/1806* (2013.01); *B01J 35/023* (2013.01); *B01J 37/0036* (2013.01); *B01J 37/04* (2013.01); *B01J 37/08* (2013.01); *C07C 51/00* (2013.01)

(58) Field of Classification Search
CPC ........ B01J 27/16; B01J 27/18; B01J 27/1806; B01J 27/1811; B01J 27/1813; B01J 27/186; B01J 27/187; B01J 27/188; B01J 27/195; B01J 35/023; B01J 37/0036; B01J 37/04; B01J 37/08
USPC ................................ 502/208–214
See application file for complete search history.

(56) References Cited

U.S. PATENT DOCUMENTS

| | | | | |
|---|---|---|---|---|
| 3,781,222 | A * | 12/1973 | Weisang et al. | B01J 27/1806 502/208 |
| 4,695,661 | A * | 9/1987 | Homann | B01J 27/1806 502/208 |
| 4,729,978 | A * | 3/1988 | Sawicki | B01J 27/1806 502/174 |
| 7,683,220 | B2 * | 3/2010 | Matsunami | B01J 27/16 568/485 |

(Continued)

OTHER PUBLICATIONS

International Search Report and Written Opinion dated Dec. 6, 2016.

*Primary Examiner* — Patricia L Hailey
(74) *Attorney, Agent, or Firm* — Brent M. Peebles

(57) ABSTRACT

Hydroxypropionic acid, hydroxypropionic acid derivatives, or mixtures thereof are dehydrated using a catalyst and a method to produce bio-acrylic acid, acrylic acid derivatives, or mixtures thereof. A method to produce the dehydration catalyst is also provided.

12 Claims, 1 Drawing Sheet

(56) References Cited

U.S. PATENT DOCUMENTS

| | | |
|---|---|---|
| 2013/0274515 A1 | 10/2013 | Godlewski et al. |
| 2013/0274516 A1* | 10/2013 | Velasquez ............ B01J 27/1806 |
| | | 562/599 |
| 2013/0274517 A1* | 10/2013 | Godlewski ............ C07C 51/377 |
| | | 562/599 |
| 2013/0274520 A1 | 10/2013 | Godlewski et al. |
| 2015/0105584 A1 | 4/2015 | Velasquez et al. |
| 2017/0057900 A1* | 3/2017 | Velasquez ............ B01J 27/1806 |
| 2017/0057901 A1* | 3/2017 | Velasquez ............ B01J 27/1806 |

\* cited by examiner

CATALYSTS FOR THE DEHYDRATION OF HYDROXYPROPIONIC ACID AND ITS DERIVATIVES

FIELD OF THE INVENTION

The present invention generally relates to dehydration catalysts useful for the conversion of hydroxypropionic acid, hydroxypropionic acid derivatives, or mixtures thereof to acrylic acid, acrylic acid derivatives, or mixtures thereof. The invention also relates to methods of making such dehydration catalysts.

BACKGROUND OF THE INVENTION

Acrylic acid, acrylic acid derivatives, or mixtures thereof have a variety of industrial uses, typically consumed in the form of polymers. In turn, these polymers are commonly used in the manufacture of, among other things, adhesives, binders, coatings, paints, polishes, detergents, flocculants, dispersants, thixotropic agents, sequestrants, and superabsorbent polymers (SAP), which are used in disposable absorbent articles, comprising diapers and hygienic products, for example. Acrylic acid is commonly made from petroleum sources. For example, acrylic acid has long been prepared by catalytic oxidation of propylene. These and other methods of making acrylic acid from petroleum sources are described in the Kirk-Othmer Encyclopedia of Chemical Technology, Vol. 1, pgs. 342-369 (5$^{th}$ Ed., John Wiley & Sons, Inc., 2004). As petrochemical resources become increasingly scarce, more expensive, and subject to regulations for $CO_2$ emissions, there exists a growing need for bio-based acrylic acid, acrylic acid derivatives, or mixtures thereof that can serve as an alternative to petroleum-based acrylic acid, acrylic acid derivatives, or mixtures thereof.

Many attempts have been made over the last 80 years to make bio-based acrylic acid, acrylic acid derivatives, or mixtures thereof from non-petroleum sources, such as lactic acid (also known as 2-hydroxypropionic acid), lactic acid derivatives (e.g. alkyl 2-acetoxy-propionate and 2-acetoxy propionic acid), 3-hydroxypropionic acid, glycerin, carbon monoxide and ethylene oxide, carbon dioxide and ethylene, and crotonic acid. From these non-petroleum sources, only lactic acid is produced today in high yield from sugar (≥90% of theoretical yield, or equivalently, ≥0.9 g of lactic acid per g of sugar). Furthermore, commercial lactic acid purity and economics could favor producing acrylic acid at a cost competitive to petroleum-based acrylic acid. As such, lactic acid or lactate presents a real opportunity of serving as a feedstock for bio-based acrylic acid, acrylic acid derivatives, or mixtures thereof. Also, 3-hydroxypropionic acid is expected to be produced at commercial scale in a few years, and as such, 3-hydropropionic acid will present another real opportunity of serving as feedstock for bio-based acrylic acid, acrylic acid derivatives, or mixtures thereof. Sulfate salts, phosphate salts, mixtures of sulfate and phosphate salts, bases, zeolites or modified zeolites, metal oxides or modified metal oxides, and supercritical water are the main catalysts which have been used to dehydrate lactic acid or lactate to acrylic acid, acrylic acid derivatives, or mixtures thereof in the past with varying success.

For example, U.S. Pat. No. 4,786,756 (issued in 1988), describes the vapor phase dehydration of lactic acid or ammonium lactate to acrylic acid using aluminum phosphate ($AlPO_4$) treated with an aqueous inorganic base as a catalyst. As an example, the '756 patent discloses a maximum yield of acrylic acid of 43.3% when lactic acid was fed into the reactor at approximately atmospheric pressure, and a respective yield of 61.1% when ammonium lactate was fed into the reactor. In both examples, acetaldehyde was produced at yields of 34.7% and 11.9%, respectively, and other side products were also present in large quantities, such as propionic acid, CO, and $CO_2$. Omission of the base treatment caused increased amounts of the side products. Another example is Hong et al., Appl. Catal. A: General 396:194-200 (2011), who developed and tested composite catalysts made with $Ca_3(PO_4)_2$ and $Ca_2(P_2O_7)$ salts with a slurry-mixing method. The catalyst with the highest yield of acrylic acid from methyl lactate was the 50%-50% (by weight) catalyst. It yielded 68% acrylic acid, about 5% methyl acrylate, and about 14% acetaldehyde at 390° C. The same catalyst achieved 54% yield of acrylic acid, 14% yield of acetaldehyde, and 14% yield of propionic acid from lactic acid.

Prof. D. Miller's group at Michigan State University (MSU) published many papers on the dehydration of lactic acid or lactic acid esters to acrylic acid and 2,3-pentanedione, such as Gunter et al., J. Catalysis 148:252-260 (1994); and Tam et al., Ind. Eng. Chem. Res. 38:3873-3877 (1999). The best acrylic acid yields reported by the group were about 33% when lactic acid was dehydrated at 350° C. over low surface area and pore volume silica impregnated with NaOH. In the same experiment, the acetaldehyde yield was 14.7% and the propionic acid yield was 4.1%. Examples of other catalysts tested by the group were $Na_2SO_4$, NaCl, $Na_3PO_4$, $NaNO_3$, $Na_2SiO_3$, $Na_4P_2O_7$, $NaH_2PO_4$, $Na_2HPO_4$, $Na_2HAsO_4$, $NaC_3H_5O_3$, NaOH, CsCl, $Cs_2SO_4$, KOH, CsOH, and LiOH. In all cases, the above referenced catalysts were tested in gas phase reactions with low partial pressures of water, as commonly suggested in the art for dehydration reactions. Finally, the group suggested that the acrylic acid yield is increased (and the by-product yields are decreased) when the surface area of the silica support is low, the reaction temperature is high, the reaction pressure is low, and the residence time of the reactants in the catalyst bed is short.

Finally, the Chinese patent application 200910054519.7 discloses the use of ZSM-5 molecular sieves modified with aqueous alkali (such as $NH_3$, NaOH, and $Na_2CO_3$) or a phosphoric acid salt (such as $NaH_2PO_4$, $Na_2HPO_4$, $LiH_2PO_4$, $LaPO_4$, etc.). The best yield of acrylic acid achieved in the dehydration of lactic acid was 83.9%, however that yield came at very long residence times.

Therefore, the manufacture of acrylic acid, acrylic acid derivatives, or mixtures thereof from lactic acid or lactate by processes, such as those described in the literature noted above, has demonstrated: 1) yields of acrylic acid, acrylic acid derivatives, or mixtures thereof not exceeding 70% at short residence times; 2) low selectivities of acrylic acid, acrylic acid derivatives, or mixtures thereof, i.e., significant amounts of undesired side products, such as acetaldehyde, 2,3-pentanedione, propionic acid, CO, and $CO_2$; 3) long residence times in the catalyst beds; and 4) catalyst deactivation in short time on stream (TOS). The side products can deposit onto the catalyst resulting in fouling, and premature and rapid deactivation of the catalyst. Further, once deposited, these side products can catalyze other undesired reactions. Aside from depositing on the catalysts, these side products, even when present in only small amounts, impose additional costs in processing acrylic acid (when present in the reaction product effluent) towards the manufacture of SAP, for example. These deficiencies of the prior art processes and catalysts render them commercially non-viable.

Accordingly, there is a need for catalysts, methods of making the catalysts, and processes for the dehydration of hydroxypropionic acid, hydroxypropionic acid derivatives, or mixtures thereof to acrylic acid, acrylic acid derivatives, or mixtures thereof, with high yield and selectivity toward acrylic acid, in an efficient manner (i.e. short residence times), and with suitable catalyst longevity.

SUMMARY OF THE INVENTION

In one embodiment of the present invention, a dehydration catalyst is provided. The dehydration catalyst comprises: (a) one or more amorphous phosphate salts consisting essentially of: i) one or more monovalent cations, and ii) one or more phosphate anions selected from the group represented by empirical formula (I):

$$[H_{2(1-x)}PO_{(4-x)}]^{-} \qquad (I);$$

wherein x is any real number equal to or greater than 0 and equal to or less than 1; and wherein said one or more amorphous phosphate salts of said dehydration catalyst are neutrally charged; and (b) one or more non-phosphate compounds; and wherein said one or more non-phosphate compounds are substantially chemically inert to said one or more amorphous phosphate salts.

In one embodiment of the present invention, a dehydration catalyst is provided. The dehydration catalyst comprises: (a) one or more amorphous phosphate salts represented by empirical formula $KH_{2(1-x)}PO_{(4-x)}$, wherein x is any real number equal to or greater than 0 and equal to or less than 1; and (b) amorphous silica.

In another embodiment of the present invention, a method of preparing a dehydration catalyst is provided. The method comprises contacting:

(a) a dehydration catalyst precursor mixture comprising one or more precursor phosphate salts and one or more non-phosphate compounds; wherein said one or more non-phosphate compounds are substantially chemically inert to said one or more precursor phosphate salts; wherein said one or more precursor phosphate salts consist essentially of: i) one or more monovalent cations, and ii) one or more phosphate anions selected from the group represented by molecular formulae (IV) and (V):

$$[H_2P_yO_{(3y+1)}]^{p-} \qquad (IV)$$

$$[PO_3]_z^{z-} \qquad (V);$$

wherein y is any integer equal to or greater than 1 and z is any integer equal to or greater than 3; wherein said one or more precursor phosphate salts are neutrally charged; with (b) a gas mixture comprising water vapor;
wherein the water partial pressure in said gas mixture is equal to or greater than the water partial pressure at the triple point of at least one of said one or more precursor phosphate salts; wherein said contacting step between said dehydration catalyst precursor mixture and said gas mixture is performed at a temperature equal to or greater than the temperature at the triple point of at least one of said one or more precursor phosphate salts; wherein one or more amorphous phosphate salts are produced as a result of said one or more precursor phosphate salts being contacted with said water vapor.

In another embodiment of the present invention, a method of preparing a dehydration catalyst is provided. The method comprises contacting:

(a) a dehydration catalyst precursor mixture comprising one or more precursor phosphate salts and one or more non-phosphate compounds; and wherein said one or more non-phosphate compounds are substantially chemically inert to said one or more precursor phosphate salts; wherein said one or more precursor phosphate salts consist essentially of: i) one or more monovalent cations, and ii) one or more phosphate anions selected from the group represented by molecular formulae (IV) and (V):

$$[H_2P_yO_{(3y+1)}]^{p-} \qquad (IV)$$

$$[PO_3]_z^{z-} \qquad (V);$$

wherein y is any integer equal to or greater than 1 and z is any integer equal to or greater than 3; wherein said one or more precursor phosphate salts are neutrally charged; with (b) a gas mixture comprising water vapor;
wherein the water partial pressure in said gas mixture is equal to or greater than about 4 bar; wherein said contacting step between said dehydration catalyst precursor mixture and said gas mixture is performed at a temperature equal to or greater than about 250° C.; wherein one or more amorphous phosphate salts are produced as a result of said one or more precursor phosphate salts being contacted with said water vapor.

In yet another embodiment of the present invention, a method of preparing a dehydration catalyst is provided. The method comprises contacting:

(a) a dehydration catalyst precursor mixture comprising: i) $KH_2PO_4$ or $(KPO_3)_n$, and ii) amorphous silica; with (b) a gas mixture comprising water vapor;
wherein the water partial pressure in said gas mixture is equal to or greater than about 0.8 bar; wherein said contacting step between said dehydration catalyst precursor mixture and said gas mixture is performed at a temperature equal to or greater than about 250° C.; wherein one or more amorphous phosphate salts are produced as a result of said one or more precursor phosphate salts being contacted with said water vapor.

BRIEF DESCRIPTION OF THE DRAWINGS

For a more complete understanding of the disclosure, reference should be made to the following detailed description and drawing Figures.

Figure 1:
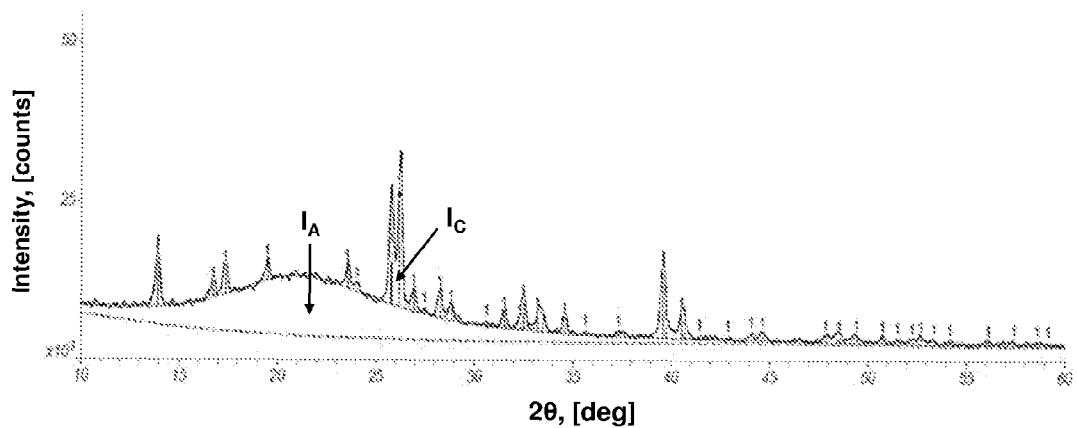
FIG. 1 illustrates the calculation of amorphous content in the dehydration catalyst using an XRD technique. The separate amorphous ($I_A$) and crystalline ($I_C$) contributions to the scattering pattern are determined using a profile-fitting technique, after appropriate background subtraction.

While the disclosed catalysts and methods are susceptible of embodiments in various forms, there are illustrated in the figures (and will hereafter be described) specific embodiments of the invention, with the understanding that the disclosure is intended to be illustrative, and is not intended to limit the invention to the specific embodiments described and illustrated herein.

DETAILED DESCRIPTION OF THE INVENTION

I. Definitions

As used herein, the term "bio-based" material refers to a renewable material.

As used herein, the term "renewable material" refers to a material that is produced from a renewable resource.

As used herein, the term "renewable resource" refers to a resource that is produced via a natural process at a rate comparable to its rate of consumption (e.g., within a 100 year time frame). The resource can be replenished naturally, or via agricultural techniques. Non-limiting examples of renewable resources include plants (e.g., sugar cane, beets, corn, potatoes, citrus fruit, woody plants, lignocellulose, hemicellulose, and cellulosic waste), animals, fish, bacteria, fungi, and forestry products. These resources can be naturally occurring, hybrids, or genetically engineered organisms. Natural resources, such as crude oil, coal, natural gas, and peat, which take longer than 100 years to form, are not considered renewable resources. Because at least part of the material of the invention is derived from a renewable resource, which can sequester carbon dioxide, use of the material can reduce global warming potential and fossil fuel consumption.

As used herein, the term "petroleum-based" material refers to a material that is produced from fossil material, such as petroleum, natural gas, coal, etc.

As used herein, the term "catalyst" refers to either a pre-reaction catalyst (also called a catalyst precursor mixture) or an in-situ catalyst. The pre-reaction catalyst is the catalyst loaded into the chemical reactor, and the in-situ catalyst is the catalyst present in the reactor during the reaction. In general, a catalyst increases the reaction rate without being consumed in the reaction. Finally, a pre-reaction catalyst can remain unchanged during the reaction or undergo in-situ physical or chemical transformations during the reaction that can change its physical and chemical properties and become an in-situ catalyst.

As used herein, the term "monophosphate" or "orthophosphate" refers to any salt whose anionic entity, $[PO_4]^{3-}$, is composed of four oxygen atoms arranged in an almost regular tetrahedral array about a central phosphorus atom.

As used herein, the term "condensed phosphate" refers to any salts containing one or several P—O—P bonds generated by corner sharing of $PO_4$ tetrahedra.

As used herein, the term "polyphosphate" refers to any condensed phosphates with a linear structure; i.e. containing linear P—O—P linkages by corner sharing of $PO_4$ tetrahedra leading to the formation of finite chains.

As used herein, the term "cyclophosphate" refers to any condensed phosphate with a cyclic structure.

As used herein, the term "hydrated" refers to a hydrated crystalline salt or hydrated crystalline compound that contains a specific number of water molecules per formula unit of the salt or compound.

As used herein, the term "monovalent cation" refers to any cation with a positive charge of +1.

As used herein, the term "polyvalent cation" refers to any cation with a positive charge equal or greater than +2.

As used herein, the term "anion" refers to any atom or group of covalently-bonded atoms having a negative charge.

As used herein, the term "heteropolyanion" refers to any anion with covalently bonded $XO_p$ and $YO_r$ polyhedra, and thus comprises X—O—Y and possibly X—O—X and Y—O—Y bonds, wherein X and Y represent any atoms, and wherein p and r are any positive integers.

As used herein, the term "heteropolyphosphate" refers to any heteropolyanion, wherein X represents phosphorus (P) and Y represents any other atom.

As used herein, the term "phosphate adduct" refers to any compound with one or more phosphate anions and one or more non-phosphate anions that are not covalently linked.

As used herein, the term "amorphous" refers to the state of any condensed phase material that lacks the long-range order characteristic of a crystalline material. An amorphous material can be either an amorphous solid or a liquid. In the context of the present invention, materials with more than 50 wt % of amorphous content are considered amorphous materials.

As used herein, the term "crystalline" refers to the state of any condensed phase material whose constituents are arranged in a highly ordered microscopic structure, forming a crystal lattice with long-range order. In the context of the present invention, materials with less than 50 wt % of amorphous content are considered crystalline materials.

As used herein, the term "chemically inert" materials refers to materials which remain in the same chemical form, under equilibrium conditions, when contacted with another material or materials. In the context of the present invention, more than about 90 wt % of the material should remain in the same chemical form to be considered a "substantially chemically inert" material and more than about 98 wt % of the material should remain in the same chemical form to be considered an "essentially chemically inert" material.

As used herein, the term "antioxidant" refers to a molecule capable of terminating radical chain processes by either donating a hydrogen atom or the reaction of an olefinic bond to form a stabilized organic radical and thus terminate radical chain processes. Non limiting examples of antioxidants comprise thiols, polyphenols, butylated hydroxy toluene (BHA), and butylated hydroxy anisole (BHA).

As used herein, the terms "LA" refers to lactic acid, "AA" refers to acrylic acid, "AcH" refers to acetaldehyde, "PA" refers to propionic acid, "LAC" refers to LA conversion in mol %, "AAY" refers to AA yield in mol %, "AAS" refers to AA selectivity in mol %, "PAS" refers to PA selectivity in mol %, "AcHY" refers to acetaldehyde yield in mol %, and "23PDY" refers to 2,3-pentanedione yield in mol %.

As used herein, the term "conversion" in % is defined as [hydroxypropionic acid, hydroxypropionic acid derivatives, or mixtures thereof flow rate in (mol/min)–hydroxypropionic acid, hydroxypropionic acid derivatives, or mixtures thereof flow rate out (mol/min)]/[hydroxypropionic acid, hydroxypropionic acid derivatives, or mixtures thereof flow rate in (mol/min)]×100. For the purposes of this invention, the term "conversion" means molar conversion, unless otherwise noted.

As used herein, the term "yield" in % is defined as [product flow rate out (mol/min)/hydroxypropionic acid, hydroxypropionic acid derivatives, or mixtures thereof flow rate in (mol/min)]×100. For the purposes of this invention, the term "yield" means molar yield, unless otherwise noted.

As used herein, the term "selectivity" in % is defined as [Yield/Conversion]×100. For the purposes of this invention, the term "selectivity" means molar selectivity, unless otherwise noted.

As used herein, the term "total carbon balance" is defined as: [((mol carbon monoxide out+mol carbon dioxide out+mol methane out)+(2×(mol acetic acid out+mol acetaldehyde out+mol ethane out+mol ethylene out))+(3×(mol acrylic acid out+mol propionic acid out+mol hydroxypropionic acid out+mol hydroxyacetone out)+(5×mol 2.3 pentanedione out)+(6×mol acrylic acid dimer out))/(3×mol hydroxypropionic acid in)]×100. If hydroxypropionic acid derivative is used instead of hydroxypropionic acid, the above formula needs to be adjusted according to the number of carbon atoms in the hydroxypropionic acid derivative.

As used herein, the term "Gas Hourly Space Velocity" or "GHSV" in $h^{-1}$ is defined as 60×[Total gas flow rate (mL/min)/catalyst empty bed volume (mL)]. The total gas flow rate is calculated under Standard Temperature and Pressure conditions (STP; 0° C. and 1 atm).

As used herein, the term "Weight Hourly Space Velocity" or "WHSV" in $h^{-1}$ is defined as 60×[Total LA flow rate (g/min)/catalyst weight (g)].

As used herein, the term "Liquid Hourly Space Velocity" or "LHSV" in $h^{-1}$ is defined as 60×[Total liquid flow rate (mL/min)/catalyst bed volume (mL)].

II. Catalysts for the Conversion of Hydroxypropionic Acid or its Derivatives to Acrylic Acid or its Derivatives Unexpectedly, it has been found that catalysts comprising a mixture of partially dehydrated dihydrogen monophosphates of monovalent cations in the amorphous state can dehydrate hydroxypropionic acid, hydroxypropionic acid derivatives, or mixtures thereof to acrylic acid, acrylic acid derivatives, or mixtures thereof with high: 1) yield and selectivity for acrylic acid, acrylic acid derivatives, or mixtures thereof, i.e., low amount and few side products; 2) efficiency, i.e., performance in short residence time; and 3) longevity. As a non limiting example, these amorphous phosphate salts can be formed reversibly when crystalline phosphate salts (e.g. monophosphates, polyphosphates, or cyclophosphates) of monovalent cations with molar ratio of phosphorus to cations of about 1 are contacted with water at elevated water partial pressure and temperature. The applicants also found unexpectedly, that in order to dehydrate hydroxypropionic acid, hydroxypropionic acid derivatives, or mixtures thereof to acrylic acid, acrylic acid derivatives, or mixtures thereof, the dehydration catalyst of the present invention needs to be in the presence of sufficient water vapor, contrary to common belief in the art of performing dehydration reactions under dry conditions. Although not wishing to be bound by any theory, applicants hypothesize that the water vapor is required to avoid full dehydration of the dihydrogen monophosphate salts to condensed phosphates under operation conditions, maintaining the Brønsted acid sites that are required for the selective acid-catalyzed dehydration of hydroxypropionic acid and its derivatives to acrylic acid and its derivatives.

In one embodiment of the present invention, the dehydration catalyst comprises one or more amorphous phosphate salts; wherein said one or more amorphous phosphate salts consist essentially of: (a) one or more cations, and (b) one or more phosphate anions selected from the group represented by empirical formula (I):

$[H_{2(1-x)}PO_{(4-x)}]^-$     (I);

wherein x is any real number equal to or greater than 0 and equal to or less than 1; and wherein said one or more amorphous phosphate salts of said dehydration catalyst are neutrally charged. In another embodiment of the present invention, at least one of said one or more amorphous phosphate salts is replaced by one or more crystalline phosphate salts consisting essentially of: (a) one or more cations, and (b) one or more phosphate anions selected from the group represented by empirical formula (I); wherein x is any real number equal to or greater than 0 and equal to or less than 1 such that the salt is crystalline; and wherein said one or more crystalline phosphate salts of said dehydration catalyst are neutrally charged. In another embodiment of the present invention, said one or more cations are selected from the group consisting of monovalent cations, polyvalent cations, and mixtures thereof. In yet another embodiment of the present invention, said one or more cations are selected from the group consisting of monovalent cations.

In one embodiment of the present invention, the dehydration catalyst comprises one or more amorphous phosphate salts; wherein said one or more amorphous phosphate salts consist essentially of: (a) one or more monovalent cations, and (b) one or more phosphate anions selected from the group represented by empirical formula (I):

$[H_{2(1-x)}PO_{(4-x)}]^-$     (I);

wherein x is any real number equal to or greater than 0 and equal to or less than 1; and wherein said one or more amorphous phosphate salts of said dehydration catalyst are neutrally charged. In another embodiment of the present invention, at least one of said one or more amorphous phosphate salts is replaced by one or more crystalline phosphate salts consisting essentially of: (a) one or more monovalent cations, and (b) one or more phosphate anions selected from the group represented by empirical formula (I); wherein x is any real number equal to or greater than 0 and equal to or less than 1 such that the salt is crystalline; wherein said one or more crystalline phosphate salts of said dehydration catalyst are neutrally charged.

The amorphous phosphate salts that comprise one or more phosphate anions represented by empirical formula (I) can be a mixture of amorphous monophosphates and polyphosphates of different length (e.g. $M^IH_2PO_4$, $M^I_2H_2P_2O_7$, $M^I_3H_2P_3O_{10}$, $M^I_4H_2P_4O_{13}$, ... $M^I_nH_2P_nO_{(3n+1)}$; wherein $M^I$ is a monovalent cation). As a non limiting example, this mixture can be produced by partial dehydration of dihydrogen monophosphates or by partial hydrolysis of condensed phosphates with molar ratio of phosphorus to cations of about 1. The amorphous phosphate salts can also comprise any hydrated form of said monophosphates and polyphosphates. In the context of the present invention, the variable x in empirical formula (I) refers either to the composition of single species within said mixture of monophosphates and polyphosphates or to the average composition of said mixture.

In the context of the present invention, a phosphate salt or a mixture of phosphate salts with more than 50 wt % of amorphous content (or less than 50 wt % of crystalline content) are considered amorphous phosphate salts. The amorphous content can be determined by any method known to those skilled in the art, such as, by way of example and not limitation, x-ray diffraction (XRD), infrared spectroscopy (IR), Raman spectroscopy, differential scanning calorimetry (DSC), or solid-state nuclear magnetic resonance (NMR) spectroscopy. As an illustration, in a method based on an XRD technique (see FIG. 1), the separate crystalline ($I_C$) and amorphous ($I_A$) contributions on the X-ray scattering pattern are determined using a profile-fitting technique. This deconvolution of the scattering pattern into the separate contributions can be performed using Gaussian, Lorentzian, Voigt, or related functions known to those skilled in the art. Then, the amorphous content, $X_A$, is determined by calculating the ratio between the area of scattered intensity for the amorphous contribution ($I_A$) and the area of the total scattered intensity (crystalline plus amorphous contributions, $I_T=I_C+I_A$) for a defined Bragg angle range (e.g. 2θ=5° to 50°, Cu-radiation λ=1.54059 Å, in the context of the current invention), i.e. $X_A=I_A/I_C+I_A×100$ wt %.

In one embodiment of the present invention, the dehydration catalyst comprises one or more amorphous phosphate salts represented by empirical formula (Ia):

$$M^I H_{2(1-x)} PO_{(4-x)} \qquad (Ia);$$

wherein $M^I$ is a monovalent cation; wherein x is any real number equal to or greater than 0 and equal to or less than 1. In another embodiment of the present invention, at least one of said one or more amorphous phosphate salts is replaced by one or more crystalline phosphate salts represented by empirical formula (Ia); wherein $M^I$ is a monovalent cation; wherein x is any real number equal to or greater than 0 and equal to or less than 1.

In one embodiment of the present invention, the dehydration catalyst comprises one or more amorphous phosphate salts represented by empirical formula (Ib):

$$M_w^I N_{(1-w)}^I H_{2(1-x)} PO_{(4-x)} \qquad (Ib);$$

wherein $M^I$ and $N^I$ are two different monovalent cations; wherein x is any real number equal to or greater than 0 and equal to or less than 1; wherein w is any real number greater than 0 and less than 1. In another embodiment of the present invention, at least one of said one or more amorphous phosphate salts is replaced by one or more crystalline phosphate salts represented by empirical formula (Ib); wherein $M^I$ and $N^I$ are two different monovalent cations; wherein x is any real number equal to or greater than 0 and equal to or less than 1; wherein w is any real number greater than 0 and less than 1.

In the context of the present invention, "one or more cations" refers to different types of cations and "one or more anions" refers to different types of anions. Non limiting examples of cations are metallic cations, organo-metallic cations, ammonium, substituted ammonium, oxycations, and other cations known by those skilled in the art. Non limiting examples of substituted ammonium and other cations are isopropylammonium, ethylenediammonium, sarcosinium, L-histidinium, glycinium, and 4-aminopyridinium. Non limiting examples of oxycations are pervanadyl and vanadyl ions.

Non limiting examples of monovalent cations of said one or more amorphous phosphate salts are cations of alkali metals, organo-metallic cations, ammonium, substituted ammonium, oxycations (e.g. pervanadyl), and other cations known by those skilled in the art. In one embodiment of the present invention, said one or more monovalent cations of said one or more amorphous phosphate salts are selected from the group consisting of $Li^+$, $Na^+$, $K^+$, $Rb^+$, $Cs^+$, $Ag^+$, $Tl^+$, and mixtures thereof. In another embodiment of the present invention, said one or more monovalent cations of said one or more amorphous phosphate salts are selected from the group consisting of $Na^+$, $K^+$, $Rb^+$, $Cs^+$, and mixtures thereof. In yet another embodiment of the present invention, said one or more monovalent cations of said one or more amorphous phosphate salts is $K^+$.

In another embodiment of the present invention, at least one of said one or more amorphous phosphate salts consists of two or more different monovalent cations selected from the group consisting of $Li^+$, $Na^+$, $K^+$, $Rb^+$, $Cs^+$, $Ag^+$, and $Tl^+$. In another embodiment of the present invention, at least one of said one or more amorphous phosphate salts consists of two or more different monovalent cations selected from the group consisting of $Na^+$, $K^+$, $Rb^+$, and $Cs^+$. In one embodiment of the present invention, the amorphous phosphate salts are selected from the group consisting of $LiH_{2(1-x)}PO_{(4-x)}$, $NaH_{2(1-x)}PO_{(4-x)}$, $KH_{2(1-x)}PO_{(4-x)}$, $RbH_{2(1-x)}PO_{(4-x)}$, $CsH_{2(1-x)}PO_{(4-x)}$, any of their hydrated forms, and mixtures thereof; wherein x is any real number equal to or greater than 0 and equal to or less than 1. In another embodiment of the present invention, the amorphous phosphate salt is $KH_{2(1-x)}PO_{(4-x)}$; wherein x is any real number equal to or greater than 0 and equal to or less than 1.

In one embodiment of the present invention, the amorphous phosphate salts are selected from the group consisting of $Li_wNa_{(1-w)}H_{2(1-x)}PO_{(4-x)}$, $Li_wK_{(1-w)}H_{2(1-x)}PO_{(4-x)}$, $Li_wRb_{(1-w)}H_{2(1-x)}PO_{(4-x)}$, $Li_wCs_{(1-w)}H_{2(1-x)}PO_{(4-x)}$, $Na_wK_{(1-w)}H_{2(1-x)}PO_{(4-x)}$, $Na_wRb_{(1-w)}H_{2(1-x)}PO_{(4-x)}$, $Na_wCs_{(1-w)}H_{2(1-x)}PO_{(4-x)}$, $K_wRb_{(1-w)}H_{2(1-x)}PO_{(4-x)}$, $K_wCs_{(1-w)}H_{2(1-x)}PO_{(4-x)}$, $Rb_wCs_{(1-w)}H_{2(1-x)}PO_{(4-x)}$, any of their hydrated forms, and mixtures thereof; wherein x is any real number equal to or greater than 0 and equal to or less than 1; and wherein w is any real number greater than 0 and less than 1.

In one embodiment of the present invention, the dehydration catalyst comprises: (a) one or more amorphous phosphate salts consisting essentially of: i) one or more cations, and ii) one or more phosphate anions selected from the group represented by empirical formula (I):

$$[H_{2(1-x)}PO_{(4-x)}]^- \qquad (I);$$

wherein x is any real number equal to or greater than 0 and equal to or less than 1; and wherein said one or more amorphous phosphate salts of said dehydration catalyst are neutrally charged; and (b) one or more non-phosphate compounds; wherein said one or more non-phosphate compounds are substantially chemically inert to said one or more amorphous phosphate salts. In another embodiment of the present invention, at least one of said one or more amorphous phosphate salts is replaced by one or more crystalline phosphate salts consisting essentially of: i) one or more cations, and ii) one or more phosphate anions selected from the group represented by empirical formula (I); wherein x is any real number equal to or greater than 0 and equal to or less than 1; wherein said one or more crystalline phosphate salts of said dehydration catalyst are neutrally charged. In another embodiment of the present invention, said one or more cations are selected from the group consisting of monovalent cations, polyvalent cations, and mixtures thereof. In yet another embodiment of the present invention, said one or more cations are selected from the group consisting of monovalent cations.

In one embodiment of the present invention, the dehydration catalyst comprises: (a) one or more amorphous phosphate salts consisting essentially of: i) one or more monovalent cations, and ii) one or more phosphate anions selected from the group represented by empirical formula (I):

$$[H_{2(1-x)}PO_{(4-x)}]^- \qquad (I);$$

wherein x is any real number equal to or greater than 0 and equal to or less than 1; and wherein said one or more amorphous phosphate salts of said dehydration catalyst are neutrally charged; and (b) one or more non-phosphate compounds; wherein said one or more non-phosphate compounds are substantially chemically inert to said one or more amorphous phosphate salts. In another embodiment of the present invention, said one or more non-phosphate compounds are essentially chemically inert to said one or more amorphous phosphate salts. In another embodiment of the present invention, said one or more non-phosphate compounds are chemically inert to said one or more amorphous phosphate salts. In yet another embodiment of the present invention, at least one of said one or more amorphous phosphate salts is replaced by one or more crystalline phosphate salts consisting essentially of: i) one or more monovalent cations, and ii) one or more phosphate anions selected from the group represented by empirical formula (I); wherein x is any real number equal to or greater than 0 and equal to or less than 1; wherein said one or more crystalline phosphate salts of said dehydration catalyst are neutrally charged.

In one embodiment of the present invention, the dehydration catalyst comprises: (a) one or more amorphous phosphate salts represented by empirical formula (Ia):

$$M^I H_{2(1-x)} PO_{(4-x)} \quad (Ia);$$

wherein $M^I$ is a monovalent cation; wherein x is any real number equal to or greater than 0 and equal to or less than 1; and (b) one or more non-phosphate compounds; wherein said one or more non-phosphate compounds are substantially chemically inert to said one or more amorphous phosphate salts. In another embodiment of the present invention, said one or more non-phosphate compounds are essentially chemically inert to said one or more amorphous phosphate salts. In another embodiment of the present invention, said one or more non-phosphate compounds are chemically inert to said one or more amorphous phosphate salts. In yet another embodiment of the present invention, at least one of said one or more amorphous phosphate salts is replaced by one or more crystalline phosphate salts represented by empirical formula (Ia); wherein $M^I$ is a monovalent cation; wherein x is any real number equal to or greater than 0 and equal to or less than 1.

In one embodiment of the present invention, the dehydration catalyst comprises: (a) one or more amorphous phosphate salts represented by empirical formula (Ib):

$$M^I_w N^I_{(1-w)} H_{2(1-x)} PO_{(4-x)} \quad (Ib);$$

wherein $M^I$ and $N^I$ are two different monovalent cations; wherein x is any real number equal to or greater than 0 and equal to or less than 1; wherein w is any real number greater than 0 and less than 1; and (b) one or more non-phosphate compounds; wherein said one or more non-phosphate compounds are substantially chemically inert to said one or more amorphous phosphate salts. In another embodiment of the present invention, said one or more non-phosphate compounds are essentially chemically inert to said one or more amorphous phosphate salts. In another embodiment of the present invention, said one or more non-phosphate compounds are chemically inert to said one or more amorphous phosphate salts. In yet another embodiment of the present invention, at least one of said one or more amorphous phosphate salts is replaced by one or more crystalline phosphate salts represented by empirical formula (Ib); wherein $M^I$ and $N^I$ are two different monovalent cations; wherein x is any real number equal to or greater than 0 and equal to or less than 1; wherein w is any real number greater than 0 and less than 1.

In another embodiment of the present invention, the weight ratio between the total amount of said one or more amorphous phosphate salts and the total amount of said one or more non-phosphate compounds is between about 1:10 and about 4:1.

In one embodiment of the present invention, said one or more non-phosphate compounds comprises silicon oxide ($SiO_2$). In another embodiment of the present invention, said one or more non-phosphate compounds consists essentially of silicon oxide ($SiO_2$). In another embodiment of the present invention, said silicon oxide is selected from the group consisting of amorphous silica, quartz, tridymite, cristobalite, moganite, coesite, and mixtures thereof. In another embodiment of the present invention, said silicon oxide is amorphous silica. In yet another embodiment of the present invention, said silicon oxide has a specific surface area of less than about 10 m²/g.

In another embodiment of the present invention, said one or more amorphous phosphate salts are selected from the group consisting of $LiH_{2(1-x)}PO_{(4-x)}$, $NaH_{2(1-x)}PO_{(4-x)}$, $KH_{2(1-x)}PO_{(4-x)}$, $RbH_{2(1-x)}PO_{(4-x)}$, $CsH_{2(1-x)}PO_{(4-x)}$, any of their hydrated forms, and mixtures thereof, wherein x is any real number equal to or greater than 0 and equal to or less than 1; and said one or more non-phosphate compounds are selected from the group consisting of amorphous silica, quartz, and mixtures thereof. In another embodiment of the present invention, said one or more amorphous phosphate salts is $KH_{2(1-x)}PO_{(4-x)}$, wherein x is any real number equal to or greater than 0 and equal to or less than 1; and said one or more non-phosphate compounds is amorphous silica.

In another embodiment of the present invention, said one or more amorphous phosphate salts are selected from the group consisting of $Li_wNa_{(1-w)}H_{2(1-x)}PO_{(4-x)}$, $Li_wK_{(1-w)}H_{2(1-x)}PO_{(4-x)}$, $Li_wRb_{(1-w)}H_{2(1-x)}P_{(4-x)}$, $Li_wCs_{(1-w)}H_{2(1-x)}PO_{(4-x)}$, $Na_wK_{(1-w)}H_{2(1-x)}PO_{(4-x)}$, $Na_wRb_{(1-w)}H_{2(1-x)}PO_{(4-x)}$, $Na_wCs_{(1-w)}H_{2(1-x)}PO_{(4-x)}$, $K_wRb_{(1-w)}H_{2(1-x)}PO_{(4-x)}$, $K_wCs_{(1-w)}H_{2(1-x)}PO_{(4-x)}$, $Rb_wCs_{(1-w)}H_{2(1-x)}PO_{(4-x)}$, any of their hydrated forms, and mixtures thereof; wherein x is any real number equal to or greater than 0 and equal to or less than 1; wherein w is any real number greater than 0 and less than 1; and said one or more non-phosphate compounds are selected from the group consisting of amorphous silica, quartz, and mixtures thereof.

In one embodiment of the present invention, said one or more non-phosphate compounds comprise one or more oxysalts comprising: (a) one or more polyvalent cations, and (b) one or more oxyanions selected from the group represented by molecular formulae (II) and (III):

$$[H_{(a-2b)}S_cO_{(4c-b)}]^{(2c-a)-} \quad (II)$$

$$[Ta_{2d}O_{(5d+e)}]^{2e-} \quad (III);$$

wherein a and b are positive integers or zero; wherein c, d, and e are positive integers; wherein (a–2b) is equal to or greater than zero; wherein (2c–a) is greater than zero; wherein said one or more oxysalts are neutrally charged. In another embodiment of the present invention, said one or more non-phosphate compounds further comprise silicon oxide ($SiO_2$).

In another embodiment of the present invention, said one or more non-phosphate compounds comprise one or more oxysalts comprising: (a) one or more polyvalent cations, (b) one or more monovalent cations, and (c) one or more oxyanions selected from the group represented by molecular formulae (II) and (III):

$$[H_{(a-2b)}S_cO_{(4c-b)}]^{(2c-a)-} \quad (II)$$

$$[Ta_{2d}O_{(5d+e)}]^{2e-} \quad (III);$$

wherein a and b are positive integers or zero; wherein c, d, and e are positive integers; wherein (a–2b) is equal to or greater than zero; wherein (2c–a) is greater than zero; wherein said one or more oxysalts are neutrally charged. In another embodiment of the present invention, said one or more non-phosphate compounds further comprise silicon oxide ($SiO_2$).

Non limiting examples of said one or more polyvalent cations of said one or more oxysalts are cations of alkaline earth metals, transition metals, post-transition or poor metals, and metalloids; organo-metallic cations, substituted ammonium cations, oxycations (e.g. vanadyl), and other cations known by those skilled in the art. In one embodiment of the present invention, said one or more polyvalent cations of said one or more oxysalts are selected from the group consisting of the cations of the metals Be, Mg, Ca, Sr, Ba, Sc, Y, Ti, Zr, Hf, V, Nb, Ta, Cr, Mo, W, Mn, Re, Al, Ga, In, Tl, Si, Ge, Sn, Pb, Sb, Bi, La, Ce, Pr, Nd, Sm, Eu, Gd, Tb, Dy, Ho, Er, Tm, Yb, Lu, and mixtures thereof. In another embodiment of the present invention, said one or more polyvalent cations of said one or more oxysalts are selected from the group consisting of the cations of the metals Mg, Ca, Sr, Ba, Y, Mn, Al, Er, and mixtures thereof. In another embodiment of the present invention, said one or more polyvalent cations of said one or more oxysalts are selected from the group consisting of divalent cations, trivalent cations, tetravalent cations, pentavalent cations, and mixtures thereof. In another embodiment of the present invention, said one or more polyvalent cations of said one or more oxysalts are selected from the group consisting of $Be^{2+}$, $Mg^{2+}$, $Ca^{2+}$, $Sr^{2+}$, $Ba^{2+}$, $Sc^{3+}$, $Y^{3+}$, $Ti^{3+}$, $Ti^{4+}$, $Zr^{2+}$, $Zr^{4+}$, $Hf^{4+}$, $V^{3+}$, $V^{4+}$, $Nb^{3+}$, $Cr^{2+}$, $Cr^{3+}$, $Mo^{3+}$, $Mo^{4+}$, $Mn^{2+}$, $Mn^{3+}$, $Re^{4+}$, $Al^{3+}$, $Ga^{3+}$, $In^{3+}$, $Si^{4+}$, $Ge^{4+}$, $Sn^{4+}$, $Pb^{4+}$, $Sb^{3+}$, $Sb^{5+}$, $Bi^{3+}$, $La^{3+}$, $Ce^{3+}$, $Ce^{4+}$, $Pr^{3+}$, $Nd^{3+}$, $Sm^{3+}$, $Eu^{3+}$, $Gd^{3+}$, $Tb^{3+}$, $Dy^{3+}$, $Ho^{3+}$, $Er^{3+}$, $Tm^{3+}$, $Yb^{3+}$, $Lu^{3+}$, and mixtures thereof. In another embodiment of the present invention, said one or more polyvalent cations of said one or more oxysalts are selected from the group consisting of $Mg^{2+}$, $Ca^{2+}$, $Sr^{2+}$, $Ba^{2+}$, $Y^{3+}$, $Mn^{2+}$, $Mn^{3+}$, $Al^{3+}$, $Er^{3+}$, and mixtures thereof. In yet another embodiment of the present invention, said one or more polyvalent cations of said one or more oxysalts is $Ba^{2+}$.

Non limiting examples of said one or more monovalent cations of said one or more oxysalts are cations of alkali metals. In one embodiment of the present invention, said one or more monovalent cations of said one or more oxysalts are selected from the group consisting of the cations of the metals Li, Na, K, Rb, Cs, Ag, Tl, and mixtures thereof; and said one or more polyvalent cations of said one or more oxysalts are selected from the group consisting of the cations of the metals Be, Mg, Ca, Sr, Ba, Sc, Y, Ti, Zr, Hf, V, Nb, Ta, Cr, Mo, W, Mn, Re, Al, Ga, In, Tl, Si, Ge, Sn, Pb, Sb, Bi, La, Ce, Pr, Nd, Sm, Eu, Gd, Tb, Dy, Ho, Er, Tm, Yb, Lu, and mixtures thereof. In another embodiment of the present invention, said one or more monovalent cations of said one or more oxysalts are selected from the group consisting of the cations of the metals K, Rb, Cs, and mixtures thereof; and said one or more polyvalent cations of said one or more oxysalts are selected from the group consisting of the cations of the metals Mg, Ca, Sr, Ba, Y, Mn, Al, Er, and mixtures thereof.

In another embodiment of the present invention, said one or more oxyanions of said one or more oxysalts are selected from the group represented by molecular formulae (IIa) to (IId), (IIIa) to (IIIg), and mixtures thereof:

$$[SO_4]^{2-} \tag{IIa}$$

$$[S_2O_7]^{2-} \tag{IIb}$$

$$[HSO_4]^{1-} \tag{IIc}$$

$$[SO_4]^{2-}\cdot[HSO_4]^{-} \tag{IId}$$

$$[Ta_2O_6]^{2-} \tag{IIIa}$$

$$[Ta_2O_7]^{4-} \tag{IIIb}$$

$$[Ta_2O_9]^{8-} \tag{IIIc}$$

$$[Ta_2O_{10}]^{10-} \tag{IIId}$$

$$[Ta_2O_{11}]^{12-} \tag{IIIe}$$

$$[Ta_4O_{11}]^{2-} \tag{IIIf}$$

$$[Ta_4O_{15}]^{10-} \tag{IIIg}.$$

In another embodiment of the present invention, said one or more oxyanions of said one or more oxysalts are selected from the group represented by molecular formulae (IIa), (IIIa), and mixtures thereof:

$$[SO_4]^{2-} \tag{IIa}$$

$$[Ta_2O_6]^{2-} \tag{IIIa}.$$

Non limiting examples of said one or more oxysalts are sulfates of alkaline-earth metals, tantalates of alkaline-earth metals, sulfates of mixed alkali and alkaline earth metals, and tantalates of mixed alkali and alkaline earth metals. In one embodiment of the present invention, said one or more oxysalts are selected from the group consisting of $CaSO_4$, $SrSO_4$, $BaSO_4$, $SrK_2(SO_4)_2$, $SrRb_2(SO_4)_2$, $Ca_2K_2(SO_4)_3$, $Ca_2Rb_2(SO_4)_3$, $Ca_2Cs_2(SO_4)_3$, $CaTa_4O_{11}$, $SrTa_4O_{11}$, $BaTa_4O_{11}$, $MgTa_2O_6$, $CaTa_2O_6$, $SrTa_2O_6$, $BaTa_2O_6$, $Mg_2Ta_2O_7$, $Ca_2Ta_2O_7$, $Sr_2Ta_2O_7$, $SrK_2Ta_2O_7$, $Ba_2Ta_2O_7$, $Ba_3Ta_2O_8$, $Mg_4Ta_2O_9$, $Ca_4Ta_2O_9$, $Sr_4Ta_2O_9$, $Ba_4Ta_2O_9$, $Ca_5Ta_2O_{10}$, $Ca_2KTa_3O_{10}$, $Ca_2RbTa_3O_{10}$, $Ca_2CsTa_3O_{10}$, $Sr_2KTa_3O_{10}$, $Sr_2RbTa_3O_{10}$, $Sr_2CsTa_3O_{10}$, $Mg_5Ta_4O_{15}$, $Sr_5Ta_4O_{15}$, $BaSTa_4O_{15}$, $Sr_2KTa_5O_{15}$, $Ba_2KTa_5O_{15}$, $Sr_6Ta_2O_{11}$, $Ba_6Ta_2O_{11}$, any of their hydrated forms, and mixtures thereof. In another embodiment of the present invention, said one or more oxysalts are selected from the group consisting of $CaSO_4$, $CaTa_2O_6$, $SrSO_4$, $SrTa_2O_6$, $BaSO_4$, $BaTa_2O_6$, any of their hydrated forms, and mixtures thereof. In yet another embodiment of the present invention, said one or more oxysalts are selected from the group consisting of $BaSO_4$, $BaTa_2O_6$, any of their hydrated forms, and mixtures thereof.

In another embodiment of the present invention, said one or more amorphous phosphate salts are selected from the group consisting of $KH_{2(1-x)}PO_{(4-x)}$, $RbH_{2(1-x)}PO_{(4-x)}$, $CsH_{2(1-x)}PO_{(4-x)}$, any of their hydrated forms, and mixtures thereof; wherein x is any real number equal to or greater than 0 and equal to or less than 1; and said one or more non-phosphate compounds are selected from the group consisting of $CaSO_4$, $CaTa_2O_6$, $SrSO_4$, $SrTa_2O_6$, $BaSO_4$, $BaTa_2O_6$, any of their hydrated forms, and mixtures thereof. In another embodiment of the present invention, said one or more amorphous phosphate salts is $KH_{2(1-x)}PO_{(4-x)}$, wherein x is any real number equal to or greater than 0 and equal to or less than 1; and said one or more non-phosphate compounds is $BaSO_4$.

In another embodiment of the present invention, said one or more amorphous phosphate salts are selected from the group consisting of $K_wRb_{(1-w)}H_{2(1-x)}PO_{(4-x)}$, $K_wCs_{(1-w)}H_{2(1-x)}PO_{(4-x)}$, $Rb_wCs_{(1-w)}H_{2(1-x)}PO_{(4-x)}$, any of their hydrated forms, and mixtures thereof; wherein x is any real number equal to or greater than 0 and equal to or less than 1; wherein w is any real number greater than 0 and less than 1; and said one or more non-phosphate compounds are selected from the group consisting of $CaSO_4$, $CaTa_2O_6$, $SrSO_4$, $SrTa_2O_6$, $BaSO_4$, $BaTa_2O_6$, any of their hydrated forms, and mixtures thereof.

The variable x in formulae (I), (Ia), and (Ib) is any real number equal to or greater than 0 and equal to or less than 1. In one embodiment of the present invention, x is equal to about 0. In another embodiment of the present invention, x is equal to about 1. In another embodiment of the present invention, x is less than about 0.8. In another embodiment of the present invention, x is less than about 0.6. In another embodiment of the present invention, x is less than about 0.5. In another embodiment of the present invention, x is between about 0.1 and about 0.5. In another embodiment of the present invention, x is between about 0.25 and about 0.45. In another embodiment of the present invention, x is equal to about 0.4. In yet another embodiment, x is equal to about 0.4 and said one or more monovalent cations is $Cs^+$. The variable w in formula (Ib) is any real number greater than 0 and less than 1. In one embodiment of the present invention, w is less than about 0.2 or greater than about 0.8. In another embodiment of the present invention, w is less than about 0.1 or greater than about 0.9.

In one embodiment of the present invention, the dehydration catalyst comprises one or more amorphous phosphate salts; wherein said one or more amorphous phosphate salts consist essentially of: (a) one or more monovalent cations, and (b) the phosphate anion represented by molecular formula (Ic):

$$[H_2PO_4]^- \tag{Ic}$$

wherein said one or more amorphous phosphate salts of said dehydration catalyst are neutrally charged. In another embodiment of the present invention, at least one of said one or more amorphous phosphate salts is replaced by one or more crystalline phosphate salts consisting essentially of: (a) one or more monovalent cations, and (b) the phosphate anion represented by molecular formula (Ic).

In one embodiment of the present invention, the dehydration catalyst comprises one or more amorphous phosphate salts represented by molecular formula (Id):

$$M^I H_2 PO_4 \tag{Id}$$

wherein $M^I$ is a monovalent cation. In another embodiment of the present invention, at least one of said one or more amorphous phosphate salts is replaced by one or more crystalline phosphate salts represented by molecular formula (Id).

In one embodiment of the present invention, the dehydration catalyst comprises one or more amorphous phosphate salts represented by molecular formula (Ie):

$$M^I_w N^I_{(1-w)} H_2 PO_4 \tag{Ie}$$

wherein $M^I$ and $N^I$ are two different monovalent cations; wherein w is any real number greater than 0 and less than 1. In another embodiment of the present invention, at least one of said one or more amorphous phosphate salts is replaced by one or more crystalline phosphate salts represented by molecular formula (Ie).

In one embodiment of the present invention, the dehydration catalyst comprises one or more amorphous phosphate salts; wherein said one or more amorphous phosphate salts consist essentially of: (a) one or more monovalent cations, and (b) the phosphate anion represented by empirical formula (If):

$$[PO_3]^- \tag{If}$$

wherein said one or more amorphous phosphate salts of said dehydration catalyst are neutrally charged. In another embodiment of the present invention, at least one of said one or more amorphous phosphate salts is replaced by one or more crystalline phosphate salts consisting essentially of: (a) one or more monovalent cations, and (b) the phosphate anion represented by empirical formula (If). In the context of the present invention, the anion represented by empirical formula (If) can refer either to the anion of cyclophosphate salts or to the anion of long-chain linear polyphosphate salts as described in "Phosphoric Acids and Phosphates, Kirk-Othmer Encyclopedia of Chemical Technology" by David R. Gard (published online: 15 Jul. 2005) and "Phosphorus: Chemistry, Biochemistry and Technology" by D. E. C. Corbridge (2013). When the empirical formula (If) refers to the anion of long chain polyphosphate salts, the empirical formula is not precise in that it does not include the minor perturbation of excess negative charge owing to the two end-group oxygens.

In one embodiment of the present invention, the dehydration catalyst comprises one or more amorphous phosphate salts represented by empirical formula (Ig):

$$M^I PO_3 \tag{Ig}$$

wherein $M^I$ is a monovalent cation. In another embodiment of the present invention, at least one of said one or more amorphous phosphate salts is replaced by one or more crystalline phosphate salts represented by empirical formula (Ig).

In one embodiment of the present invention, the dehydration catalyst comprises one or more amorphous phosphate salts represented by empirical formula (Ih):

$$M^I_w N^I_{(1-w)} PO_3 \tag{Ih}$$

wherein $M^I$ and $N^I$ are two different monovalent cations; wherein w is any real number greater than 0 and less than 1. In another embodiment of the present invention, at least one of said one or more amorphous phosphate salts is replaced by one or more crystalline phosphate salts represented by empirical formula (Ih). In the context of the present invention, the salts represented by empirical formula (Ig) or (Ih) can refer either to cyclophosphate salts or to long-chain linear polyphosphate salts as described in "Phosphoric Acids and Phosphates, Kirk-Othmer Encyclopedia of Chemical Technology" by David R. Gard (published online: 15 Jul. 2005) and "Phosphorus: Chemistry, Biochemistry and Technology" by D. E. C. Corbridge (2013). When the salts represented by empirical formulas (Ig) or (Ih) refer to long chain polyphosphate salts, the empirical formulae are not precise in that they do not include the minor amount of either protons or excess monovalent cations needed to produce a charge neutral structure owing to the two end group oxygens.

In one embodiment of the present invention, the dehydration catalyst comprises: (a) one or more amorphous phosphate salts consisting essentially of: i) one or more monovalent cations, and ii) the phosphate anion represented by molecular formula (Ic):

$$[H_2PO_4]^- \tag{Ic}$$

wherein said one or more amorphous phosphate salts of said dehydration catalyst are neutrally charged; and (b) one or more non-phosphate compounds; wherein said one or more non-phosphate compounds are substantially chemically inert to said one or more amorphous phosphate salts. In another embodiment of the present invention, said one or more non-phosphate compounds are essentially chemically inert to said one or more amorphous phosphate salts. In another embodiment of the present invention, said one or more non-phosphate compounds are chemically inert to said one or more amorphous phosphate salts. In yet another embodiment of the present invention, at least one of said one or more amorphous phosphate salts is replaced by one or more crystalline phosphate salts consisting essentially of: i) one or more monovalent cations, and ii) the phosphate anion represented by molecular formula (Ic).

In one embodiment of the present invention, the dehydration catalyst comprises: (a) one or more amorphous phosphate salts represented by molecular formula (Id):

$$M^I H_2 PO_4 \quad\quad\quad (Id);$$

wherein $M^I$ is a monovalent cation; and (b) one or more non-phosphate compounds; wherein said one or more non-phosphate compounds are substantially chemically inert to said one or more amorphous phosphate salts. In another embodiment of the present invention, said one or more non-phosphate compounds are essentially chemically inert to said one or more amorphous phosphate salts. In another embodiment of the present invention, said one or more non-phosphate compounds are chemically inert to said one or more amorphous phosphate salts. In yet another embodiment of the present invention, at least one of said one or more amorphous phosphate salts is replaced by one or more crystalline phosphate salts represented by molecular formula (Id).

In one embodiment of the present invention, the dehydration catalyst comprises: (a) one or more amorphous phosphate salts represented by molecular formula (Ie):

$$M^I_w N^I_{(1-w)} H_2 PO_4 \quad\quad\quad (Ie);$$

wherein $M^I$ and $N^I$ are two different monovalent cations; wherein w is any real number greater than 0 and less than 1; and (b) one or more non-phosphate compounds; wherein said one or more non-phosphate compounds are substantially chemically inert to said one or more amorphous phosphate salts. In another embodiment of the present invention, said one or more non-phosphate compounds are essentially chemically inert to said one or more amorphous phosphate salts. In another embodiment of the present invention, said one or more non-phosphate compounds are chemically inert to said one or more amorphous phosphate salts. In yet another embodiment of the present invention, at least one of said one or more amorphous phosphate salts is replaced by one or more crystalline phosphate salts represented by molecular formula (Ie).

In one embodiment of the present invention, the dehydration catalyst comprises: (a) one or more amorphous phosphate salts consisting essentially of: i) one or more monovalent cations, and ii) the phosphate anion represented by empirical formula (If):

$$[PO_3]^- \quad\quad\quad (If);$$

wherein said one or more amorphous phosphate salts of said dehydration catalyst are neutrally charged; and (b) one or more non-phosphate compounds; wherein said one or more non-phosphate compounds are substantially chemically inert to said one or more amorphous phosphate salts. In another embodiment of the present invention, said one or more non-phosphate compounds are essentially chemically inert to said one or more amorphous phosphate salts. In another embodiment of the present invention, said one or more non-phosphate compounds are chemically inert to said one or more amorphous phosphate salts. In yet another embodiment of the present invention, at least one of said one or more amorphous phosphate salts is replaced by one or more crystalline phosphate salts consisting essentially of: i) one or more monovalent cations, and ii) the phosphate anion represented by empirical formula (If).

In one embodiment of the present invention, the dehydration catalyst comprises: (a) one or more amorphous phosphate salts represented by empirical formula (Ig):

$$M^I PO_3 \quad\quad\quad (Ig);$$

wherein $M^I$ is a monovalent cation; and (b) one or more non-phosphate compounds; wherein said one or more non-phosphate compounds are substantially chemically inert to said one or more amorphous phosphate salts. In another embodiment of the present invention, said one or more non-phosphate compounds are essentially chemically inert to said one or more amorphous phosphate salts. In another embodiment of the present invention, said one or more non-phosphate compounds are chemically inert to said one or more amorphous phosphate salts. In yet another embodiment of the present invention, at least one of said one or more amorphous phosphate salts is replaced by one or more crystalline phosphate salts represented by empirical formula (Ig).

In one embodiment of the present invention, the dehydration catalyst comprises: (a) one or more amorphous phosphate salts represented by empirical formula (Ih):

$$M^I_w N^I_{(1-w)} PO_3 \quad\quad\quad (Ih);$$

wherein $M^I$ and $N^I$ are two different monovalent cations; wherein w is any real number greater than 0 and less than 1; and (b) one or more non-phosphate compounds; wherein said one or more non-phosphate compounds are substantially chemically inert to said one or more amorphous phosphate salts. In another embodiment of the present invention, said one or more non-phosphate compounds are essentially chemically inert to said one or more amorphous phosphate salts. In another embodiment of the present invention, said one or more non-phosphate compounds are chemically inert to said one or more amorphous phosphate salts. In yet another embodiment of the present invention, at least one of said one or more amorphous phosphate salts is replaced by one or more crystalline phosphate salts represented by empirical formula (Ih).

In one embodiment of the present invention, at least one of said one or more amorphous phosphate salts of said dehydration catalyst is a hydrated salt. In another embodiment of the present invention, at least one of said one or more crystalline phosphate salts of said dehydration catalyst is a hydrated salt. In another embodiment of the present invention, at least one of said one or more oxysalts of said dehydration catalyst is a hydrated salt. In another embodiment of the present invention, at least one of said one or more non-phosphate compounds of said dehydration catalyst is a hydrated compound. A hydrated salt or compound contains a specific number of water molecules per formula unit of the salt or compound. Non limiting examples of hydrated salts or compounds are hemihydrated, monohydrated, sesquihydrated, dehydrated, trihydrated, tetrahydrated, pentahydrated, hexahydrated, heptahydrated, octahydrated, nonahydrated, nonahydrated, and decahydrated salts or compounds.

In one embodiment of the present invention, said one or more non-phosphate compounds of said dehydration catalyst comprises one or more inert supports. In another embodiment of the present invention, said one or more non-phosphate compounds of said dehydration catalyst consists essentially of one or more inert supports. Non limiting examples of inert supports are silica or silicates, alumina or aluminates, aluminosilicates, titania or titanates, zirconia or zirconates, carbons (such as activated carbon, diamond, graphite, or fullerenes), sulfates, phosphates, tantalates, ceria, other metal oxides, and mixtures thereof. In the context of the reactions expressly described herein, in one embodiment of the present invention, the inert support consists essentially of silicon oxide ($SiO_2$). In another embodiment of the present invention, said silicon oxide is selected from the group consisting of amorphous silica, quartz, tridymite, cristobalite, moganite, coesite, and mixtures thereof. In another embodiment of the present invention, said silicon oxide is amorphous silica. In another embodiment of the present invention, said silicon oxide has a specific surface area of less than about 10 m²/g. When present, the inert support represents an amount of about 20 wt % to about 90 wt %, based on the total weight of the dehydration catalyst.

Alternative catalysts comprising: a) one or more anions selected from the group consisting of non-phosphorus-containing anions, heteropolyanions, and phosphate adducts, and b) one or more monovalent cations, wherein the catalyst is neutrally charged, can be utilized for dehydrating hydroxypropionic acid, hydroxypropionic acid derivatives, or mixtures thereof to acrylic acid, acrylic acid derivatives, or mixtures thereof. Non limiting examples of non-phosphorus-containing anions are arsenates, condensed arsenates, nitrates, sulfates, condensed sulfates, borates, carbonates, chromates, condensed chromates, vanadates, niobates, tantalates, selenates, condensed silicates, condensed aluminates, germanates, condensed germanates, molybdates, condensed molybdates, and other monomeric oxyanions or polyoxyanions that may be apparent to those having ordinary skill in the art. Non limiting examples of heteropolyanions are heteropolyphosphates, such as arsenatophosphates, phosphoaluminates, phosphoborates, phosphochromates, phosphomolybdates, phosphosilicates, phosphosulfates, phosphotungstates, and others that may be apparent to those having ordinary skill in the art. Non limiting examples of phosphate adducts are adducts of phosphate anions with telluric acid, halides, borates, carbonates, nitrates, sulfates, chromates, silicates, oxalates, mixtures thereof, or others that may be apparent to those having ordinary skill in the art.

III. Catalyst Preparation Methods

In one embodiment of the present invention, the method of preparing the dehydration catalyst comprises contacting: (a) a dehydration catalyst precursor mixture comprising one or more precursor phosphate salts; wherein said one or more precursor phosphate salts consist essentially of: i) one or more cations, and ii) one or more phosphate anions selected from the group represented by molecular formulae (IV) and (V):

(IV)

(V);

wherein y is any integer equal to or greater than 1 and z is any integer equal to or greater than 3; wherein said one or more precursor phosphate salts are neutrally charged; with (b) a gas mixture comprising water vapor; wherein the water partial pressure in said gas mixture is equal to or greater than the water partial pressure at the triple point of at least one of said one or more precursor phosphate salts; wherein said contacting step between said dehydration catalyst precursor mixture and said gas mixture is performed at a temperature equal to or greater than the temperature at the triple point of at least one of said one or more precursor phosphate salts; wherein one or more amorphous phosphate salts are produced as a result of said one or more precursor phosphate salts being contacted with said water vapor. In another embodiment of the present invention, said one or more cations are selected from the group consisting of monovalent cations, polyvalent cations, and mixtures thereof. In yet another embodiment of the present invention, said one or more cations are selected from the group consisting of monovalent cations.

In one embodiment of the present invention, the method of preparing the dehydration catalyst comprises contacting: (a) a dehydration catalyst precursor mixture comprising one or more precursor phosphate salts; wherein said one or more precursor phosphate salts consist essentially of: i) one or more monovalent cations, and ii) one or more phosphate anions selected from the group represented by molecular formulae (IV) and (V):

(IV)

(V);

wherein y is any integer equal to or greater than 1 and z is any integer equal to or greater than 3; wherein said one or more precursor phosphate salts are neutrally charged; with (b) a gas mixture comprising water vapor; wherein the water partial pressure in said gas mixture is equal to or greater than the water partial pressure at the triple point of at least one of said one or more precursor phosphate salts; wherein said contacting step between said dehydration catalyst precursor mixture and said gas mixture is performed at a temperature equal to or greater than the temperature at the triple point of at least one of said one or more precursor phosphate salts; wherein one or more amorphous phosphate salts are produced as a result of said one or more precursor phosphate salts being contacted with said water vapor. In the context of the present invention, the anion represented by molecular formula (V) can refer either to the anion of cyclophosphate salts or to the anion of long-chain linear polyphosphate salts as described in "Phosphoric Acids and Phosphates, Kirk-Othmer Encyclopedia of Chemical Technology" by David R. Gard (published online: 15 Jul. 2005) and "Phosphorus: Chemistry, Biochemistry and Technology" by D. E. C. Corbridge (2013). When the molecular formula (V) refers to the anion of long chain polyphosphate salts, the molecular formula is not precise in that it does not include the minor perturbation of excess negative charge owing to the two end-group oxygens.

Figure 2:
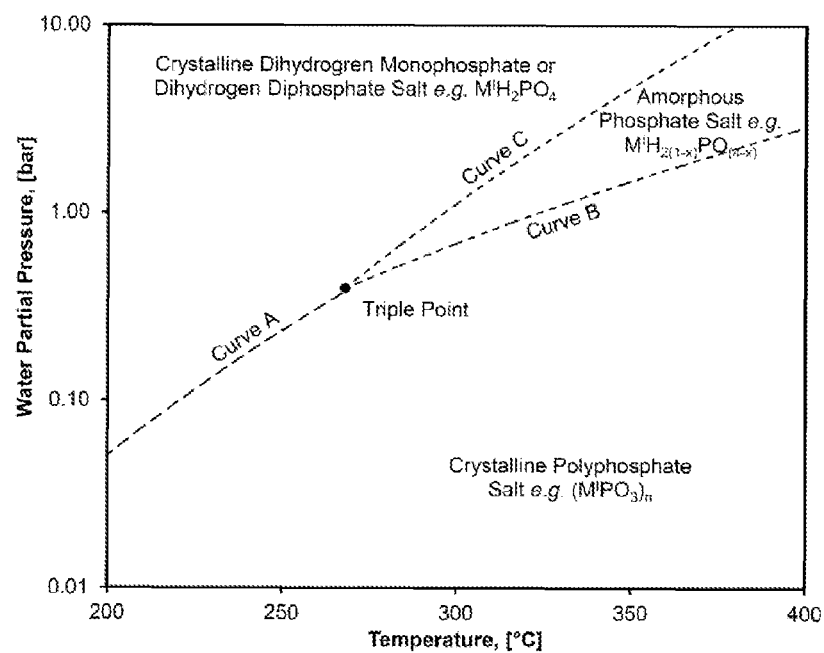
FIG. 2 illustrates a typical water partial pressure versus temperature phase equilibrium diagram of a dehydration catalyst (amorphous phosphate salt) and its precursor phosphate salts (crystalline phosphate salts). The triple point is located in the interception of the three phase boundary curves. $M^I$ is a monovalent cation. The reported values of water partial pressure are only an illustration and do not represent the real values for every specific dehydration catalyst described in the current invention.

In the context of the present invention, the triple point is the temperature and water partial pressure at which three phases: crystalline dihydrogen monophosphate or dihydrogen diphosphate salt, crystalline polyphosphate salt, and amorphous phosphate salt coexist in thermodynamic equilibrium. By way of example, and not limitation, the triple point can be located by determining the interception of two (out of three) phase boundary curves in the water partial pressure versus temperature phase equilibrium diagram (see FIG. 2):

Curve A: phase boundary between i) crystalline dihydrogen monophosphate or crystalline dihydrogen diphosphate salt and ii) crystalline polyphosphate salt, at low temperatures and water partial pressures (e.g. below about 248° C. and 0.85 bar for potassium salts, below about 267° C. and 0.35 bar for cesium salts);

Curve B: phase boundary between i) crystalline polyphosphate salt and ii) amorphous phosphate salt at high temperatures and medium water partial pressures (e.g. above about 248° C. and 0.85 bar for potassium salts, above about 267° C. and 0.35 bar for cesium salts); and Curve C: phase boundary between i) crystalline dihydrogen monophosphate or crystalline dihydrogen diphosphate salt and ii) amorphous phosphate salt at high temperatures and high water partial pressures.

The phase boundary curves can be determined by any method known to those skilled in the art, such as, by way of example and not limitation, in-situ x-ray diffraction (XRD), thermal analysis (e.g. thermogravimetric analysis, differential thermal analysis, and differential scanning calorimetry), Raman spectroscopy, infrared spectroscopy (IR), nuclear magnetic resonance (NMR) spectroscopy, or the methods described in Taninouchi, Y.-k., et al., *J. Electrochem. Soc.* 156:B572-B579 (2009); or Ikeda, A. and Haile, S. M., *Solid State Ionics* 2012, 213:63-71 (2012) (all incorporated herein by reference). As an illustration, in a method based on the in-situ XRD technique, a precursor phosphate salt is contacted at high temperature (e.g. 450° C.) with a gas stream consisting of an inert gas (e.g. nitrogen, helium, or air) and water vapor at a specific water partial pressure until equilibrium is achieved. Then, the temperature is gradually decreased while monitoring changes on x-ray diffraction patterns, until a phase transition is observed. The same procedure is repeated at different water partial pressures and the transition temperatures are recorded. The water partial pressures (in logarithmic scale) are plotted against the transition temperatures (in linear scale) and fitted to the Arrhenius equation ($\log_{10}(P_{H_2O})=A+B/T$). Finally, the triple point is calculated by determining the interception point between the two phase boundary curves (i.e. curve A and curve B in FIG. 2).

In one embodiment of the present invention, the temperature during said contacting step between said dehydration catalyst precursor mixture and said gas mixture is equal to or greater than the temperature at the triple point of at least one of said one or more precursor phosphate salts. In another embodiment of the present invention, the temperature during said contacting step between said dehydration catalyst precursor mixture and said gas mixture is equal to or greater than the lowest triple point temperature of said one or more precursor phosphate salts. In another embodiment of the present invention, the temperature during said contacting step between said dehydration catalyst precursor mixture and said gas mixture is equal to or greater than the highest triple point temperature of said one or more precursor phosphate salts. In another embodiment of the present invention, the temperature during said contacting step between said dehydration catalyst precursor mixture and said gas mixture is equal to or greater than the average temperature between the lowest triple point temperature and the highest triple point temperature of said one or more precursor phosphate salts. In another embodiment of the present invention, the temperature during said contacting step between said dehydration catalyst precursor mixture and said gas mixture is at least 10° C. greater than the temperature at the triple point of at least one of said one or more precursor phosphate salts. In another embodiment of the present invention, the temperature during said contacting step between said dehydration catalyst precursor mixture and said gas mixture is at least 50° C. greater than the temperature at the triple point of at least one of said one or more precursor phosphate salts. In another embodiment of the present invention, the temperature during said contacting step between said dehydration catalyst precursor mixture and said gas mixture is at least 100° C. greater than the temperature at the triple point of at least one of said one or more precursor phosphate salts.

In one embodiment of the present invention, the water partial pressure in said gas mixture is equal to or greater than the water partial pressure at the triple point of at least one of said one or more precursor phosphate salts. In another embodiment of the present invention, the water partial pressure in said gas mixture is equal to or greater than the lowest triple point water partial pressure of said one or more precursor phosphate salts. In another embodiment of the present invention, the water partial pressure in said gas mixture is equal to or greater than the highest triple point water partial pressure of said one or more precursor phosphate salts. In another embodiment of the present invention, the water partial pressure in said gas mixture is equal to or greater than the average water partial pressure between the lowest triple point water partial pressure and the highest triple point water partial pressure of said one or more precursor phosphate salts. In one embodiment of the present invention, the water partial pressure in said gas mixture is at least 1 bar greater than the water partial pressure at the triple point of at least one of said one or more precursor phosphate salts. In one embodiment of the present invention, the water partial pressure in said gas mixture is at least 2 bar greater than the water partial pressure at the triple point of at least one of said one or more precursor phosphate salts. In one embodiment of the present invention, the water partial pressure in said gas mixture is at least 5 bar greater than the water partial pressure at the triple point of at least one of said one or more precursor phosphate salts.

In one embodiment of the present invention, the method of preparing the dehydration catalyst comprises contacting: (a) a dehydration catalyst precursor mixture comprising one or more precursor phosphate salts; wherein said one or more precursor phosphate salts consist essentially of: i) one or more monovalent cations, and ii) one or more phosphate anions selected from the group represented by molecular formulae (IV) and (V):

$$[H_2P_yO_{(3y+1)}]^{y-} \quad (IV)$$

$$[PO_3]_z^{z-} \quad (V);$$

wherein y is any integer equal to or greater than 1 and z is any integer equal to or greater than 3; wherein said one or more precursor phosphate salts are neutrally charged; with (b) a gas mixture comprising water vapor at a partial pressure equal to or greater than about 4 bar; wherein said contacting step between said dehydration catalyst precursor mixture and said gas mixture is performed at a temperature equal to or greater than about 250° C.; wherein one or more amorphous phosphate salts are produced as a result of said one or more precursor phosphate salts being contacted with said water vapor.

In another embodiment of the present invention, the method of preparing the dehydration catalyst comprises contacting: (a) a dehydration catalyst precursor mixture comprising one or more precursor phosphate salts; wherein said one or more precursor phosphate salts consist essentially of: i) one or more monovalent cations selected from the group consisting of Na⁺, K⁺, Rb⁺, Cs⁺, and mixtures thereof; and ii) one or more phosphate anions selected from the group represented by molecular formulae (IV) and (V):

$$[H_2P_yO_{(3y+1)}]^{y-} \quad (IV)$$

$$[PO_3]_z^{z-} \quad (V);$$

wherein y is any integer equal to or greater than 1 and z is any integer equal to or greater than 3; wherein said one or more precursor phosphate salts are neutrally charged; with (b) a gas mixture comprising water vapor at a partial pressure equal to or greater than about 0.8 bar; wherein said contacting step between said dehydration catalyst precursor mixture and said gas mixture is performed at a temperature equal to or greater than about 250° C.; wherein one or more amorphous phosphate salts are produced as a result of said one or more precursor phosphate salts being contacted with said water vapor.

In one embodiment of the present invention, the method of preparing the dehydration catalyst comprises contacting: (a) a dehydration catalyst precursor mixture comprising one or more precursor phosphate salts and one or more non-phosphate compounds; wherein said one or more non-phosphate compounds are substantially chemically inert to said one or more precursor phosphate salts; wherein said one or more precursor phosphate salts consist essentially of: i) one or more cations, and ii) one or more phosphate anions selected from the group represented by molecular formulae (IV) and (V):

$$[H_2P_yO_{(3y+1)}]^{p-} \quad (IV)$$

$$[PO_3]_z^{z-} \quad (V);$$

wherein y is any integer equal to or greater than 1 and z is any integer equal to or greater than 3; wherein said one or more precursor phosphate salts are neutrally charged; with (b) a gas mixture comprising water vapor; wherein the water partial pressure in said gas mixture is equal to or greater than the water partial pressure at the triple point of at least one of said one or more precursor phosphate salts; wherein said contacting step between said dehydration catalyst precursor mixture and said gas mixture is performed at a temperature equal to or greater than the temperature at the triple point of at least one of said one or more precursor phosphate salts; wherein one or more amorphous phosphate salts are produced as a result of said one or more precursor phosphate salts being contacted with said water vapor. In another embodiment of the present invention, said one or more cations are selected from the group consisting of monovalent cations, polyvalent cations, and mixtures thereof. In yet another embodiment of the present invention, said one or more cations are selected from the group consisting of monovalent cations.

In one embodiment of the present invention, the method of preparing the dehydration catalyst comprises contacting: (a) a dehydration catalyst precursor mixture comprising one or more precursor phosphate salts and one or more non-phosphate compounds; wherein said one or more non-phosphate compounds are substantially chemically inert to said one or more precursor phosphate salts; wherein said one or more precursor phosphate salts consist essentially of: i) one or more monovalent cations, and ii) one or more phosphate anions selected from the group represented by molecular formulae (IV) and (V):

$$[H_2P_yO_{(3y+1)}]^{p-} \quad (IV)$$

$$[PO_3]_z^{z-} \quad (V);$$

wherein y is any integer equal to or greater than 1 and z is any integer equal to or greater than 3; wherein said one or more precursor phosphate salts are neutrally charged; with (b) a gas mixture comprising water vapor; wherein the water partial pressure in said gas mixture is equal to or greater than the water partial pressure at the triple point of at least one of said one or more precursor phosphate salts; wherein said contacting step between said dehydration catalyst precursor mixture and said gas mixture is performed at a temperature equal to or greater than the temperature at the triple point of at least one of said one or more precursor phosphate salts; wherein one or more amorphous phosphate salts are produced as a result of said one or more precursor phosphate salts being contacted with said water vapor. In another embodiment of the present invention, said one or more non-phosphate compounds are essentially chemically inert to said one or more precursor phosphate salts. In yet another embodiment of the present invention, said one or more non-phosphate compounds are chemically inert to said one or more precursor phosphate salts.

In one embodiment of the present invention, the method of preparing the dehydration catalyst comprises contacting: (a) a dehydration catalyst precursor mixture comprising one or more precursor phosphate salts and one or more non-phosphate compounds; wherein said one or more non-phosphate compounds are substantially chemically inert to said one or more precursor phosphate salts; wherein said one or more precursor phosphate salts consist essentially of: i) one or more monovalent cations, and ii) one or more phosphate anions selected from the group represented by molecular formulae (IV) and (V):

$$[H_2P_yO_{(3y+1)}]^{p-} \quad (IV)$$

$$[PO_3]_z^{z-} \quad (V);$$

wherein y is any integer equal to or greater than 1 and z is any integer equal to or greater than 3; wherein said one or more precursor phosphate salts are neutrally charged; with (b) a gas mixture comprising water vapor; wherein the water partial pressure in said gas mixture is equal to or greater than about 4 bar; wherein said contacting step between said dehydration catalyst precursor mixture and said gas mixture is performed at a temperature equal to or greater than about 250° C.; wherein one or more amorphous phosphate salts are produced as a result of said one or more precursor phosphate salts being contacted with said water vapor. In another embodiment of the present invention, said one or more non-phosphate compounds are essentially chemically inert to said one or more precursor phosphate salts. In yet another embodiment of the present invention, said one or more non-phosphate compounds are chemically inert to said one or more precursor phosphate salts.

In another embodiment of the present invention, the method of preparing the dehydration catalyst comprises contacting:
(a) a dehydration catalyst precursor mixture comprising one or more precursor phosphate salts and one or more non-phosphate compounds; wherein said one or more non-phosphate compounds are substantially chemically inert to said one or more precursor phosphate salts; wherein said one or more precursor phosphate salts consist essentially of: i) one or more monovalent cations selected from the group consisting of Na$^+$, K$^+$, Rb$^+$, Cs$^+$, and mixtures thereof, and ii) one or more phosphate anions selected from the group represented by molecular formulae (IV) and (V):

$$[H_2P_yO_{(3y+1)}]^{p-} \quad (IV)$$

$$[PO_3]_z^{z-} \quad (V);$$

wherein y is any integer equal to or greater than 1 and z is any integer equal to or greater than 3; wherein said one or more precursor phosphate salts are neutrally charged; with (b) a gas mixture comprising water vapor; wherein the water partial pressure in said gas mixture is equal to or greater than about 0.8 bar; wherein said contacting step between said dehydration catalyst precursor mixture and said gas mixture is performed at a temperature equal to or greater than about 250° C.; wherein one or more amorphous phosphate salts are produced as a result of said one or more precursor phosphate salts being contacted with said water vapor. In another embodiment of the present invention, said one or more non-phosphate compounds are essentially chemically inert to said one or more precursor phosphate salts. In yet another embodiment of the present invention, said one or more non-phosphate compounds are chemically inert to said one or more precursor phosphate salts.

In one embodiment of the present invention, the weight ratio between the total amount of said one or more precursor phosphate salts and the total amount of said one or more non-phosphate compounds in said dehydration catalyst precursor mixture is between about 1:10 and about 4:1.

In the context of the present invention, "one or more cations" refers to different types of cations and "one or more anions" refers to different types of anions. Non limiting examples of cations are metallic cations, organo-metallic cations, ammonium, substituted ammonium, oxycations, and other cations known by those skilled in the art. Non limiting examples of substituted ammonium and other cations are isopropylammonium, ethylenediammonium, sarcosinium, L-histidinium, glycinium, and 4-aminopyridinium. Non limiting examples of oxycations are pervanadyl and vanadyl ions.

Non limiting examples of monovalent cations of said one or more precursor phosphate salts are cations of alkali metals, organo-metallic cations, ammonium, substituted ammonium, oxycations (e.g. pervanadyl), and other cations known by those skilled in the art. In one embodiment of the present invention, said one or more monovalent cations of said one or more precursor phosphate salts are selected from the group consisting of $Li^+$, $Na^+$, $K^+$, $Rb^+$, $Cs^+$, $Ag^+$, $Tl^+$, and mixtures thereof. In another embodiment of the present invention, said one or more monovalent cations of said one or more precursor phosphate salts are selected from the group consisting of $Na^+$, $K^+$, $Rb^+$, $Cs^+$, and mixtures thereof. In yet another embodiment of the present invention, said one or more monovalent cations is $K^+$.

In another embodiment of the present invention, at least one of said one or more precursor phosphate salts consists of two or more different monovalent cations selected from the group consisting of $Li^+$, $Na^+$, $K^+$, $Rb^+$, $Cs^+$, $Ag^+$, and $Tl^+$. In another embodiment of the present invention, at least one of said one or more precursor phosphate salts consists of two or more different monovalent cations selected from the group consisting of $Na^+$, $K^+$, $Rb^+$, and $Cs^+$.

In one embodiment of the present invention, said one or more phosphate anions of said one or more precursor phosphate salts are selected from the group represented by molecular formulae (IVa), (IVb), (IVc), (IVd), (Va), (Vb), (Vc) and mixtures thereof:

  (IVa)

  (IVb)

  (IVc)

  (IVd)

  (Va)

  (Vb)

  (Vc);

wherein n is any integer equal to or greater than 3. In the context of the present invention, the anion represented by molecular formula (Vc) can refer either to the anion of cyclophosphate salts or to the anion of long-chain linear polyphosphate salts as described in "Phosphoric Acids and Phosphates, Kirk-Othmer Encyclopedia of Chemical Technology" by David R. Gard (published online: 15 Jul. 2005) and "Phosphorus: Chemistry, Biochemistry and Technology" by D. E. C. Corbridge (2013). When the molecular formula (Vc) refers to the anion of long chain polyphosphate salts, the molecular formula is not precise in that it does not include the minor perturbation of excess negative charge owing to the two end-group oxygens.

Non limiting examples of precursor phosphate salts are dihydrogen monophosphates, dihydrogen diphosphates, dihydrogen triphosphates, dihydrogen tetraphosphates, tricyclophosphates, tetracyclophosphates, pentacyclophosphates, hexacyclophosphates, octacyclophosphates, decacyclophosphates, and linear polyphosphates of alkali metals or mixed alkali metals. In one embodiment of the present invention, said one or more precursor phosphate salts are selected from the group consisting of $LiH_2PO_4$, $Li_2H_2P_2O_7$, $Li_3P_3O_9$, $Li_4P_4O_{12}$, $Li_6P_6O_{18}$, $LiP_8O_{24}$, $(LiPO_3)_n$, $NaH_2PO_4$, $Na_2H_2P_2O_7$, $Na_3H_2P_3O_{10}$, $Na_3P_3O_9$, $Na_5P_5O_{15}$, $Na_4P_4O_{12}$, $Na_6P_6O_{18}$, $Na_8P_8O_{24}$, $Na_{12}P_{12}O_{36}$, $(NaPO_3)_n$, $KH_2PO_4$, $K_2H_2P_2O_7$, $K_3H_2P_3O_{10}$, $K_4H_2P_4O_{13}$, $K_3P_3O_9$, $K_4P_4O_{12}$, $K_6P_6O_{18}$, $K_8P_8O_{24}$, $K_{10}P_{10}O_{30}$, $(KPO_3)_n$, $RbH_2PO_4$, $Rb_2H_2P_2O_7$, $Rb_3H_2P_3O_{10}$, $Rb_4H_2P_4O_{13}$, $Rb_3P_3O_9$, $Rb_4P_4O_{12}$, $Rb_6P_6O_{18}$, $Rb_8P_8O_{24}$, $(RbPO_3)_n$, $CsH_2PO_4$, $Cs_2H_2P_2O_7$, $Cs_3H_2P_3O_{10}$, $Cs_4H_2P_4O_{13}$, $Cs_3P_3O_9$, $Cs_4P_4O_{12}$, $Cs_6P_6O_{18}$, $Cs_8P_8O_{24}$, $(CsPO_3)_n$, $NaK_3(H_2P_2O_7)_2$, $LiK_2P_3O_9$, $LiNa_2P_3O_9$, $Na_2KP_3O_9$, $Na_2RbP_3O_9$, $Na_2CsP_3O_9$, $Na_3KP_4O_{12}$, $Na_2K_2P_4O_{12}$, $Na_2Rb_2P_4O_{12}$, $Na_3CsP_4O_{12}$, $Li_3Na_3P_6O_{18}$, $Li_3K_3P_6O_{18}$, $Li_2K_4P_6O_{18}$, $Li_3Na_3P_6O_{18}$, $Li_3K_3P_6O_{18}$, $Li_3Rb_3P_6O_{18}$, $Li_3Cs_3P_6O_{18}$, $Na_4Rb_2P_6O_{18}$, $Na_4Cs_2P_6O_{18}$, $LiNa_7P_8O_{24}$, $Na_6K_4P_{10}O_{30}$, $(LiK(PO_3)_2)_n$, $(LiRb(PO_3)_2)_n$, $(Li_2Rb(PO_3)_3)_n$, $(LiCs(PO_3)_2)_n$, $(Li_2Cs(PO_3)_3)_n$, any of their hydrated forms, and mixtures thereof. In another embodiment of the present invention, said one or more precursor phosphate salts are selected from the group consisting of $LiH_2PO_4$, $(LiPO_3)_n$, $NaH_2PO_4$, $(NaPO_3)_n$, $KH_2PO_4$, $(KPO_3)_n$, $RbH_2PO_4$, $(RbPO_3)_n$, $CsH_2PO_4$, $(CsPO_3)_n$, any of their hydrated forms, and mixtures thereof. In yet another embodiment of the present invention, said one or more precursor phosphate salts are selected from the group consisting of $KH_2PO_4$, $(KPO_3)_n$, any of their hydrated forms, and mixtures thereof. In the context of the present invention, the precursor phosphate salts represented by the formulae $(M^IPO_3)$, $(M^IN^I(PO_3)_2)_n$, or $(M^I_2N^I(PO_3)_3)_n$, wherein $M^I$ and $N^I$ are two different monovalent cations, can be either cyclophosphates or long-chain linear polyphosphates.

In one embodiment of the present invention, said one or more non-phosphate compounds comprise silicon oxide ($SiO_2$). In one embodiment of the present invention, said one or more non-phosphate compounds consists essentially of silicon oxide ($SiO_2$). In another embodiment of the present invention, said silicon oxide is selected from the group consisting of amorphous silica, quartz, tridymite, cristobalite, moganite, coesite, and mixtures thereof. In another embodiment of the present invention, said silicon oxide is amorphous silica. In yet another embodiment of the present invention, said silicon oxide has a specific surface area of less than about 10 $m^2/g$.

In another embodiment of the present invention, said one or more precursor phosphate salts are selected from the group consisting of $LiH_2PO_4$, $(LiPO_3)_n$, $NaH_2PO_4$, $(NaPO_3)_n$, $KH_2PO_4$, $(KPO_3)_n$, $RbH_2PO_4$, $(RbPO_3)_n$, $CsH_2PO_4$, $(CsPO_3)_n$, any of their hydrated forms, and mixtures thereof; and said one or more non-phosphate compounds are selected from the group consisting of amorphous silica, quartz, and mixtures thereof. In another embodiment of the present invention, said one or more precursor phosphate salts is $KH_2PO_4$ or $(KPO_3)_n$, and said one or more non-phosphate compounds is amorphous silica.

In one embodiment of the present invention, said one or more non-phosphate compounds comprise one or more oxysalts comprising: (a) one or more polyvalent cations, and (b) one or more oxyanions selected from the group represented by molecular formulae (II) and (III):

$$[H_{(a-2b)}S_cO_{(4c-b)}]^{(2c-a)-} \quad (II)$$

$$[Ta_{2d}O_{(5d+e)}]^{2e-} \quad (III);$$

wherein a and b are positive integers or zero; wherein c, d, and e are positive integers; wherein (a−2b) is equal to or greater than zero; wherein (2c−a) is greater than zero; wherein said one or more oxysalts are neutrally charged. In another embodiment of the present invention, said one or more non-phosphate compounds further comprise silicon oxide ($SiO_2$).

In another embodiment of the present invention, said one or more non-phosphate compounds comprise one or more oxysalts comprising: (a) one or more polyvalent cations, (b) one or more monovalent cations, and (c) one or more oxyanions selected from the group represented by molecular formulae (II) and (III):

$$[H_{(a-2b)}S_cO_{(4c-b)}]^{(2c-a)-} \quad (II)$$

$$[Ta_{2d}O_{(5d+e)}]^{2e-} \quad (III);$$

wherein a and b are positive integers or zero; wherein c, d, and e are positive integers; wherein (a−2b) is equal to or greater than zero; wherein (2c−a) is greater than zero; wherein said one or more oxysalts are neutrally charged. In another embodiment of the present invention, said one or more non-phosphate compounds further comprise silicon oxide ($SiO_2$).

Non limiting examples of said one or more polyvalent cations of said one or more oxysalts are cations of alkaline earth metals, transition metals, post-transition or poor metals, and metalloids; organo-metallic cations, substituted ammonium cations, oxycations (e.g. vanadyl), and other cations known by those skilled in the art. In one embodiment of the present invention, said one or more polyvalent cations of said one or more oxysalts are selected from the group consisting of the cations of the metals Be, Mg, Ca, Sr, Ba, Sc, Y, Ti, Zr, Hf, V, Nb, Ta, Cr, Mo, W, Mn, Re, Al, Ga, In, Tl, Si, Ge, Sn, Pb, Sb, Bi, La, Ce, Pr, Nd, Sm, Eu, Gd, Tb, Dy, Ho, Er, Tm, Yb, Lu, and mixtures thereof. In another embodiment of the present invention, said one or more polyvalent cations of said one or more oxysalts are selected from the group consisting of the cations of the metals Mg, Ca, Sr, Ba, Y, Mn, Al, Er, and mixtures thereof. In another embodiment of the present invention, said one or more polyvalent cations of said one or more oxysalts are selected from the group consisting of divalent cations, trivalent cations, tetravalent cations, pentavalent cations, and mixtures thereof. In another embodiment of the present invention, said one or more polyvalent cations of said one or more oxysalts are selected from the group consisting of $Be^{2+}$, $Mg^{2+}$, $Ca^{2+}$, $Sr^{2+}$, $Ba^{2+}$, $Sc^{3+}$, $Y^{3+}$, $Ti^{3+}$, $Ti^{4+}$, $Zr^{2+}$, $Zr^{4+}$, $Hf^{4+}$, $V^{3+}$, $V^{4+}$, $Nb^{3+}$, $Cr^{2+}$, $Cr^{3+}$, $Mo^{3+}$, $Mo^{4+}$, $Mn^{2+}$, $Mn^{3+}$, $Re^{4+}$, $Al^+$, $Ga^{3+}$, $In^{3+}$, $Si^{4+}$, $Ge^{4+}$, $Sn^{4+}$, $Pb^{4+}$, $Sb^{3+}$, $Sb^{5+}$, $Bi^{3+}$, $La^{3+}$, $Ce^{3+}$, $Ce^{4+}$, $Pr^{3+}$, $Nd^{3+}$, $Sm^{3+}$, $Eu^{3+}$, $Gd^{3+}$, $Tb^{3+}$, $Dy^{3+}$, $Ho^{3+}$, $Er^{3+}$, $Tm^{3+}$, $Yb^{3+}$, $Lu^{3+}$, and mixtures thereof. In another embodiment of the present invention, said one or more polyvalent cations of said one or more oxysalts are selected from the group consisting of $Mg^{2+}$, $Ca^{2+}$, $Sr^{2+}$, $Ba^{2+}$, $Y^{3+}$, $Mn^{2+}$, $Mn^{3+}$, $Al^{3+}$, $Er^{3+}$, and mixtures thereof. In yet another embodiment of the present invention, said one or more polyvalent of said one or more oxysalts cations is $Ba^{2+}$.

Non limiting examples of said one or more monovalent cations of said one or more oxysalts are cations of alkali metals. In one embodiment of the present invention, said one or more monovalent cations of said one or more oxysalts are selected from the group consisting of the cations of the metals Li, Na, K, Rb, Cs, Ag, Tl, and mixtures thereof; and said one or more polyvalent cations of said one or more oxysalts are selected from the group consisting of the cations of the metals Be, Mg, Ca, Sr, Ba, Sc, Y, Ti, Zr, Hf, V, Nb, Ta, Cr, Mo, W, Mn, Re, Al, Ga, In, Tl, Si, Ge, Sn, Pb, Sb, Bi, La, Ce, Pr, Nd, Sm, Eu, Gd, Tb, Dy, Ho, Er, Tm, Yb, Lu, and mixtures thereof. In another embodiment of the present invention, said one or more monovalent cations of said one or more oxysalts are selected from the group consisting of the cations of the metals K, Rb, Cs, and mixtures thereof; and said one or more polyvalent cations of said one or more oxysalts are selected from the group consisting of the cations of the metals Mg, Ca, Sr, Ba, Y, Mn, Al, Er, and mixtures thereof.

In another embodiment of the present invention, said one or more oxyanions of said one or more oxysalts are selected from the group represented by molecular formulae (IIa) to (IId), (IIIa) to (IIIg), and mixtures thereof:

$$[SO_4]^{2-} \quad (IIa)$$

$$[S_2O_7]^{2-} \quad (IIb)$$

$$[HSO_4]^{1-} \quad (IIc)$$

$$[SO_4]^{2-} \cdot [HSO_4]^- \quad (IId)$$

$$[Ta_2O_6]^{2-} \quad (IIIa)$$

$$[Ta_2O_7]^{4-} \quad (IIIb)$$

$$[Ta_2O_9]^{8-} \quad (IIIc)$$

$$[Ta_2O_{10}]^{10-} \quad (IIId)$$

$$[Ta_2O_{11}]^{12-} \quad (IIIe)$$

$$[Ta_4O_{11}]^{2-} \quad (IIIf)$$

$$[Ta_4O_{15}]^{10-} \quad (IIIg).$$

In another embodiment of the present invention, said one or more oxyanions of said one or more oxysalts are selected from the group represented by molecular formulae (IIa), (IIIa), and mixtures thereof:

$$[SO_4]^{2-} \quad (IIa)$$

$$[Ta_2O_6]^{2-} \quad (IIIa).$$

Non limiting examples of said one or more oxysalts are sulfates of alkaline-earth metals, tantalates of alkaline-earth metals, sulfates of mixed alkali and alkaline earth metals, and tantalates of mixed alkali and alkaline earth metals. In one embodiment of the present invention, said one or more oxysalts are selected from the group consisting of $CaSO_4$, $SrSO_4$, $BaSO_4$, $SrK_2(SO_4)_2$, $SrRb_2(SO_4)_2$, $Ca_2K_2(SO_4)_3$, $Ca_2Rb_2(SO_4)_3$, $Ca_2Cs_2(SO_4)_3$, $CaTa_4O_{11}$, $SrTa_4O_{11}$, $BaTa_4O_{11}$, $MgTa_2O_6$, $CaTa_2O_6$, $SrTa_2O_6$, $BaTa_2O_6$, $Mg_2Ta_2O_7$, $Ca_2Ta_2O_7$, $Sr_2Ta_2O_7$, $SrK_2Ta_2O_7$, $Ba_2Ta_2O_7$, $Ba_3Ta_2O_8$, $Mg_4Ta_2O_9$, $Ca_4Ta_2O_9$, $Sr_4Ta_2O_9$, $Ba_4Ta_2O_9$, $Ca_5Ta_2O_{10}$, $Ca_2KTa_3O_{10}$, $Ca_2RbTa_3O_{10}$, $Ca_2CsTa_3O_{10}$, $Sr_2KTa_3O_{10}$, $Sr_2RbTa_3O_{10}$, $Sr_2CsTa_3O_{10}$, $Mg_5Ta_4O_{15}$, $Sr_5Ta_4O_{15}$, $BaSTa_4O_{15}$, $Sr_2KTa_5O_{15}$, $Ba_2KTa_5O_{15}$, $Sr_6Ta_2O_{11}$, $Ba_6Ta_2O_{11}$, any of their hydrated forms, and mixtures thereof. In another embodiment of the present invention, said one or more oxysalts are selected from the group consisting of $CaSO_4$, $CaTa_2O_6$, $SrSO_4$, $SrTa_2O_6$, $BaSO_4$, $BaTa_2O_6$, any of their hydrated forms, and mixtures thereof. In yet another embodiment of the present invention, said one or more oxysalts are selected from the group consisting of $BaSO_4$, $BaTa_2O_6$, any of their hydrated forms, and mixtures thereof.

In one embodiment of the present invention, said one or more precursor phosphate salts are selected from the group consisting of $LiH_2PO_4$, $(LiPO_3)_n$, $NaH_2PO_4$, $(NaPO_3)_n$, $KH_2PO_4$, $(KPO_3)_n$, $RbH_2PO_4$, $(RbPO_3)_n$, $CsH_2PO_4$, $(CsPO_3)_n$, any of their hydrated forms, and mixtures thereof; and said one or more non-phosphate compounds are selected from the group consisting of $CaSO_4$, $CaTa_2O_6$, $SrSO_4$, $SrTa_2O_6$, $BaSO_4$, $BaTa_2O_6$, any of their hydrated forms, and mixtures thereof. In another example of the present invention, said one or more precursor phosphate salts is $KH_2PO_4$ or $(KPO_3)_n$ and said one or more non-phosphate compounds is $BaSO_4$.

In one embodiment of the present invention, the method of preparing the dehydration catalyst comprises:
(a) mixing two or more different phosphate precursor compounds selected from the group comprising:

$$M_j^I(H_{(2+i-j)}P_iO_{(3i+1)}) \quad \text{(VIa)}$$

$$(NH_4)_l(H_{(2+k-l)}P_kO_{(3k+1)}) \quad \text{(VIb)}$$

$$M_p^I(H_{(m-p)}(PO_3)_m) \quad \text{(VIc)}$$

$$(NH_4)r(H_{(q-r)}(PO_3)_q) \quad \text{(VId)}$$

$$M_u^I(H_{(t-u)}P_{(2s+t)}O_{(5s+3t)}) \quad \text{(VIe)}$$

$$(NH_4)_\alpha(H_{(w-\alpha)}P_{(2v+w)}O_{(5v+3w)}) \quad \text{(VIf)}$$

$$M_2^IO \quad \text{(VIg)}$$

$$M^IOH \quad \text{(VIh)}$$

$$M^INO_3 \quad \text{(VIi)}$$

$$M_2^ICO_3 \quad \text{(VIj)}$$

$$(H(CH_2)_\beta COO)M^I \quad \text{(VIk);}$$

to produce a dehydration catalyst precursor mixture; wherein $M^I$ is a monovalent cation; wherein said monovalent cation is selected from the group consisting of $Li^+$, $Na^+$, $K^+$, $Rb^+$, $Cs^+$, $Ag^+$, $Tl^+$, and mixtures thereof; wherein i, k, m, q, s, and v are integers greater than zero; wherein j, l, p, r, u, and α are real numbers equal to or greater than zero; wherein t, w, and β are integers equal to or greater than zero; wherein (2+i−j), (2+k−l), (m−p), (q−r), (t−u), and (w−α) are equal to or greater than zero; wherein the molar ratio between the total amount of phosphorus (P) and the total amount of said one or more monovalent cations ($M^I$) in said dehydration catalyst precursor mixture is about 1; and
(b) contacting said dehydration catalyst precursor mixture with a gas mixture comprising water vapor to produce one or more amorphous phosphate salts; wherein the water partial pressure in said gas mixture is equal to or greater than the water partial pressure at the triple point of at least one of said one or more amorphous phosphate salts; and wherein said contacting step between said dehydration catalyst precursor mixture and said gas mixture is performed at a temperature equal to or greater than the temperature at the triple point of at least one of said one or more amorphous phosphate salts.

In one embodiment of the present invention, the method of preparing the dehydration catalyst comprises:
(a) mixing two or more different phosphate precursor compounds selected from the group comprising:

$$M_j^I(H_{(2+i-j)}P_iO_{(3i+1)}) \quad \text{(VIa)}$$

$$(NH_4)_l(H_{(2+k-l)}P_kO_{(3k+1)}) \quad \text{(VIb)}$$

$$M_p^I(H_{(m-p)}(PO_3)_m) \quad \text{(VIc)}$$

$$(NH_4)_r(H_{(q-r)}(PO_3)_q) \quad \text{(VId)}$$

$$M_u^I(H_{(t-u)}P_{(2s+t)}O_{(5s+3t)}) \quad \text{(VIe)}$$

$$(NH_4)_\alpha(H_{(w-\alpha)}P_{(2v+w)}O_{(5v+3w)}) \quad \text{(VIf)}$$

$$M_2^IO \quad \text{(VIg)}$$

$$M^IOH \quad \text{(VIh)}$$

$$M^INO_3 \quad \text{(VIi)}$$

$$M_2^ICO_3 \quad \text{(VIj)}$$

$$(H(CH_2)_\beta COO)M^I \quad \text{(VIk);}$$

to produce a dehydration catalyst precursor mixture; wherein $M^I$ is a monovalent cation; wherein said monovalent cation is selected from the group consisting of $Li^+$, $Na^+$, $K^+$, $Rb^+$, $Cs^+$, $Ag^+$, $Tl^+$, and mixtures thereof; wherein i, k, m, q, s, and v are integers greater than zero; wherein j, l, p, r, u, and α are real numbers equal to or greater than zero; wherein t, w, and β are integers equal to or greater than zero; wherein (2+i−j), (2+k−l), (m−p), (q−r), (t−u), and (w−α) are equal to or greater than zero; wherein the ratio between the total molar amount of phosphorus (P) and the total molar amount of said one or more monovalent cations ($M^I$) in said dehydration catalyst precursor mixture is about 1; and
(b) contacting said dehydration catalyst precursor mixture with a gas mixture comprising water vapor at a partial pressure equal to or greater than about 4 bar; wherein said contacting step between said dehydration catalyst precursor mixture and said gas mixture is performed at a temperature equal to or greater than about 250° C.; wherein one or more amorphous phosphate salts are produced as a result of said dehydration catalyst precursor mixture being contacted with said water vapor.

In another embodiment of the present invention, the method of preparing the dehydration catalyst comprises:
(a) mixing two or more different phosphate precursor compounds selected from the group comprising:

$$M_j^I(H_{(2+i-j)}P_iO_{(3i+1)}) \quad \text{(VIa)}$$

$$(NH_4)_l(H_{(2+k-l)}P_kO_{(3k+1)}) \quad \text{(VIb)}$$

$$M_p^I(H_{(m-p)}(PO_3)_m) \quad \text{(VIc)}$$

$$(NH_4)_r(H_{(q-r)}(PO_3)_q) \quad \text{(VId)}$$

$$M_u^I(H_{(t-u)}P_{(2s+t)}O_{(5s+3t)}) \quad \text{(VIe)}$$

$$(NH_4)_\alpha(H_{(w-\alpha)}P_{(2v+w)}O_{(5v+3w)}) \quad \text{(VIf)}$$

$$M_2^IO \quad \text{(VIg)}$$

$$M^IOH \quad \text{(VIh)}$$

$M^INO_3$ (VIi)

$M^ICO_3$ (VIj)

$(H(CH_2)_\beta COO)M^I$ (VIk);

to produce a dehydration catalyst precursor mixture; wherein $M^I$ is a monovalent cation; wherein said monovalent cation is selected from the group consisting of Na+, K+, Rb+, Cs+, and mixtures thereof; wherein i, k, m, q, s, and v are integers greater than zero; wherein j, l, p, r, u, and α are real numbers equal to or greater than zero; wherein t, w, and β are integers equal to or greater than zero; wherein (2+i−j), (2+k−l), (m−p), (q−r), (t−u), and (w−α) are equal to or greater than zero; wherein the ratio between the total molar amount of phosphorus (P) and the total molar amount of said one or more monovalent cations ($M^I$) in said dehydration catalyst precursor mixture is about 1; and (b) contacting said dehydration catalyst precursor mixture with a gas mixture comprising water vapor at a partial pressure equal to or greater than about 0.8 bar; wherein said contacting step between said dehydration catalyst precursor mixture and said gas mixture is performed at a temperature equal to or greater than about 250° C.; wherein one or more amorphous phosphate salts are produced as a result of said dehydration catalyst precursor mixture being contacted with said water vapor.

In another embodiment of the present invention, said two or more different phosphate precursor compounds are selected form the group consisting of $H_3PO_4$, $(NH_4)H_2PO_4$, $(NH_4)_2HPO_4$, $(NH_4)_3PO_4$, $P_2O_5$, $Li_2HPO_4$, $Li_3PO_4$, $Li_4P_2O_7$, $Li_2O$, LiOH, $LiNO_3$, $Li_2CO_3$, $(CH_3COO)Li$, HCOOLi, $Na_2HPO_4$, $Na_3PO_4$, $Na_4P_2O_7$, $Na_2O$, NaOH, $NaNO_3$, $Na_2CO_3$, $(CH_3COO)Na$, HCOONa, $K_2HPO_4$, $K_3PO_4$, $K_4P_2O_7$, $K_2O$, KOH, $KNO_3$, $K_2CO_3$, $(CH_3COO)K$, HCOOK, $Rb_2HPO_4$, $Rb_3PO_4$, $Rb_4P_2O_7$, $Rb_2O$, RbOH, $RbNO_3$, $Rb_2CO_3$, $(CH_3COO)Rb$, HCOORb, $Cs_2HPO_4$, $Cs_3PO_4$, $Cs_4P_2O_7$, $Cs_2O$, CsOH, $CsNO_3$, $Cs_2CO_3$, $(CH_3COO)Cs$, HCOOCs, any of their hydrated forms, and mixtures thereof.

In another embodiment of the present invention, the method of preparing the dehydration catalyst further comprises mixing one or more non-phosphate compounds with said two or more different phosphate precursor compounds before said contacting step; wherein said one or more non-phosphate compounds are substantially chemically inert to said two or more different phosphate precursor compounds. In another embodiment of the present invention, said one or more non-phosphate compounds are essentially chemically inert to said two or more different phosphate precursor compounds. In another embodiment of the present invention, said one or more non-phosphate compounds are chemically inert to said two or more different phosphate precursor compounds. In another embodiment of the present invention, said one or more non-phosphate compounds comprise silicon oxide ($SiO_2$). In another embodiment of the present invention, said one or more non-phosphate compounds consists essentially of silicon oxide ($SiO_2$). In another embodiment of the present invention, said silicon oxide is selected from the group consisting of amorphous silica, quartz, tridymite, cristobalite, moganite, coesite, and mixtures thereof. In another embodiment of the present invention, said one or more non-phosphate compounds comprise one or more oxysalts comprising: (a) one or more polyvalent cations, and (b) one or more oxyanions selected from the group represented by molecular formulae (II) and (III):

$[H_{(a-2b)}S_cO_{(4c-b)}]^{(2c-a)-}$ (II)

$[Ta_{2d}O_{(5d+e)}]^{2e-}$ (III);

wherein a and b are positive integers or zero; wherein c, d, and e are positive integers; wherein (a−2b) is equal to or greater than zero; wherein (2c−a) is greater than zero; wherein said one or more oxysalts are neutrally charged.

In another embodiment of the present invention, said two or more different phosphate precursor compounds are selected form the group consisting of $H_3PO_4$, $(NH_4)H_2PO_4$, $(NH_4)_2HPO_4$, $(NH_4)_3PO_4$, $P_2O_5$, $Li_2HPO_4$, $Li_3PO_4$, $Li_4P_2O_7$, $Li_2O$, LiOH, $LiNO_3$, $Li_2CO_3$, $(CH_3COO)Li$, HCOOLi, $Na_2HPO_4$, $Na_3PO_4$, $Na_4P_2O_7$, $Na_2O$, NaOH, $NaNO_3$, $Na_2CO_3$, $(CH_3COO)Na$, HCOONa, $K_2HPO_4$, $K_3PO_4$, $K_4P_2O_7$, $K_2O$, KOH, $KNO_3$, $K_2CO_3$, $(CH_3COO)K$, HCOOK, $Rb_2HPO_4$, $Rb_3PO_4$, $Rb_4P_2O_7$, $Rb_2O$, RbOH, $RbNO_3$, $Rb_2CO_3$, $(CH_3COO)Rb$, HCOORb, $Cs_2HPO_4$, $Cs_3PO_4$, $Cs_4P_2O_7$, $Cs_2O$, CsOH, $CsNO_3$, $Cs_2CO_3$, $(CH_3COO)Cs$, HCOOCs, any of their hydrated forms, and mixtures thereof; and said one or more non-phosphate compounds are selected from the group consisting of amorphous silica, quartz, and mixtures thereof.

In another embodiment of the present invention, said two or more different phosphate precursor compounds are selected form the group consisting of $H_3PO_4$, $(NH_4)H_2PO_4$, $(NH_4)_2HPO_4$, $(NH_4)_3PO_4$, $P_2O_5$, $Li_2HPO_4$, $Li_3PO_4$, $Li_4P_2O_7$, $Li_2O$, LiOH, $LiNO_3$, $Li_2CO_3$, $(CH_3COO)Li$, HCOOLi, $Na_2HPO_4$, $Na_3PO_4$, $Na_4P_2O_7$, $Na_2O$, NaOH, $NaNO_3$, $Na_2CO_3$, $(CH_3COO)Na$, HCOONa, $K_2HPO_4$, $K_3PO_4$, $K_4P_2O_7$, $K_2O$, KOH, $KNO_3$, $K_2CO_3$, $(CH_3COO)K$, HCOOK, $Rb_2HPO_4$, $Rb_3PO_4$, $Rb_4P_2O_7$, $Rb_2O$, RbOH, $RbNO_3$, $Rb_2CO_3$, $(CH_3COO)Rb$, HCOORb, $Cs_2HPO_4$, $Cs_3PO_4$, $Cs_4P_2O_7$, $Cs_2O$, CsOH, $CsNO_3$, $Cs_2CO_3$, $(CH_3COO)Cs$, HCOOCs, any of their hydrated forms, and mixtures thereof; and said one or more non-phosphate compounds are selected from the group consisting of $CaSO_4$, $CaTa_2O_6$, $SrSO_4$, $SrTa_2O_6$, $BaSO_4$, $BaTa_2O_6$, any of their hydrated forms, and mixtures thereof.

In one embodiment of the present invention, at least one of said one or more precursor phosphate salts of said dehydration catalyst precursor mixture is a hydrated salt. In another embodiment of the present invention, at least one of said one or more non-phosphate compounds of said dehydration catalyst precursor mixture is a hydrated compound. In another embodiment of the present invention, at least one of said one or more oxysalts of said dehydration catalyst precursor mixture is a hydrated salt. In another embodiment of the present invention, at least one of said two or more different phosphate precursor compounds of said dehydration catalyst precursor mixture is a hydrated compound. A hydrated salt or compound contains a specific number of water molecules per formula unit of the salt or compound. Non limiting examples of hydrated salts or compounds are hemihydrated, monohydrated, sesquihydrated, dehydrated, trihydrated, tetrahydrated, pentahydrated, hexahydrated, heptahydrated, octahydrated, nonahydrated, nonahydrated, and decahydrated salts or compounds.

In one embodiment of the present invention, the method of preparing the dehydration catalyst further comprises mixing one or more inert supports with said one or more precursor phosphate salts, said two or more different phosphate precursor compounds, or said dehydration catalyst precursor mixture before said contacting step with said gas mixture. In another embodiment of the present invention, said one or more non-phosphate compounds in said method of preparing the dehydration catalyst consist essentially of one or more inert supports. Non limiting examples of inert supports are silica or silicates, alumina or aluminates, aluminosilicates, titania or titanates, zirconia or zirconates, carbons (such as activated carbon, diamond, graphite, or fullerenes), phosphates, sulfates, tantalates, ceria, other metal oxides, and mixtures thereof. In the context of the reactions expressly described herein, in one embodiment of the present invention, said one or more inert supports comprise silicon oxide ($SiO_2$). In another embodiment of the present invention, said one or more inert supports consists essentially of silicon oxide ($SiO_2$). In another embodiment of the present invention, said silicon oxide is selected from the group consisting of amorphous silica, quartz, tridymite, cristobalite, moganite, coesite, and mixtures thereof. In another embodiment of the present invention, said silicon oxide is amorphous silica. In another embodiment of the present invention, said silicon oxide has a specific surface area of less than about 10 $m^2$/g.

The method of preparing the dehydration catalyst comprises contacting said dehydration catalyst precursor mixture with a gas mixture comprising water vapor. In one embodiment of the present invention, the water partial pressure in said gas mixture is equal to or greater than about 0.4 bar. In another embodiment of the present invention, the water partial pressure in said gas mixture is equal to or greater than about 0.8 bar. In another embodiment of the present invention, the water partial pressure in said gas mixture is equal to or greater than about 4 bar. In another embodiment of the present invention, the water partial pressure in said gas mixture is between about 5 bar and about 35 bar. In another embodiment of the present invention, said contacting step is performed under a total pressure equal to or greater than about 1 bar. In another embodiment of the present invention, said contacting step is performed under a total pressure equal to or greater than about 4 bar. In yet another embodiment of the present invention, said contacting step is performed under a total pressure between about 4 bar and about 35 bar.

In another embodiment of the present invention, said contacting step between said dehydration catalyst precursor mixture and said gas mixture is performed at a temperature equal to or greater than about 250° C. In another embodiment of the present invention, said contacting step between said dehydration catalyst precursor mixture and said gas mixture is performed at a temperature between about 300° C. and about 450° C.

The method of preparing the dehydration catalyst can comprise mixing of two or more different materials. This mixing step can be performed by any method known to those skilled in the art, such as, by way of example and not limitation: solid mixing, impregnation, or co-precipitation. In the solid mixing method, the various components are physically mixed together with optional grinding using any method known to those skilled in the art, such as, by way of example and not limitation, shear, extensional, kneading, extrusion, ball milling, and others, and alternatively followed by any additional treatment or activation step. In the impregnation method, a suspension of insoluble material (e.g. inert support) is treated with a solution of catalyst soluble ingredients, and the resulting material is then treated or activated under conditions that will convert the mixture to a more active or preferred state. In the co-precipitation method, a homogenous solution of the catalyst ingredients is precipitated by the addition of additional ingredients, followed by optional filtration and heating to remove solvents and volatile materials (e.g., water, nitric acid, carbon dioxide, ammonia, or acetic acid).

Mixing of catalyst components with surfactants followed by heating can increase catalyst surface area. In one embodiment of the present invention, the method of preparing the dehydration catalyst further comprises mixing one or more surfactants with said one or more precursor phosphate salts, said two or more different phosphate precursor compounds, or said dehydration catalyst precursor mixture before said contacting step with said gas mixture. In another embodiment of the present invention, said one or more surfactants are cationic or zwitterionic. Non limiting examples of surfactants are myristyltrimethylammonium bromide, hexadecyltrimethylammonium bromide, dodecyltrimethylammonium bromide, decyltrimethylammonium bromide, and octadecyltrimethyl ammonium bromide.

Heating can promote chemical reactions, thermal decompositions, phase transitions, and/or removal of volatile materials. In one embodiment of the present invention, the method of preparing the dehydration catalyst further comprises heating said one or more precursor phosphate salts, said two or more different phosphate precursor compounds, or said dehydration catalyst precursor mixture at a temperature equal to or greater than 180° C. before said contacting step with said gas mixture. In another embodiment of the present invention, the method of preparing the dehydration catalyst further comprises heating said one or more precursor phosphate salts, said two or more different phosphate precursor compounds, or said dehydration catalyst precursor mixture at a temperature equal to or greater than 300° C. before said contacting step with said gas mixture. In another embodiment of the present invention, the method of preparing the dehydration catalyst further comprises heating said one or more precursor phosphate salts, said two or more different phosphate precursor compounds, or said dehydration catalyst precursor mixture at a temperature between about 350° C. and about 650° C. before said contacting step with said gas mixture. In another embodiment of the present invention, the method of preparing the dehydration catalyst further comprises heating said one or more precursor phosphate salts, said two or more different phosphate precursor compounds, or said dehydration catalyst precursor mixture at a temperature between about 400° C. and about 450° C. before said contacting step with said gas mixture. Said heating step is typically done using any method known to those skilled in the art, such as, by way of example and not limitation, convection, conduction, radiation, microwave heating, and others. The heating step is performed with equipment such as, by way of example and not limitation, furnaces, atomizers, or reactors of various designs, comprising shaft furnaces, rotary kilns, hearth furnaces, fluidized bed reactors, spay dryers. The duration of said heating step is, in one embodiment of the present invention, about one hour to about seventy-two hours. In another embodiment, the duration of said heating step is between about two hours and about twelve hours. In yet another embodiment, the duration of said heating step is about four hours. In one embodiment, the temperature ramp in said heating step is between about 0.5° C./min and about 20° C./min. In another embodiment, the temperature ramp in said heating step is about 10° C./min.

In one embodiment of the present invention, the method of preparing the dehydration catalyst further comprises molding the particles of said one or more precursor phosphate salts, said two or more different phosphate precursor compounds, or said dehydration catalyst precursor mixture before said contacting step with said gas mixture. Non limiting examples of molding operations are granulation, agglomeration, compaction, pelleting, and extrusion. In another embodiment of the present invention, the method of preparing the dehydration catalyst further comprises size reduction or grinding of the particles of said one or more precursor phosphate salts, said two or more different phosphate precursor compounds, or said dehydration catalyst precursor mixture before said contacting step with said gas mixture. In one embodiment of the present invention, the method of preparing the dehydration catalyst further comprises sieving the particles of said one or more precursor phosphate salts, said two or more different phosphate precursor compounds, or said dehydration catalyst precursor mixture to select a material of specific size distribution before said contacting step with said gas mixture. In another embodiment of the present invention, the method of preparing the dehydration catalyst further comprises sieving the particles of said one or more precursor phosphate salts, said two or more different phosphate precursor compounds, or said dehydration catalyst precursor mixture to a median particle size of about 50 m to about 500 µm. In yet another embodiment of the present invention, the method of preparing the dehydration catalyst further comprises sieving the particles of said one or more precursor phosphate salts, said two or more different phosphate precursor compounds, or said dehydration catalyst precursor mixture to a median particle size of about 100 µm to about 200 µm.

In another embodiment, the dehydration catalyst is prepared by the following steps, which comprise: (a) mixing $KH_2PO_4$ and amorphous silica in a weight ratio between about 2:1 and about 1:8, to produce a dehydration catalyst precursor mixture, (b) heating said dehydration catalyst precursor mixture between about 200° C. and about 650° C. for about one hour to about twelve hours, to produce a calcined dehydration catalyst precursor mixture, (c) optionally grinding and sieving said calcined dehydration catalyst precursor mixture, to produce a ground dehydration catalyst precursor mixture, and (d) contacting said calcined dehydration catalyst precursor mixture or said ground dehydration catalyst precursor mixture with a gas mixture comprising nitrogen and water vapor; wherein the water partial pressure in said gas mixture is between about 5 bar and about 15 bar and wherein said contacting step is performed at a temperature between about 325° C. and about 425° C., to produce said dehydration catalyst.

In another embodiment, the dehydration catalyst is prepared by the following steps, which comprise: (a) mixing $KH_2PO_4$ and $BaSO_4$ in a weight ratio between about 2:1 and about 1:8, to produce a dehydration catalyst precursor mixture, (b) heating said dehydration catalyst precursor mixture between about 200° C. and about 650° C. for about one hour to about twelve hours, to produce a calcined dehydration catalyst precursor mixture, (c) optionally grinding and sieving said calcined dehydration catalyst precursor mixture, to produce a ground dehydration catalyst precursor mixture, and (d) contacting said calcined dehydration catalyst precursor mixture or said ground dehydration catalyst precursor mixture with a gas mixture comprising nitrogen and water vapor; wherein the water partial pressure in said gas mixture is between about 5 bar and about 15 bar and wherein said contacting step is performed at a temperature between about 325° C. and about 425° C., to produce said dehydration catalyst.

In another embodiment, the dehydration catalyst is prepared by the following steps, which comprise: (a) mixing $K_2HPO_4$, $(NH_4)_2HPO_4$, and amorphous silica in a weight ratio between about 1.3:1.0:16.1 and about 1.3:1.0:1.2, to produce a dehydration catalyst precursor mixture, (b) heating said dehydration catalyst precursor mixture between about 200° C. and about 650° C. for about one hour to about twelve hours, to produce a calcined precursor mixture, (c) optionally grinding and sieving said calcined dehydration catalyst precursor mixture, to produce a ground dehydration catalyst precursor mixture, and (d) contacting said calcined dehydration catalyst precursor mixture or said ground dehydration catalyst precursor mixture with a gas mixture comprising nitrogen and water vapor; wherein the water partial pressure in said gas mixture is between about 5 bar and about 15 bar and wherein said contacting step is performed at a temperature between about 325° C. and about 425° C., to produce said dehydration catalyst.

Following preparation, the catalyst can be utilized to catalyze several chemical reactions. Non limiting examples of reactions are: dehydration of lactic acid to acrylic acid (as described in further detail below); dehydration of 3-hydroxypropionic acid or 3-hydroxypropionic acid derivatives, or mixtures thereof to acrylic acid; dehydration of glycerin to acrolein; isomerization of lactic acid to 3-hydroxypropionic acid in the presence of water; reduction of hydroxypropionic acid to propionic acid or 1-propanol in the presence of hydrogen gas; dehydration of aliphatic alcohols to alkenes or olefins; dehydrogenation of aliphatic alcohols to ethers; other dehydrogenations, hydrolyses, alkylations, dealkylations, oxidations, disproportionations, esterifications, cyclizations, isomerizations, condensations, aromatizations, polymerizations; and other reactions that may be apparent to those having ordinary skill in the art.

IV. Methods of Producing Acrylic Acid, Acrylic Acid Derivatives, or Mixtures Thereof The inventors have unexpectedly found that the method of dehydrating hydroxypropionic acid, hydroxypropionic acid derivatives, or mixtures thereof can produce high yield to and selectivity of acrylic acid, acrylic acid derivatives, or mixtures thereof when the dehydration catalyst is prepared according to the present invention and the dehydration reaction is operated under a water partial pressure of more than about 0.4 bar. Not wishing to be bound by theory, the inventors believe that the elevated water partial pressure enhances the catalyst activity due to the formation (or preservation) of Brønsted acid sites from less protonated catalyst precursors. Thus, the inventors have also unexpectedly found that the process of dehydrating hydroxypropionic acid can be more efficient in the presence of elevated water partial pressure than under low water partial pressure or atmospheric conditions usually preferred in the art.

A method for dehydrating hydroxypropionic acid, hydroxypropionic acid derivatives, or mixtures thereof to acrylic acid, acrylic acid derivatives, or mixtures thereof is provided. In one embodiment of the present invention, said hydroxypropionic acid is selected from the group consisting of lactic acid (2-hydroxypropionic), 3-hydroxypropionic acid, and mixtures thereof; and said hydroxypropionic acid derivatives are selected from the group consisting of lactic acid derivatives, 3-hydroxypropionic acid derivatives, and mixtures thereof. In another embodiment of the present invention, said hydroxypropionic acid is lactic acid and said hydroxypropionic acid derivatives are lactic acid derivatives.

Lactic acid can be D-lactic acid, L-lactic acid, or mixture thereof. Lactic acid derivatives can be metal or ammonium salts of lactic acid, alkyl esters of lactic acid, lactic acid oligomers, cyclic di-esters of lactic acid, lactic acid anhydride, 2-alkoxypropionic acids or their alkyl esters, 2-aryloxypropionic acids or their alkyl esters, 2-acyloxypropionic acids or their alkyl esters, or a mixture thereof. Non limiting examples of metal salts of lactic acid are sodium lactate, potassium lactate, and calcium lactate. Non limiting examples of alkyl esters of lactic acid are methyl lactate, ethyl lactate, butyl lactate, 2-ethylhexyl lactate, and mixtures thereof. A non limiting example of cyclic di-esters of lactic acid is dilactide. Non limiting examples of 2-alkoxypropionic acids are 2-methoxypropionic acid and 2-ethoxypropionic acid. A non limiting example of 2-aryloxypropionic acid is 2-phenoxypropionic acid. A non limiting example of 2-acyloxypropionic acid is 2-acetoxypropionic acid. In one embodiment of the present invention, the lactic acid derivative is methyl lactate. Methyl lactate can be neat or in a solution with water, methanol, or mixtures thereof.

3-hydroxypropionic acid derivatives can be metal or ammonium salts of 3-hydroxypropionic acid, alkyl esters of 3-hydroxypropionic acid, 3-hydroxypropionic acid oligomers, 3-alkoxypropionic acids or their alkyl esters, 3-aryloxypropionic acids or their alkyl esters, 3-acyloxypropionic acids or their alkyl esters, or a mixture thereof. Non limiting examples of metal salts of 3-hydroxypropionic acid are sodium 3-hydroxypropionate, potassium 3-hydroxypropionate, and calcium 3-hydroxypropionate. Non limiting examples of alkyl esters of hydroxypropionic acid are methyl 3-hydroxypropionate, ethyl 3-hydroxypropionate, butyl 3-hydroxypropionate, 2-ethylhexyl 3-hydroxypropionate, and mixtures thereof. Non limiting examples of 3-alkoxypropionic acids are 3-methoxypropionic acid and 3-ethoxypropionic acid. A non limiting example of 3-aryloxypropionic acid is 3-phenoxypropionic acid. A non limiting example of 3-acyloxypropionic acid is 3-acetoxypropionic acid.

Acrylic acid derivatives can be metal or ammonium salts of acrylic acid, alkyl esters of acrylic acid, acrylic acid oligomers, or mixtures thereof. Non limiting examples of metal salts of acrylic acid are sodium acrylate, potassium acrylate, and calcium acrylate. Non limiting examples of alkyl esters of acrylic acid are methyl acrylate, ethyl acrylate, butyl acrylate, 2-ethylhexyl acrylate, or mixtures thereof.

In one embodiment of the present invention, a method of making acrylic acid, acrylic acid derivatives, or mixtures thereof comprises contacting: a) hydroxypropionic acid, hydroxypropionic acid derivatives, or mixtures thereof; b) water vapor; and c) any dehydration catalyst disclosed in Section II ("Catalysts for the Conversion of Hydroxypropionic Acid or its Derivatives to Acrylic Acid or its Derivatives") or any dehydration catalyst precursor mixture disclosed in Section III ("Catalyst Preparation Method") of the present invention; wherein the water partial pressure during said contacting step is equal to or greater than the water partial pressure at the triple point of at least one of said one or more amorphous phosphate salts or said one or more precursor phosphate salts in said dehydration catalyst or said dehydration catalyst precursor mixture; wherein said contacting step is performed at a temperature equal to or greater than the temperature at the triple point of at least one of said one or more amorphous phosphate salts or said one or more precursor phosphate salts in said dehydration catalyst or said dehydration catalyst precursor mixture; and whereby said acrylic acid, acrylic acid derivatives, or mixtures thereof is produced as a result of said water vapor and said hydroxypropionic acid, hydroxypropionic acid derivatives, or mixtures thereof being contacted with said dehydration catalyst or said dehydration catalyst precursor mixture. In another embodiment of the present invention, said hydroxypropionic acid, hydroxypropionic acid derivatives, or mixtures thereof in said method of making acrylic acid, acrylic acid derivatives, or mixtures thereof are lactic acid, lactic acid derivatives, or mixtures thereof.

In another embodiment of the present invention, a method of making acrylic acid, acrylic acid derivatives, or mixtures thereof comprises contacting: a) hydroxypropionic acid, hydroxypropionic acid derivatives, or mixtures thereof; b) water vapor; and c) any dehydration catalyst disclosed in Section II ("Catalysts for the Conversion of Hydroxypropionic Acid or its Derivatives to Acrylic Acid or its Derivatives") or any dehydration catalyst precursor mixture disclosed in Section III ("Catalyst Preparation Method") of the present invention; wherein the water partial pressure during said contacting step is equal to or greater than about 4 bar; wherein said contacting step is performed at a temperature equal to or greater than about 250° C.; and whereby said acrylic acid, acrylic acid derivatives, or mixtures thereof is produced as a result of said water vapor and said hydroxypropionic acid, hydroxypropionic acid derivatives, or mixtures thereof being contacted with said dehydration catalyst or said dehydration catalyst precursor mixture. In another embodiment of the present invention, said hydroxypropionic acid, hydroxypropionic acid derivatives, or mixtures thereof in said method of making acrylic acid, acrylic acid derivatives, or mixtures thereof are lactic acid, lactic acid derivatives, or mixtures thereof.

In another embodiment of the present invention, a method of making acrylic acid, acrylic acid derivatives, or mixtures thereof comprises contacting: a) hydroxypropionic acid, hydroxypropionic acid derivatives, or mixtures thereof; b) water vapor; and c) any dehydration catalyst disclosed in Section II ("Catalysts for the Conversion of Hydroxypropionic Acid or its Derivatives to Acrylic Acid or its Derivatives") or any dehydration catalyst precursor mixture disclosed in Section III ("Catalyst Preparation Method") of the present invention, wherein said one or more monovalent cations are selected from the group consisting of Na$^+$, K$^+$, Rb$^+$, Cs$^+$, and mixtures thereof; wherein the water partial pressure during said contacting step is equal to or greater than about 0.8 bar; wherein said contacting step is performed at a temperature equal to or greater than about 250° C.; and whereby said acrylic acid, acrylic acid derivatives, or mixtures thereof is produced as a result of said water vapor and said hydroxypropionic acid, hydroxypropionic acid derivatives, or mixtures thereof being contacted with said dehydration catalyst or said dehydration catalyst precursor mixture. In another embodiment of the present invention, said hydroxypropionic acid, hydroxypropionic acid derivatives, or mixtures thereof in said method of making acrylic acid, acrylic acid derivatives, or mixtures thereof are lactic acid, lactic acid derivatives, or mixtures thereof.

In one embodiment of the present invention, a method of making acrylic acid, acrylic acid derivatives, or mixtures thereof comprises contacting: a) hydroxypropionic acid, hydroxypropionic acid derivatives, or mixtures thereof; b) water vapor; c) an essentially chemically inert gas or essentially chemically inert liquid; and d) any dehydration catalyst disclosed in Section II ("Catalysts for the Conversion of Hydroxypropionic Acid or its Derivatives to Acrylic Acid or its Derivatives") or any dehydration catalyst precursor mixture disclosed in Section III ("Catalyst Preparation Method") of the present invention; wherein the water partial pressure during said contacting step is equal to or greater than the water partial pressure at the triple point of at least one of said one or more amorphous phosphate salts or said one or more precursor phosphate salts in said dehydration catalyst or said dehydration catalyst precursor mixture; wherein said contacting step is performed at a temperature equal to or greater than the temperature at the triple point of at least one of said one or more amorphous phosphate salts or said one or more precursor phosphate salts in said dehydration catalyst or said dehydration catalyst precursor mixture; and whereby said acrylic acid, acrylic acid derivatives, or mixtures thereof is produced as a result of said water vapor and said hydroxypropionic acid, hydroxypropionic acid derivatives, or mixtures thereof being contacted with said dehydration catalyst or said dehydration catalyst precursor mixture. In another embodiment of the present invention, said hydroxypropionic acid, hydroxypropionic acid derivatives, or mixtures thereof in said method of making acrylic acid, acrylic acid derivatives, or mixtures thereof are lactic acid, lactic acid derivatives, or mixtures thereof.

In another embodiment of the present invention, a method of making acrylic acid, acrylic acid derivatives, or mixtures thereof comprises contacting: a) hydroxypropionic acid, hydroxypropionic acid derivatives, or mixtures thereof; b) water vapor; c) an essentially chemically inert gas or essentially chemically inert liquid; and d) any dehydration catalyst disclosed in Section II ("Catalysts for the Conversion of Hydroxypropionic Acid or its Derivatives to Acrylic Acid or its Derivatives") or any dehydration catalyst precursor mixture disclosed in Section III ("Catalyst Preparation Method") of the present invention; wherein the water partial pressure during said contacting step is equal to or greater than about 4 bar; wherein said contacting step is performed at a temperature equal to or greater than about 250° C.; and whereby said acrylic acid, acrylic acid derivatives, or mixtures thereof is produced as a result of said water vapor and said hydroxypropionic acid, hydroxypropionic acid derivatives, or mixtures thereof being contacted with said dehydration catalyst or said dehydration catalyst precursor mixture. In another embodiment of the present invention, said hydroxypropionic acid, hydroxypropionic acid derivatives, or mixtures thereof in said method of making acrylic acid, acrylic acid derivatives, or mixtures thereof are lactic acid, lactic acid derivatives, or mixtures thereof.

In another embodiment of the present invention, a method of making acrylic acid, acrylic acid derivatives, or mixtures thereof comprises contacting: a) hydroxypropionic acid, hydroxypropionic acid derivatives, or mixtures thereof; b) water vapor; c) an essentially chemically inert gas or essentially chemically inert liquid; and d) any dehydration catalyst disclosed in Section II ("Catalysts for the Conversion of Hydroxypropionic Acid or its Derivatives to Acrylic Acid or its Derivatives") or any dehydration catalyst precursor mixture disclosed in Section III ("Catalyst Preparation Method") of the present invention, wherein said one or more monovalent cations are selected from the group consisting of Na+, $K^+$, $Rb^+$, $Cs^+$, and mixtures thereof; wherein the water partial pressure during said contacting step is equal to or greater than about 0.8 bar; wherein said contacting step is performed at a temperature equal to or greater than about 250° C.; and whereby said acrylic acid, acrylic acid derivatives, or mixtures thereof is produced as a result of said water vapor and said hydroxypropionic acid, hydroxypropionic acid derivatives, or mixtures thereof being contacted with said dehydration catalyst or said dehydration catalyst precursor mixture. In another embodiment of the present invention, said hydroxypropionic acid, hydroxypropionic acid derivatives, or mixtures thereof in said method of making acrylic acid, acrylic acid derivatives, or mixtures thereof are lactic acid, lactic acid derivatives, or mixtures thereof.

In one embodiment of the present invention, said hydroxypropionic acid, hydroxypropionic acid derivatives, or mixtures thereof are in the gas phase, at least partially, during said contacting step with said dehydration catalyst or said dehydration catalyst precursor mixture. In another embodiment of the present invention, said hydroxypropionic acid, hydroxypropionic acid derivatives, or mixtures thereof are in the liquid phase, at least partially, during said contacting step with said dehydration catalyst or said dehydration catalyst precursor mixture.

In one embodiment of the present invention, a method of making acrylic acid is provided. The method comprises contacting: (a) a gas mixture comprising: i) hydroxypropionic acid, hydroxypropionic acid derivatives, or mixtures thereof; and ii) water vapor; with (b) any dehydration catalyst disclosed in Section II ("Catalysts for the Conversion of Hydroxypropionic Acid or its Derivatives to Acrylic Acid or its Derivatives") or any dehydration catalyst precursor mixture disclosed in Section III ("Catalyst Preparation Method") of the present invention; wherein the water partial pressure during said contacting step in said gas mixture is equal to or greater than the water partial pressure at the triple point of at least one of said one or more amorphous phosphate salts or said one or more precursor phosphate salts in said dehydration catalyst or said dehydration catalyst precursor mixture; wherein said contacting step is performed at a temperature equal to or greater than the temperature at the triple point of at least one of said one or more amorphous phosphate salts or said one or more precursor phosphate salts in said dehydration catalyst or said dehydration catalyst precursor mixture; and whereby said acrylic acid, acrylic acid derivatives, or mixtures thereof is produced as a result of said water vapor and said hydroxypropionic acid, hydroxypropionic acid derivatives, or mixtures thereof being contacted with said dehydration catalyst or said dehydration catalyst precursor mixture. In another embodiment of the present invention, said hydroxypropionic acid, hydroxypropionic acid derivatives, or mixtures thereof in said method of making acrylic acid, acrylic acid derivatives, or mixtures thereof are lactic acid, lactic acid derivatives, or mixtures thereof.

In one embodiment of the present invention, a method of making acrylic acid is provided. The method comprises contacting: (a) a gas mixture comprising: i) hydroxypropionic acid, hydroxypropionic acid derivatives, or mixtures thereof; and ii) water vapor; with (b) any dehydration catalyst disclosed in Section II ("Catalysts for the Conversion of Hydroxypropionic Acid or its Derivatives to Acrylic Acid or its Derivatives") or any dehydration catalyst precursor mixture disclosed in Section III ("Catalyst Preparation Method") of the present invention; wherein the water partial pressure during said contacting step in said gas mixture is equal to or greater than about 4 bar; wherein said contacting step is performed at a temperature equal to or greater than about 250° C.; and whereby said acrylic acid, acrylic acid derivatives, or mixtures thereof is produced as a result of said water vapor and said hydroxypropionic acid, hydroxypropionic acid derivatives, or mixtures thereof being contacted with said dehydration catalyst or said dehydration catalyst precursor mixture. In another embodiment of the present invention, said hydroxypropionic acid, hydroxypropionic acid derivatives, or mixtures thereof in said method of making acrylic acid, acrylic acid derivatives, or mixtures thereof are lactic acid, lactic acid derivatives, or mixtures thereof.

In one embodiment of the present invention, a method of making acrylic acid, acrylic acid derivatives, or mixtures thereof comprises contacting: (a) a gas mixture comprising: i) hydroxypropionic acid, hydroxypropionic acid derivatives, or mixtures thereof; and ii) water vapor; with (b) any dehydration catalyst disclosed in Section II ("Catalysts for the Conversion of Hydroxypropionic Acid or its Derivatives to Acrylic Acid or its Derivatives") or any dehydration catalyst precursor mixture disclosed in Section III ("Catalyst Preparation Method") of the present invention, wherein said one or more monovalent cations are selected from the group consisting of $Na^+$, $K^+$, $Rb^+$, $Cs^+$, and mixtures thereof; wherein the water partial pressure during said contacting step in said gas mixture is equal to or greater than about 0.8 bar; wherein said contacting step is performed at a temperature equal to or greater than about 250° C.; and whereby said acrylic acid, acrylic acid derivatives, or mixtures thereof is produced as a result of said water vapor and said hydroxypropionic acid, hydroxypropionic acid derivatives, or mixtures thereof being contacted with said dehydration catalyst or said dehydration catalyst precursor mixture. In another embodiment of the present invention, said hydroxypropionic acid, hydroxypropionic acid derivatives, or mixtures thereof in said method of making acrylic acid, acrylic acid derivatives, or mixtures thereof are lactic acid, lactic acid derivatives, or mixtures thereof.

In one embodiment of the present invention, a method of making acrylic acid, acrylic acid derivatives, or mixtures thereof comprises contacting: (a) a liquid mixture comprising hydroxypropionic acid, hydroxypropionic acid derivatives, or mixtures thereof; and (b) a gas mixture comprising water vapor; with (c) any dehydration catalyst disclosed in Section II ("Catalysts for the Conversion of Hydroxypropionic Acid or its Derivatives to Acrylic Acid or its Derivatives") or any dehydration catalyst precursor mixture disclosed in Section III ("Catalyst Preparation Method") of the present invention; wherein the water partial pressure during said contacting step in said gas mixture is equal to or greater than the water partial pressure at the triple point of at least one of said one or more amorphous phosphate salts or said one or more precursor phosphate salts in said dehydration catalyst or said dehydration catalyst precursor mixture; wherein said contacting step is performed at a temperature equal to or greater than the temperature at the triple point of at least one of said one or more amorphous phosphate salts or said one or more precursor phosphate salts in said dehydration catalyst or said dehydration catalyst precursor mixture; and whereby said acrylic acid, acrylic acid derivatives, or mixtures thereof is produced as a result of said water vapor and said hydroxypropionic acid, hydroxypropionic acid derivatives, or mixtures thereof being contacted with said dehydration catalyst or said dehydration catalyst precursor mixture. In another embodiment of the present invention, said hydroxypropionic acid, hydroxypropionic acid derivatives, or mixtures thereof in said method of making acrylic acid, acrylic acid derivatives, or mixtures thereof are lactic acid, lactic acid derivatives, or mixtures thereof.

In one embodiment of the present invention, a method of making acrylic acid, acrylic acid derivatives, or mixtures thereof comprises contacting: (a) a liquid mixture comprising hydroxypropionic acid, hydroxypropionic acid derivatives, or mixtures thereof; and (b) a gas mixture comprising water vapor; with (c) any dehydration catalyst disclosed in Section II ("Catalysts for the Conversion of Hydroxypropionic Acid or its Derivatives to Acrylic Acid or its Derivatives") or any dehydration catalyst precursor mixture disclosed in Section III ("Catalyst Preparation Method") of the present invention; wherein the water partial pressure during said contacting step in said gas mixture is equal to or greater than about 4 bar; wherein said contacting step is performed at a temperature equal to or greater than about 250° C.; and whereby said acrylic acid, acrylic acid derivatives, or mixtures thereof is produced as a result of said water vapor and said hydroxypropionic acid, hydroxypropionic acid derivatives, or mixtures thereof being contacted with said dehydration catalyst or said dehydration catalyst precursor mixture. In another embodiment of the present invention, said hydroxypropionic acid, hydroxypropionic acid derivatives, or mixtures thereof in said method of making acrylic acid, acrylic acid derivatives, or mixtures thereof are lactic acid, lactic acid derivatives, or mixtures thereof.

In one embodiment of the present invention, a method of making acrylic acid, acrylic acid derivatives, or mixtures thereof comprises contacting: (a) a liquid mixture comprising hydroxypropionic acid, hydroxypropionic acid derivatives, or mixtures thereof; and (b) a gas mixture comprising water vapor; with (c) any dehydration catalyst disclosed in Section II ("Catalysts for the Conversion of Hydroxypropionic Acid or its Derivatives to Acrylic Acid or its Derivatives") or any dehydration catalyst precursor mixture disclosed in Section III ("Catalyst Preparation Method") of the present invention, wherein said one or more monovalent cations are selected from the group consisting of $Na^+$, $K^+$, $Rb^+$, $Cs^+$, and mixtures thereof; wherein the water partial pressure during said contacting step in said gas mixture is equal to or greater than about 0.8 bar; wherein said contacting step is performed at a temperature equal to or greater than about 250° C.; and whereby said acrylic acid, acrylic acid derivatives, or mixtures thereof is produced as a result of said water vapor and said hydroxypropionic acid, hydroxypropionic acid derivatives, or mixtures thereof being contacted with said dehydration catalyst or said dehydration catalyst precursor mixture. In another embodiment of the present invention, said hydroxypropionic acid, hydroxypropionic acid derivatives, or mixtures thereof in said method of making acrylic acid, acrylic acid derivatives, or mixtures thereof are lactic acid, lactic acid derivatives, or mixtures thereof.

In another embodiment of the present invention, said gas mixture further comprises an essentially chemically inert gas. In the context of the present invention, an essentially chemically inert gas is any gas that is essentially chemically inert to said hydroxypropionic acid, hydroxypropionic acid derivatives, or mixtures thereof, but not necessarily to said dehydration catalyst or said dehydration catalyst precursor mixture. Non limiting examples of essentially chemically inert gases are nitrogen, helium, argon, carbon dioxide, carbon monoxide, air, water vapor, and mixtures thereof. In another embodiment of the present invention, said essentially chemically inert gas comprises nitrogen. In yet another embodiment of the present invention, said essentially chemically inert gas consists essentially of nitrogen.

In another embodiment, said liquid mixture comprising hydroxypropionic acid, hydroxypropionic acid derivatives, or mixtures thereof can further comprise one or more essentially chemically inert liquids. Non limiting examples of essentially chemically inert liquids are water, hydrocarbons, chlorinated hydrocarbons, fluorinated hydrocarbons, brominated hydrocarbons, esters, ethers, ketones, aldehydes, acids, alcohols, or mixtures thereof. Non limiting examples of hydrocarbons are C5 to C8 linear and branched alkanes. A non limiting example of esters is ethyl acetate. A non limiting example of ethers is diphenyl ether. A non limiting example of ketones is acetone. Non limiting examples of alcohols are methanol, ethanol, and C3 to C8 linear and branched alcohols. In one embodiment of the present invention, said one or more essentially chemically inert liquids comprise water. In one embodiment of the present invention, said one or more essentially chemically inert liquids consists essentially of water.

In one embodiment of the present invention, a liquid mixture comprising hydroxypropionic acid, hydroxypropionic acid derivatives, or mixtures thereof is fed into an evaporator upstream of the catalytic reactor for the liquid mixture to become a gas mixture, at least partially, before contacting said dehydration catalyst or said dehydration catalyst precursor mixture. In another embodiment of the present invention, a liquid mixture comprising hydroxypropionic acid, hydroxypropionic acid derivatives, or mixtures thereof is fed directly into the catalytic reactor and contacted with said dehydration catalyst or said dehydration catalyst precursor mixture. In another embodiment of the present invention, an essentially chemically inert gas or an essentially chemically inert liquid is fed into the evaporator or into the catalytic reactor. The liquid mixture comprising hydroxypropionic acid, hydroxypropionic acid derivatives, or mixtures thereof and the essentially chemically inert gas or the essentially chemically inert liquid can be jointly or separately fed into said evaporator or said catalytic reactor. Non limiting examples of essentially chemically inert gases are nitrogen, helium, air, argon, carbon dioxide, carbon monoxide, water vapor, and mixtures thereof. Non limiting examples of essentially chemically inert liquids are water, hydrocarbons, chlorinated hydrocarbons, fluorinated hydrocarbons, brominated hydrocarbons, esters, ethers, ketones, aldehydes, acids, alcohols, or mixtures thereof.

In one embodiment of the present invention, a method of making acrylic acid, acrylic acid derivatives, or mixtures thereof comprises: a) providing a liquid mixture comprising hydroxypropionic acid, hydroxypropionic acid derivatives, or mixtures thereof; b) optionally combining said liquid mixture with an essentially chemically inert gas to form a liquid/gas blend; and c) contacting said liquid mixture or said liquid/gas blend with any dehydration catalyst disclosed in Section II ("Catalysts for the Conversion of Hydroxypropionic Acid or its Derivatives to Acrylic Acid or its Derivatives") or any dehydration catalyst precursor mixture disclosed in Section III ("Catalyst Preparation Method") under a water partial pressure of about 0.4 bar or more to produce an acrylic acid mixture comprising said acrylic acid, acrylic acid derivatives, or mixtures thereof.

In one embodiment of the present invention, a method of making acrylic acid, acrylic acid derivatives, or mixtures thereof comprises: a) providing a liquid mixture comprising an aqueous solution of hydroxypropionic acid, hydroxypropionic acid derivatives, or mixtures thereof; b) optionally combining said liquid mixture with an essentially chemically inert gas to form a liquid/gas blend; and c) contacting said liquid mixture or said liquid/gas blend with any dehydration catalyst disclosed in Section II ("Catalysts for the Conversion of Hydroxypropionic Acid or its Derivatives to Acrylic Acid or its Derivatives") or any dehydration catalyst precursor mixture disclosed in Section III ("Catalyst Preparation Method") under a water partial pressure of about 0.4 bar or more to produce an acrylic acid mixture comprising said acrylic acid, acrylic acid derivatives, or mixtures thereof.

In one embodiment of the present invention, a method of making acrylic acid, acrylic acid derivatives, or mixtures thereof comprises: a) providing a liquid mixture comprising an aqueous solution of hydroxypropionic acid, hydroxypropionic acid derivatives, or mixtures thereof; b) optionally combining said liquid mixture with an essentially chemically inert gas to form a liquid/gas blend; c) evaporating said liquid mixture or said liquid/gas blend to produce a gas mixture; and d) contacting said gas mixture with any dehydration catalyst disclosed in Section II ("Catalysts for the Conversion of Hydroxypropionic Acid or its Derivatives to Acrylic Acid or its Derivatives") or any dehydration catalyst precursor mixture disclosed in Section III ("Catalyst Preparation Method") under a water partial pressure of about 0.4 bar or more to produce an acrylic acid mixture comprising said acrylic acid, acrylic acid derivatives, or mixtures thereof.

In one embodiment of the present invention, a method of making acrylic acid, acrylic acid derivatives, or mixtures thereof comprises: a) providing a liquid mixture comprising an aqueous solution of hydroxypropionic acid, hydroxypropionic acid derivatives, or mixtures thereof, wherein the hydroxypropionic acid is essentially in monomeric form in the aqueous solution; b) optionally combining said liquid mixture with an essentially chemically inert gas to form a liquid/gas blend; c) evaporating said liquid mixture or said liquid/gas blend to produce a gas mixture; and d) contacting said gas mixture with any dehydration catalyst disclosed in Section II ("Catalysts for the Conversion of Hydroxypropionic Acid or its Derivatives to Acrylic Acid or its Derivatives") or any dehydration catalyst precursor mixture disclosed in Section III ("Catalyst Preparation Method") under a water partial pressure of about 0.4 bar or more to produce an acrylic acid mixture comprising said acrylic acid, acrylic acid derivatives, or mixtures thereof.

In another embodiment of the present invention, a method of making acrylic acid, acrylic acid derivatives, or mixtures thereof comprises: a) providing a liquid mixture comprising an aqueous solution of hydroxypropionic acid, hydroxypropionic acid derivatives, or mixtures thereof, wherein the hydroxypropionic acid is essentially in monomeric form in the aqueous solution, and wherein the hydroxypropionic acid, hydroxypropionic acid derivatives, or mixtures thereof comprise between about 10 wt % and about 25 wt % of the aqueous solution; b) optionally combining said liquid mixture with an essentially chemically inert gas to form a liquid/gas blend; c) evaporating said liquid mixture or said liquid/gas blend to produce a gas mixture; and d) contacting said gas mixture with any dehydration catalyst disclosed in Section II ("Catalysts for the Conversion of Hydroxypropionic Acid or its Derivatives to Acrylic Acid or its Derivatives") or any dehydration catalyst precursor mixture disclosed in Section III ("Catalyst Preparation Method") under a water partial pressure of about 0.4 bar or more to produce an acrylic acid mixture comprising said acrylic acid, acrylic acid derivatives, or mixtures thereof.

In another embodiment of the present invention, a method of making acrylic acid, acrylic acid derivatives, or mixtures thereof comprises: a) providing a liquid mixture comprising an aqueous solution of hydroxypropionic acid, hydroxypropionic acid derivatives, or mixtures thereof, wherein the hydroxypropionic acid comprises oligomers in the aqueous solution; b) heating said liquid mixture at a temperature between about 50° C. and about 100° C. to hydrolyze the oligomers of the hydroxypropionic acid and produce a liquid mixture comprising monomeric hydroxypropionic acid; c) optionally combining said liquid mixture comprising monomeric hydroxypropionic acid with an essentially chemically inert gas to form a liquid/gas blend; d) evaporating said liquid mixture comprising monomeric hydroxypropionic acid or said liquid/gas blend to produce a gas mixture; and e) contacting said gas mixture with any dehydration catalyst disclosed in Section II ("Catalysts for the Conversion of Hydroxypropionic Acid or its Derivatives to Acrylic Acid or its Derivatives") or any dehydration catalyst precursor mixture disclosed in Section III ("Catalyst Preparation Method") under a water partial pressure of about 0.4 bar or more to produce an acrylic acid mixture comprising said acrylic acid, acrylic acid derivatives, or mixtures thereof.

In another embodiment of the present invention, a method of making acrylic acid, acrylic acid derivatives, or mixtures thereof comprises: a) providing a liquid mixture comprising an aqueous solution of hydroxypropionic acid, hydroxypropionic acid derivatives, or mixtures thereof; b) optionally combining the liquid mixture with an essentially chemically inert gas to form a liquid/gas blend; c) evaporating said liquid mixture or said liquid/gas blend to produce a gas mixture; d) contacting said gas mixture with any dehydration catalyst disclosed in Section II ("Catalysts for the Conversion of Hydroxypropionic Acid or its Derivatives to Acrylic Acid or its Derivatives") or any dehydration catalyst precursor mixture disclosed in Section III ("Catalyst Preparation Method") under a water partial pressure of about 0.4 bar or more to produce an acrylic acid mixture comprising acrylic acid, acrylic acid derivatives, or mixtures thereof; and e) cooling said acrylic acid mixture to produce a liquid acrylic acid composition comprising acrylic acid, acrylic acid derivatives, or mixtures thereof.

In one embodiment of the present invention, the concentration of the hydroxypropionic acid, hydroxypropionic acid derivatives, or mixtures thereof in said liquid mixture is between about 2 wt % and about 95 wt %. In another embodiment of the present invention, the concentration of the hydroxypropionic acid, hydroxypropionic acid derivatives, or mixtures thereof in said liquid mixture is between about 5 wt % and about 60 wt %. In another embodiment of the present invention, the concentration of the hydroxypropionic acid, hydroxypropionic acid derivatives, or mixtures thereof in said liquid mixture is between about 10 wt % and about 40 wt %. In yet another embodiment of the present invention, the concentration of the hydroxypropionic acid, hydroxypropionic acid derivatives, or mixtures thereof in said liquid mixture is about 20 wt %.

In one embodiment of the present invention, the liquid mixture comprises an aqueous solution of hydroxypropionic acid, hydroxypropionic acid derivatives, or mixtures thereof. In another embodiment of the present invention, the liquid mixture comprises an aqueous solution of lactic acid, lactic acid derivatives, or mixtures thereof. In another embodiment of the present invention, said lactic acid derivatives in said aqueous solution are selected from the group consisting of metal or ammonium salts of lactic acid, alkyl esters of lactic acid, lactic acid oligomers, cyclic di-esters of lactic acid, lactic acid anhydride, 2-alkoxypropionic acids or their alkyl esters, 2-aryloxypropionic acids or their alkyl esters, 2-acyloxypropionic acids or their alkyl esters, or a mixture thereof.

In one embodiment of the present invention, the concentration of the lactic acid, lactic acid derivatives, or mixtures thereof in said aqueous solution is between about 2 wt % and about 95 wt %. In another embodiment of the present invention, the concentration of the lactic acid, lactic acid derivatives, or mixtures thereof in said aqueous solution is between about 5 wt % and about 60 wt %. In another embodiment of the present invention, the concentration of the lactic acid, lactic acid derivatives, or mixtures thereof in said aqueous solution is between about 10 wt % and about 40 wt %. In another embodiment of the present invention, the concentration of the lactic acid, lactic acid derivatives, or mixtures thereof in said aqueous solution is about 20 wt %. In another embodiment of the present invention, the liquid mixture comprises an aqueous solution of lactic acid along with lactic acid derivatives. In another embodiment of the present invention, the liquid mixture comprises less than about 30 wt % of lactic acid derivatives, based on the total weight of the liquid mixture. In another embodiment of the present invention, the liquid mixture comprises less than about 10 wt % of lactic acid derivatives, based on the total weight of the liquid mixture. In yet another embodiment of the present invention, the liquid mixture comprises less than about 5 wt % of lactic acid derivatives, based on the total weight of the liquid mixture.

Lactic acid can be in monomeric form or as oligomers in said aqueous solution of lactic acid, lactic acid derivatives, or mixtures thereof. In one embodiment of the present invention, the oligomers of the lactic acid in said aqueous solution of lactic acid, lactic acid derivatives, or mixtures thereof are less than about 30 wt % based on the total amount of lactic acid, lactic acid derivatives, or mixtures thereof. In another embodiment of the present invention, the oligomers of the lactic acid in said aqueous solution of lactic acid, lactic acid derivatives, or mixtures thereof are less than about 10 wt % based on the total amount of lactic acid, lactic acid derivatives, or mixtures thereof. In another embodiment of the present invention, the oligomers of the lactic acid in said aqueous solution of lactic acid, lactic acid derivatives, or mixtures thereof are less than about 5 wt % based on the total amount of lactic acid, lactic acid derivatives, or mixtures thereof. In yet another embodiment of the present invention, the lactic acid is essentially in monomeric form in said aqueous solution of lactic acid, lactic acid derivatives, or mixtures thereof.

The process to remove the oligomers from the aqueous solution of lactic acid, lactic acid derivatives, and mixtures thereof can comprise a purification step or hydrolysis by heating step. In one embodiment of the present invention, the heating step can involve heating the aqueous solution of lactic acid, lactic acid derivatives, or mixtures thereof at a temperature between about 50° C. and about 100° C. to hydrolyze the oligomers of the lactic acid. In another embodiment of the present invention, the heating step can involve heating the aqueous solution of lactic acid, lactic acid derivatives, or mixtures thereof at a temperature between about 95° C. and about 100° C. to hydrolyze the oligomers of the lactic acid. In another embodiment of the present invention, the heating step can involve heating the aqueous solution of lactic acid, lactic acid derivatives, or mixtures thereof at a temperature between about 50° C. and about 100° C. to hydrolyze the oligomers of the lactic acid and produce a monomeric lactic acid aqueous solution comprising at least 80 wt % of lactic acid in monomeric form based on the total amount of lactic acid, lactic acid derivatives, or mixtures thereof. In another embodiment of the present invention, the heating step can involve heating the aqueous solution of lactic acid, lactic acid derivatives, or mixtures thereof at a temperature between about 50° C. and about 100° C. to hydrolyze the oligomers of the lactic acid and produce a monomeric lactic acid aqueous solution comprising at least 95 wt % of lactic acid in monomeric form based on the total amount of lactic acid, lactic acid derivatives, or mixtures thereof. In another embodiment of the present invention, an about 88 wt % aqueous solution of lactic acid, lactic acid derivatives, or mixtures thereof is diluted with water and the oligomers are hydrolyzed to produce an aqueous solution of about 20 wt % lactic acid. The lactic acid oligomers can result in loss of acrylic acid selectivity due to their high boiling point. As the water content decreases in the aqueous solution, the loss of feed material to the catalyst reaction, due to losses in the evaporating step, increases. Additionally, lactic acid oligomers can cause coking, catalyst deactivation, and reactor plugging.

In another embodiment of the present invention, the liquid mixture comprising hydroxypropionic acid, hydroxypropionic acid derivatives, or mixtures thereof can further comprise one or more antioxidants. In another embodiment of the present invention, the liquid mixture comprising hydroxypropionic acid, hydroxypropionic acid derivatives, or mixtures thereof further comprises butylated hydroxy toluene (BHT), butylated hydroxy anisole (BHA), or mixtures thereof. In yet another embodiment of the present invention, the liquid mixture comprising hydroxypropionic acid, hydroxypropionic acid derivatives, or mixtures thereof further comprises ethylene glycol, ethanedithiol, methanol, methanethiol, or mixtures thereof.

The liquid mixture can be introduced into the evaporator or into the catalytic reactor with a simple tube or through atomization nozzles. Non limiting examples of atomization nozzles comprise fan nozzles, pressure swirl atomizers, air blast atomizers, two-fluid atomizers, rotary atomizers, and supercritical carbon dioxide atomizers. In one embodiment of the present invention, the droplets of the aqueous solution are less than about 500 µm in diameter. In another embodiment of the present invention, the droplets of the aqueous solution are less than about 200 µm in diameter. In yet another embodiment of the present invention, the droplets of the aqueous solution are less than about 100 µm in diameter.

In the evaporating step, said liquid mixture or said liquid/gas blend are heated to produce a gas mixture. In one embodiment of the present invention, the temperature during the evaporating step is between about 165° C. and about 450° C. In another embodiment of the present invention, the temperature during the evaporating step is between about 200° C. and about 400° C. In another embodiment of the present invention, the temperature during the evaporating step is between about 250° C. and about 375° C. In one embodiment of the present invention, the residence time in the evaporator during said evaporating step is between about 0.5 s and about 10 s. In another embodiment of the present invention, the residence time in the evaporator during said evaporating step is between about 1 s and about 5 s.

The evaporating step can be performed under vacuum, at atmospheric pressure, or at higher than atmospheric pressure. In one embodiment of the present invention, the evaporating step is performed under a total pressure of at least about 1 bar. In another embodiment of the present invention, the evaporating step is performed under a total pressure between about 5 bar and about 40 bar. In yet another embodiment of the present invention, the evaporating step is performed under a pressure between about 10 bar and about 35 bar. In yet another embodiment of the present invention, the evaporating step is performed under a total pressure of about 25 bar.

The evaporating step can be performed in various types of evaporators, such as, but not limited to, atomizer, plate heat exchanger, empty flow reactor, and fixed bed flow reactor. The evaporating step can be performed in an evaporator with the liquid mixture flowing down, or flowing up, or flowing horizontally. In one embodiment of the present invention, the evaporating step is performed in an evaporator with the liquid flowing down. Also, the evaporating step can be done in a batch form.

In one embodiment of the present invention, the material of the evaporator interior surface is selected from the group consisting of amorphous silica, quartz, other silicon oxides, borosilicate glass, silicon, and mixtures thereof. In yet another embodiment of the present invention, the material of the evaporator interior surface is amorphous silica or borosilicate glass.

In one embodiment of the present invention, the evaporating and contacting steps are combined in a single step. In another embodiment of the present invention, the evaporating and contacting steps are performed sequentially in a single reactor. In yet another embodiment of the present invention, the evaporating and contacting steps are performed sequentially in a tandem reactor.

The gas mixture comprising hydroxypropionic acid, hydroxypropionic acid derivatives, or mixtures thereof or the liquid mixture comprising hydroxypropionic acid, hydroxypropionic acid derivatives, or mixtures thereof are converted to acrylic acid, acrylic acid derivatives, and mixture thereof by contacting said mixtures with a dehydration catalyst or a dehydration catalyst precursor mixture. The dehydration catalyst can be selected from the group comprising phosphates, sulfates, tantalates, metal oxides, aluminates, silicates, aluminosilicates (e.g., zeolites), arsenates, nitrates, vanadates, niobates, selenates, arsenatophosphates, phosphoaluminates, phosphoborates, phosphochromates, phosphomolybdates, phosphosilicates, phosphosulfates, phosphotungstates, and mixtures thereof, and others that may be apparent to those having ordinary skill in the art. The dehydration catalyst can contain one or more inert supports. Non limiting examples of inert supports are silica or silicates, alumina or aluminates, aluminosilicates, titania or titanates, zirconia or zirconates, carbons (such as activated carbon, diamond, graphite, or fullerenes), sulfates, phosphates, tantalates, ceria, other metal oxides, and mixtures thereof. In one embodiment of the present invention, the dehydration catalyst is any dehydration catalyst disclosed in Section II ("Catalysts for the Conversion of Hydroxypropionic Acid or its Derivatives to Acrylic Acid or its Derivatives") or any dehydration catalyst precursor mixture disclosed in Section III ("Catalyst Preparation Method").

In the context of the present invention, "contacting" refers to the action of bringing said hydroxypropionic acid, hydroxypropionic acid derivatives, or mixtures thereof in close proximity to the surface of said dehydration catalyst or dehydration catalyst precursor mixture. The hydroxypropionic acid, hydroxypropionic acid derivatives, or mixtures thereof must contact the surface of the dehydration catalyst or the dehydration catalyst precursor mixture at a rate that is slow enough for the dehydration reaction to occur, yet fast enough to avoid the degradation of hydroxypropionic acid, acrylic acid, or their derivatives to undesirable products at the temperature of said contacting step. Several parameters can be used to describe the rate of said contacting step, such as, by way of example and not limitation, WHSV, GHSV, LHSV, and weight velocity per unit of accessible catalyst surface area (WVSA) that can be calculated as the ratio of WHSV and the dehydration catalyst specific surface area (SA), (WVSA=WHSV/SA); with units: $g/m^2 \cdot h$; where g refer to g of Lactic Acid. A number of methods, based on the adsorption of an inert gas, can be used to determine the accessible surface area, including, but not limited to, the static volumetric and gravimetric methods and the dynamic method that are well-known by those skilled in the art.

In one embodiment of the present invention, the hydroxypropionic acid, hydroxypropionic acid derivatives, or mixtures thereof contact the dehydration catalyst or the dehydration catalyst precursor mixture at a WVSA between about $10^4$ g·m$^{-2}$·h$^{-1}$ and about $10^{-4}$ g·m$^{-2}$·h$^{-1}$. In another embodiment of the present invention, the hydroxypropionic acid, hydroxypropionic acid derivatives, or mixtures thereof contact the dehydration catalyst or the dehydration catalyst precursor mixture at a WVSA between about $10^2$ g·m$^{-2}$·h$^{-1}$ and about $10^{-2}$ g·m$^{-2}$·h$^{-1}$. In another embodiment of the present invention, the hydroxypropionic acid, hydroxypropionic acid derivatives, or mixtures thereof contact the dehydration catalyst or the dehydration catalyst precursor mixture at a WVSA between about 10 g·m$^{-2}$·h$^{-1}$ and about 0.1 g·m$^{-2}$·h$^{-1}$.

In one embodiment of the present invention, the hydroxypropionic acid, hydroxypropionic acid derivatives, or mixtures thereof contact the dehydration catalyst or the dehydration catalyst precursor mixture at a WHSV between about 0.02 h$^{-1}$ and about 10 h$^{-1}$. In another embodiment of the present invention, the hydroxypropionic acid, hydroxypropionic acid derivatives, or mixtures thereof contact the dehydration catalyst or the dehydration catalyst precursor mixture at a WHSV between about 0.2 h$^{-1}$ and about 1 h$^{-1}$. In another embodiment of the present invention, the hydroxypropionic acid, hydroxypropionic acid derivatives, or mixtures thereof contact the dehydration catalyst or the dehydration catalyst precursor mixture at a WHSV between about 0.4 h$^{-1}$ and about 0.7 h$^{-1}$. In another embodiment of the present invention, the hydroxypropionic acid, hydroxypropionic acid derivatives, or mixtures thereof contact the dehydration catalyst or the dehydration catalyst precursor mixture at a WHSV of about 0.5 h$^{-1}$.

When hydroxypropionic acid, hydroxypropionic acid derivatives, or mixtures thereof are in the gas phase during said contacting step with said dehydration catalyst or said dehydration catalyst precursor mixture, and in another embodiment of the present invention, the gas mixture comprising hydroxypropionic acid, hydroxypropionic acid derivatives, or mixtures thereof contacts the dehydration catalyst or the dehydration catalyst precursor mixture at a GHSV between about 720 h$^{-1}$ and about 36,000 h$^{-1}$. In another embodiment of the present invention, the gas mixture comprising hydroxypropionic acid, hydroxypropionic acid derivatives, or mixtures thereof contacts the dehydration catalyst or the dehydration catalyst precursor mixture at a GHSV between about 1,800 h$^{-1}$ and about 9,000 h$^{-1}$. In another embodiment of the present invention, the gas mixture comprising hydroxypropionic acid, hydroxypropionic acid derivatives, or mixtures thereof contacts the dehydration catalyst or the dehydration catalyst precursor mixture at a GHSV between about 3,600 h$^{-1}$ and about 6,000 h$^{-1}$. In another embodiment of the present invention, a gas mixture comprising hydroxypropionic acid, hydroxypropionic acid derivatives, or mixtures thereof contacts the dehydration catalyst or the dehydration catalyst precursor mixture at a GHSV of about 4,500 h$^{-1}$.

When hydroxypropionic acid, hydroxypropionic acid derivatives, or mixtures thereof are in the gas phase during said contacting step with said dehydration catalyst or said dehydration catalyst precursor mixture, and in one embodiment of the present invention, the concentration of hydroxypropionic acid, hydroxypropionic acid derivatives, or mixtures thereof before the dehydration reaction and based on the total moles in the gas mixture (calculated under STP conditions) is between about 0.5 mol % and about 50 mol %. In another embodiment of the present invention, the concentration of hydroxypropionic acid, hydroxypropionic acid derivatives, or mixtures thereof before the dehydration reaction and based on the total moles in the gas mixture (calculated under STP conditions) is between about 1 mol % and about 10 mol %. In another embodiment of the present invention, the concentration of hydroxypropionic acid, hydroxypropionic acid derivatives, or mixtures thereof before the dehydration reaction and based on the total moles in the gas mixture (calculated under STP conditions) is between about 1.5 mol % and about 3.5 mol %. In yet another embodiment of the present invention, the concentration of hydroxypropionic acid, hydroxypropionic acid derivatives, or mixtures thereof before the dehydration reaction and based on the total moles in the gas mixture (calculated under STP conditions) is about 2.5 mol %.

In one embodiment of the present invention, the temperature during said contacting step with the dehydration catalyst or the dehydration catalyst precursor mixture is greater than about 150° C. In another embodiment of the present invention, the temperature during said contacting step with the dehydration catalyst or the dehydration catalyst precursor mixture is greater than about 250° C. In another embodiment of the present invention, the temperature during said contacting step with the dehydration catalyst or the dehydration catalyst precursor mixture is between about 300° C. and about 500° C. In another embodiment of the present invention, the temperature during said contacting step with the dehydration catalyst or the dehydration catalyst precursor mixture is between about 325° C. and about 400° C. In yet another embodiment of the present invention, the temperature during said contacting step with the dehydration catalyst or the dehydration catalyst precursor mixture is between about 350° C. and about 375° C.

In one embodiment of the present invention, the temperature during said contacting step with the dehydration catalyst or the dehydration catalyst precursor mixture is equal to or greater than the temperature at the triple point of at least one of said one or more amorphous phosphate salts or said one or more precursor phosphate salts. In another embodiment of the present invention, the temperature during said contacting step with the dehydration catalyst or the dehydration catalyst precursor mixture is equal to or greater than the lowest triple point temperature of said one or more amorphous phosphate salts or said one or more precursor phosphate salts. In another embodiment of the present invention, the temperature during said contacting step with the dehydration catalyst or the dehydration catalyst precursor mixture is equal to or greater than the highest triple point temperature of said one or more amorphous phosphate salts or said one or more precursor phosphate salts. In another embodiment of the present invention, the temperature during said contacting step with the dehydration catalyst or the dehydration catalyst precursor mixture is equal to or greater than the average temperature between the lowest triple point temperature and the highest triple point temperature of said one or more amorphous phosphate salts or said one or more precursor phosphate salts. In another embodiment of the present invention, the temperature during said contacting step with the dehydration catalyst or the dehydration catalyst precursor mixture is at least 10° C. greater than the temperature at the triple point of at least one of said one or more amorphous phosphate salts or said one or more precursor phosphate salts. In another embodiment of the present invention, the temperature during said contacting step with the dehydration catalyst or the dehydration catalyst precursor mixture is at least 50° C. greater than the temperature at the triple point of at least one of said one or more amorphous phosphate salts or said one or more precursor phosphate salts. In another embodiment of the present invention, the temperature during said contacting step with the dehydration catalyst or the dehydration catalyst precursor mixture is at least 100° C. greater than the temperature at the triple point of at least one of said one or more amorphous phosphate salts or said one or more precursor phosphate salts.

In another embodiment of the present invention, said water partial pressure during said contacting step with the dehydration catalyst or the dehydration catalyst precursor mixture is equal to or greater than about 0.4 bar. In another embodiment of the present invention, said water partial pressure during said contacting step with the dehydration catalyst or the dehydration catalyst precursor mixture is equal to or greater than about 0.8 bar. In another embodiment of the present invention, said water partial pressure during said contacting step with the dehydration catalyst or the dehydration catalyst precursor mixture is equal to or greater than about 4 bar. In another embodiment of the present invention, said water partial pressure during said contacting step with the dehydration catalyst or the dehydration catalyst precursor mixture is between about 5 bar and about 35 bar.

In one embodiment of the present invention, the water partial pressure during said contacting step with the dehydration catalyst or the dehydration catalyst precursor mixture is equal to or greater than the water partial pressure at the triple point of at least one of said one or more amorphous phosphate salts or said one or more precursor phosphate salts. In another embodiment of the present invention, the water partial pressure during said contacting step with the dehydration catalyst or the dehydration catalyst precursor mixture is equal to or greater than the lowest triple point water partial pressure of said one or more amorphous phosphate salts or said one or more precursor phosphate salts. In another embodiment of the present invention, the water partial pressure during said contacting step with the dehydration catalyst or the dehydration catalyst precursor mixture is equal to or greater than the highest triple point water partial pressure of said one or more amorphous phosphate salts or said one or more precursor phosphate salts. In another embodiment of the present invention, the water partial pressure during said contacting step with the dehydration catalyst or the dehydration catalyst precursor mixture is equal to or greater than the average water partial pressure between the lowest triple point water partial pressure and the highest triple point water partial pressure of said one or more amorphous phosphate salts or said one or more precursor phosphate salts. In one embodiment of the present invention, the water partial pressure during said contacting step with the dehydration catalyst or the dehydration catalyst precursor mixture is at least 1 bar greater than the water partial pressure at the triple point of at least one of said one or more amorphous phosphate salts or said one or more precursor phosphate salts. In one embodiment of the present invention, the water partial pressure during said contacting step with the dehydration catalyst or the dehydration catalyst precursor mixture is at least 2 bar greater than the water partial pressure at the triple point of at least one of said one or more amorphous phosphate salts or said one or more precursor phosphate salts. In one embodiment of the present invention, the water partial pressure during said contacting step with the dehydration catalyst or the dehydration catalyst precursor mixture is at least 5 bar greater than the water partial pressure at the triple point of at least one of said one or more amorphous phosphate salts or said one or more precursor phosphate salts.

The contacting step with the dehydration catalyst or the dehydration catalyst precursor mixture can be performed under vacuum, at atmospheric pressure, or at higher than atmospheric pressure. In one embodiment of the present invention, the contacting step with the dehydration catalyst or the dehydration catalyst precursor mixture is performed under a total pressure of at least about 1 bar. In another embodiment of the present invention, the contacting step with the dehydration catalyst or the dehydration catalyst precursor mixture is performed under a total pressure between about 5 bar and about 40 bar. In another embodiment of the present invention, the contacting step with the dehydration catalyst or the dehydration catalyst precursor mixture is performed under a total pressure between about 10 bar and about 35 bar. In yet another embodiment of the present invention, the contacting step with the dehydration catalyst or the dehydration catalyst precursor mixture is performed under a total pressure of about 25 bar.

When hydroxypropionic acid, hydroxypropionic acid derivatives, or mixtures thereof are in the gas phase, and in another embodiment of the present invention, the contacting step with the dehydration catalyst or the dehydration catalyst precursor mixture is performed in a catalytic reactor with the gas mixture flowing down, flowing up, or flowing horizontally. In another embodiment of the present invention, the contacting step with the dehydration catalyst or the dehydration catalyst precursor mixture is performed in a catalytic reactor with the gas mixture flowing down. Also, the contacting step with the dehydration catalyst or the dehydration catalyst precursor mixture can be done in a batch form. In another embodiment of the present invention, the dehydration catalyst or the dehydration catalyst precursor mixture is suspended in an essentially chemically inert liquid. The contacting step with the dehydration catalyst or the dehydration catalyst precursor mixture can be performed by using different catalytic reactors known to those skilled in the art, such as, by way of example and not limitation, static reactor, stirred reactor, recirculation reactor, packed-bed flow reactor, and combinations thereof.

In one embodiment of the present invention, the contacting step with the dehydration catalyst or the dehydration catalyst precursor mixture is carried out in an apparatus, which is pressurized to ensure that all major components are in the liquid phase. In another embodiment of the present invention, the contacting step with the dehydration catalyst or the dehydration catalyst precursor mixture is carried out in an apparatus, which is operated at low temperature to ensure that all major components are in the liquid phase. In yet another embodiment of the present invention, the liquid mixture comprises an essentially chemically inert liquid. When all major components are in the liquid phase, the contacting step with the dehydration catalyst or the dehydration catalyst precursor mixture can be performed by using different catalytic reactors, known to those skilled in the art, such as, by way of example and not limitation, static reactor, fixed bed reactor, single-stage stirred tank reactor, multi-stage stirred tank reactor, multi-stage distillation column, and combinations thereof. The contacting step can be conducted batch-wise or continuously. The contacting step with the dehydration catalyst or the dehydration catalyst precursor mixture can be performed in a catalytic reactor with the liquid mixture comprising hydroxypropionic acid, hydroxypropionic acid derivatives, or mixtures thereof flowing down, flowing up, or flowing horizontally. In another embodiment of the present invention, the contacting step with the dehydration catalyst or the dehydration catalyst precursor mixture is performed in a catalytic reactor with the liquid mixture comprising hydroxypropionic acid, hydroxypropionic acid derivatives, or mixtures thereof flowing up.

In one embodiment of the present invention, the dehydration or isomerizations reactions of hydroxypropionic acid, hydroxypropionic acid derivatives or mixtures thereof occur in the aqueous phase, at least partially, and the pH of the reaction is between about 3 and about 8. In another embodiment of the present invention, the pH of the reaction in the aqueous phase is between about 4 and about 7. In yet another embodiment of the present invention, the pH of the reaction in the aqueous phase is between about 5 and about 6.

In one embodiment of the present invention, hydroxypropionic acid, hydroxypropionic acid derivatives, or mixtures thereof and water vapor contact the dehydration catalyst or the dehydration catalyst precursor mixture in a catalytic reactor with an interior surface material selected from the group consisting of amorphous silica, quartz, other silicon oxides, borosilicate glass, silicon, and mixtures thereof. In another embodiment of the present invention, hydroxypropionic acid, hydroxypropionic acid derivatives, or mixtures thereof and water vapor contact the dehydration catalyst or the dehydration catalyst precursor mixture in a catalytic reactor with an interior surface material selected from the group consisting of amorphous silica, quartz, borosilicate glass, and mixtures thereof. In another embodiment of the present invention, hydroxypropionic acid, hydroxypropionic acid derivatives, or mixtures thereof and water vapor contact the dehydration catalyst or the dehydration catalyst precursor mixture in a catalytic reactor with an interior surface material consisting essentially of borosilicate glass.

The acrylic acid mixture comprising acrylic acid, acrylic acid derivatives, or mixtures thereof produced in said contacting step with the dehydration catalyst or the dehydration catalyst precursor mixture is cooled to give a liquid acrylic acid composition as the product stream. The time required to cool the acrylic acid mixture must be controlled to reduce acrylic acid polymerization or decomposition to ethylene. In one embodiment of the present invention, the residence time of the acrylic acid mixture in the cooling step is less than about 30 s. In one embodiment of the present invention, the residence time of the acrylic acid mixture in the cooling step is between about 0.1 s and about 10 s.

The liquid acrylic acid composition comprising acrylic acid, acrylic acid derivatives, or mixtures thereof produced according with the present invention can be purified using some or all of the processes of extraction, drying, distilling, cooling, partial melting, and decanting described in US20130274518A1 (incorporated herein by reference) to produce crude and glacial acrylic acid. After purification, the crude and glacial acrylic acid can be polymerized to produce a superabsorbent polymer using processes that are similar to those described in US20130274697A1 (incorporated herein by reference).

In one embodiment of the present invention, said crude acrylic acid is esterified with an alcohol to produce an acrylate monomer. Non-limiting examples of alcohols are methanol, ethanol, butanol (n-butyl alcohol), 2-ethyl hexanol, isobutanol, tert-butyl alcohol, hexyl alcohol, octyl alcohol, isooctyl alcohol, lauryl alcohol, propyl alcohol, isopropyl alcohol, hydroxyethyl alcohol, hydroxypropyl alcohol, and polyols, such as hydroxyalkyl and alkylalkanolamine. In another embodiment of the present invention, said crude acrylic acid is esterified with methanol, ethanol, n-butyl alcohol, or 2-ethyl hexanol to produce methyl acrylate monomer, ethyl acrylate monomer, n-butyl acrylate monomer, or 2-ethylhexyl acrylate monomer, respectively. In yet another embodiment of the present invention, said methyl acrylate monomer, ethyl acrylate monomer, n-butyl acrylate monomer, or 2-ethylhexyl acrylate monomer is polymerized to produce methyl acrylate polymer, ethyl acrylate polymer, n-butyl acrylate polymer, or 2-ethylhexyl acrylate polymer, respectively. In even yet another embodiment of the present invention, said methyl acrylate monomer, ethyl acrylate monomer, n-butyl acrylate monomer, or 2-ethylhexyl acrylate monomer is co-polymerized with other monomer to produce methyl acrylate co-polymer, ethyl acrylate co-polymer, n-butyl acrylate co-polymer, or 2-ethylhexyl acrylate co-polymer, respectively. Non-limiting examples of other monomers are vinyl acetate and ethylene. In one embodiment of the present invention, said methyl acrylate polymer, ethyl acrylate polymer, n-butyl acrylate polymer, or 2-ethylhexyl acrylate polymer is blended with methyl methacrylate (MMA) to produce blends of MMA and methyl acrylate polymer, blends of MMA and ethyl acrylate polymer, blends of MMA and n-butyl acrylate polymer, or blends of MMA and 2-ethylhexyl acrylate polymer, respectively. Non-limiting applications of polymers, co-polymers, or blends are in surface coatings, paints, resins, adhesives, plastics, and dispersions. In another embodiment of the present invention, said alcohol is bio-based alcohol. In yet another embodiment of the present invention, said other monomer is bio-based monomer. In even yet another embodiment of the present invention, said MMA is bio-based MMA.

In one embodiment of the present invention, the method of making acrylic acid, acrylic acid derivatives, or mixtures thereof comprises contacting said hydroxypropionic acid, hydroxypropionic acid derivatives, and mixture thereof and said water vapor with said dehydration catalyst or said dehydration catalyst precursor mixture under conditions sufficient to produce acrylic acid, acrylic acid derivatives, or mixtures thereof in a yield of at least 50%. In another embodiment of the present invention, the method comprises contacting said hydroxypropionic acid, hydroxypropionic acid derivatives, and mixture thereof and said water vapor with said dehydration catalyst or said dehydration catalyst precursor mixture under conditions are sufficient to produce acrylic acid, acrylic acid derivatives, or mixtures thereof in a yield of at least about 70%. In another embodiment of the present invention, the method comprises contacting said hydroxypropionic acid, hydroxypropionic acid derivatives, and mixture thereof and said water vapor with said dehydration catalyst or said dehydration catalyst precursor mixture under conditions are sufficient to produce acrylic acid, acrylic acid derivatives, or mixtures thereof in a yield of at least about 80%. In another embodiment of the present invention, the method conditions are sufficient to produce acrylic acid, acrylic acid derivatives, or mixtures thereof with a selectivity of at least about 50%. In another embodiment of the present invention, the method conditions are sufficient to produce acrylic acid, acrylic acid derivatives, or mixtures thereof with a selectivity of at least about 70%. In another embodiment of the present invention, the method conditions are sufficient to produce acrylic acid, acrylic acid derivatives, or mixtures thereof with a selectivity of at least about 80%. In another embodiment of the present invention, the method conditions are sufficient to produce acrylic acid, acrylic acid derivatives, or mixtures thereof with propionic acid as an impurity, wherein the propionic acid selectivity is less than about 5%. In another embodiment of the present invention, the method conditions are sufficient to produce acrylic acid, acrylic acid derivatives, or mixtures thereof with propionic acid as an impurity, wherein the propionic acid selectivity is less than about 1%. In another embodiment of the present invention, the method conditions are sufficient to produce acrylic acid, acrylic acid derivatives, or mixtures thereof with a conversion of said hydroxypropionic acid, hydroxypropionic acid derivatives, or mixtures thereof of more than about 50%. In another embodiment of the present invention, the method conditions are sufficient to produce acrylic acid, acrylic acid derivatives, or mixtures thereof with a conversion of said hydroxypropionic acid, hydroxypropionic acid derivatives, or mixtures thereof of more than about 80%.

Among the benefits attainable by the foregoing embodiments is the low yield of side products. In one embodiment of the present invention, the conditions are sufficient to produce propionic acid in a yield of less than about 5% from hydroxypropionic acid. In another embodiment of the present invention, the conditions are sufficient to produce propionic acid in a yield of less than about 1%, from hydroxypropionic acid. In one embodiment of the present invention, the conditions are sufficient to produce each of acetic acid, pyruvic acid, 1,2-propanediol, hydroxyacetone, acrylic acid dimer, and 2,3-pentanedione in a yield of less than about 2% from hydroxypropionic acid present in the gaseous mixture. In another embodiment of the present invention, the conditions are sufficient to produce each of acetic acid, pyruvic acid, 1,2-propanediol, hydroxyacetone, acrylic acid dimer, and 2,3-pentanedione in a yield of less than about 0.5%, from hydroxypropionic acid present in the gaseous mixture. In one embodiment of the present invention, the conditions are sufficient to produce acetaldehyde in a yield of less than about 8% from hydroxypropionic acid present in the gaseous mixture. In another embodiment of the present invention, the conditions are sufficient to produce acetaldehyde in a yield of less than about 4% from hydroxypropionic acid present in the gaseous mixture. In another embodiment of the present invention, the conditions are sufficient to produce acetaldehyde in a yield of less than about 3%, from hydroxypropionic acid present in the gaseous mixture. These yields are believed to be, heretofore, unattainably low. Yet, these benefits are indeed achievable as further evidenced in the Examples set out below.

In one embodiment of the present invention, a method of making acrylic acid, acrylic acid derivatives, or mixtures thereof comprises: a) diluting an about 88 wt % lactic acid aqueous solution with water to form an about 20 wt % lactic acid aqueous solution; b) heating the about 20 wt % lactic acid aqueous solution at a temperature from about 95° C. to about 100° C. to hydrolyze oligomers of the lactic acid, producing a monomeric lactic acid solution comprising at least about 95 wt % of the lactic acid in monomeric form based on the total amount of lactic acid, lactic acid derivatives, or mixtures thereof; c) combining the monomeric lactic acid solution with nitrogen to form a liquid/gas blend; d) evaporating the liquid/gas blend in a evaporator with inside surface of borosilicate glass with a residence time of about 0.5 s to about 0.6 s at a temperature between about 300° C. and about 375° C. to produce a gas mixture comprising about 2.5 mol % lactic acid and about 50 mol % water; e) contacting said gas mixture with any dehydration catalyst disclosed in Section II ("Catalysts for the Conversion of Hydroxypropionic Acid or its Derivatives to Acrylic Acid or its Derivatives") or any dehydration catalyst precursor mixture disclosed in Section III ("Catalyst Preparation Method") in a catalytic reactor with an interior surface of borosilicate glass at a GHSV of about 4,500 h$^{-1}$, at a temperature from about 325° C. to about 400° C. under a total pressure from about 10 barg to about 25 barg producing the acrylic acid; and f) cooling the acrylic acid with a residence time between about 0.1 s and about 10 s.

In one embodiment of the present invention, a method of making acrylic acid is provided. The method comprises contacting: (a) a gas mixture comprising: i) lactic acid, ii) water, and iii) nitrogen, wherein said lactic acid is present in an amount of about 2.5 mol % and wherein said water is present in an amount of about 50 mol % based on the total moles of said gas mixture, with (b) a dehydration catalyst precursor mixture consisting essentially of: $(KPO_3)_n$ and $SiO_2$ in a weight ratio between about 1:1 and about 1:7; wherein said contacting step of said gas mixture with said dehydration catalyst precursor mixture is performed at a temperature from about 325° C. to about 400° C., at a WHSV between about 0.25 (g of lactic acid/g of catalyst·h) and about 1.0 (g of lactic acid/g of catalyst·h), and at a total pressure between about 10 barg and about 25 barg, in a reactor having an interior surface material selected from the group consisting of amorphous silica and borosilicate glass; whereby acrylic acid is produced as a result of said water and said lactic acid being contacted with said dehydration catalyst precursor mixture.

In one embodiment of the present invention, a method of making acrylic acid is provided. The method comprises contacting: (a) a gas mixture comprising: i) lactic acid, ii) water, and iii) nitrogen, wherein said lactic acid is present in an amount of about 2.5 mol % and wherein said water is present in an amount of about 50 mol % based on the total moles of said gas mixture, with (b) a dehydration catalyst precursor mixture consisting essentially of: $(KPO_3)_n$ and $BaSO_4$ in a weight ratio between about 1:1.3 and about 1:3.2; wherein said contacting step of said gas mixture with said dehydration catalyst precursor mixture is performed at a temperature from about 325° C. to about 400° C., at a WHSV between about 0.2 (g of lactic acid/g of catalyst·h) and about 0.4 (g of lactic acid/g of catalyst·h), and at a total pressure between about 10 barg and about 25 barg, in a reactor having an interior surface material selected from the group consisting of amorphous silica and borosilicate glass; whereby acrylic acid is produced as a result of said water and said lactic acid being contacted with said dehydration catalyst precursor mixture.

In one embodiment of the present invention, a method of making acrylic acid is provided. The method comprises contacting: (a) a gas mixture comprising: i) lactic acid, ii) water, and iii) nitrogen, wherein said lactic acid is present in an amount of about 2.5 mol % and wherein said water is present in an amount of about 50 mol % based on the total moles of said gas mixture, with (b) a dehydration catalyst precursor mixture consisting essentially of: $(KPO_3)_n$ and $BaTa_2O_6$ in a weight ratio of about 1:3.9; wherein said contacting step of said gas mixture with said dehydration catalyst precursor mixture is performed at a temperature from about 325° C. to about 400° C., at a WHSV of about 0.16 (g of lactic acid/g of catalyst·h), and at a total pressure between about 10 barg and about 25 barg, in a reactor having an interior surface material selected from the group consisting of amorphous silica and borosilicate glass; whereby acrylic acid is produced as a result of said water and said lactic acid being contacted with said dehydration catalyst precursor mixture.

In another embodiment of the present invention, a method of making acrylic acid, acrylic acid derivatives, or mixtures thereof comprises contacting: a) alkyl lactates or a solution comprising alkyl lactates and a solvent; b) water vapor; and c) any dehydration catalyst disclosed in Section II ("Catalysts for the Conversion of Hydroxypropionic Acid or its Derivatives to Acrylic Acid or its Derivatives") or any dehydration catalyst precursor mixture disclosed in Section III ("Catalyst Preparation Method") of the present invention; wherein the water partial pressure during said contacting step is equal to or greater than the water partial pressure at the triple point of at least one of said one or more amorphous phosphate salts or said one or more precursor phosphate salts in said dehydration catalyst or said dehydration catalyst precursor mixture; wherein said contacting step is performed at a temperature equal to or greater than the temperature at the triple point of at least one of said one or more amorphous phosphate salts or said one or more precursor phosphate salts in said dehydration catalyst or said dehydration catalyst precursor mixture; and whereby said acrylic acid, acrylic acid derivatives, or mixtures thereof is produced as a result of said water vapor and said alkyl lactate being contacted with said dehydration catalyst or said dehydration catalyst precursor mixture. In another embodiment of the present invention, said alkyl lactates are selected from the group consisting of methyl lactate, ethyl lactate, butyl lactate, 2-ethylhexyl lactate, and mixtures thereof. In another embodiment of the present invention, said solvent is selected from the group consisting of water, methanol, ethanol, butanol, 2-ethylhexanol, isobutanol, isooctyl alcohol, and mixtures thereof.

In another embodiment of the present invention, a method of making acrylic acid, acrylic acid derivatives, or mixtures thereof comprises: a) providing alkyl lactates or a solution comprising alkyl lactates and a solvent; b) optionally combining the alkyl lactates or the solution comprising the alkyl lactates and a solvent with an essentially chemically inert gas to form a liquid/gas blend; c) evaporating said alkyl lactates, or said solution comprising alkyl lactates and a solvent, or said liquid/gas blend to produce a gas mixture; and d) contacting said gas mixture with any dehydration catalyst disclosed in Section II ("Catalysts for the Conversion of Hydroxypropionic Acid or its Derivatives to Acrylic Acid or its Derivatives") or any dehydration catalyst precursor mixture disclosed in Section III ("Catalyst Preparation Method") under a water partial pressure of about 0.4 bar or more to produce said acrylic acid, acrylic acid derivatives, or mixtures thereof.

A method for dehydrating glycerin to acrolein is provided. The method comprises contacting: (a) glycerin, (b) water vapor, and (c) any dehydration catalyst disclosed in Section II ("Catalysts for the Conversion of Hydroxypropionic Acid or its Derivatives to Acrylic Acid or its Derivatives") or any dehydration catalyst precursor mixture disclosed in Section III ("Catalyst Preparation Method") of the present invention; wherein the water partial pressure during said contacting step is equal to or greater than the water partial pressure at the triple point of at least one of said one or more amorphous phosphate salts or said one or more precursor phosphate salts in said dehydration catalyst or said dehydration catalyst precursor mixture; wherein said contacting step is performed at a temperature equal to or greater than the temperature at the triple point of at least one of said one or more amorphous phosphate salts or said one or more precursor phosphate salts in said dehydration catalyst or said dehydration catalyst precursor mixture; and whereby said acrolein is produced as a result of said water vapor and said glycerin being contacted with said dehydration catalyst or said dehydration catalyst precursor mixture.

A method for isomerization of lactic acid, lactic acid derivatives, or mixtures thereof into 3-hydroxypropionic acid, 3-hydroxypropionic acid derivatives, or mixtures thereof is provided. The method comprises contacting: (a) 3-hydroxypropionic acid, 3-hydroxypropionic acid derivatives, or mixtures thereof, (b) water vapor, and (c) any dehydration catalyst disclosed in Section II ("Catalysts for the Conversion of Hydroxypropionic Acid or its Derivatives to Acrylic Acid or its Derivatives") or any dehydration catalyst precursor mixture disclosed in Section III ("Catalyst Preparation Method") of the present invention; wherein the water partial pressure during said contacting step is equal to or greater than the water partial pressure at the triple point of at least one of said one or more amorphous phosphate salts or said one or more precursor phosphate salts in said dehydration catalyst or said dehydration catalyst precursor mixture; wherein said contacting step is performed at a temperature equal to or greater than the temperature at the triple point of at least one of said one or more amorphous phosphate salts or said one or more precursor phosphate salts in said dehydration catalyst or said dehydration catalyst precursor mixture; and whereby said 3-hydroxypropionic acid, 3-hydroxypropionic acid derivatives, or mixtures thereof are produced as a result of said water vapor and said lactic acid, lactic acid derivatives, or mixtures thereof being contacted with said dehydration catalyst or said dehydration catalyst precursor mixture.

A method for reduction of hydroxypropionic acid, hydroxypropionic acid derivatives, and mixtures thereof into propionic acid, propionic acid derivatives, 1-propanol, 1-propanol derivatives, or mixtures thereof is provided. The method comprises contacting: (a) hydroxypropionic acid, hydroxypropionic acid derivatives, and mixtures thereof; (b) water vapor, (c) hydrogen gas, and (d) any dehydration catalyst disclosed in Section II ("Catalysts for the Conversion of Hydroxypropionic Acid or its Derivatives to Acrylic Acid or its Derivatives") or any dehydration catalyst precursor mixture disclosed in Section III ("Catalyst Preparation Method") of the present invention; wherein the water partial pressure during said contacting step is equal to or greater than the water partial pressure at the triple point of at least one of said one or more amorphous phosphate salts or said one or more precursor phosphate salts in said dehydration catalyst or said dehydration catalyst precursor mixture; wherein said contacting step is performed at a temperature equal to or greater than the temperature at the triple point of at least one of said one or more amorphous phosphate salts or said one or more precursor phosphate salts in said dehydration catalyst or said dehydration catalyst precursor mixture; and whereby said propionic acid, propionic acid derivatives, 1-propanol, 1-propanol derivatives, or mixtures thereof are produced as a result of said water vapor, said hydrogen gas, and said hydroxypropionic acid, hydroxypropionic acid derivatives, or mixtures thereof being contacted with said dehydration catalyst or said dehydration catalyst precursor mixture. In another embodiment of the present invention, said dehydration catalyst or said dehydration catalyst precursor mixture further comprises one or more transition metals selected from the groups 8 to 12 of the periodic table. Derivatives of propionic acid can be metal or ammonium salts of propionic acid, alkyl esters of propionic acid, or a mixture thereof. Non limiting examples of metal salts of propionic acid are sodium propionate, potassium propionate, and calcium propionate. Non limiting examples of alkyl esters of propionic acid are methyl propionate, ethyl propionate, butyl propionate, 2-ethylhexyl propionate, or mixtures thereof. A derivative of 1-propanol can be 1-alkyloxypropanol.

A method for dehydrating alcohols to alkenes is provided. The method comprises contacting: (a) one or more aliphatic alcohols, (b) water vapor, and (c) any dehydration catalyst disclosed in Section II ("Catalysts for the Conversion of Hydroxypropionic Acid or its Derivatives to Acrylic Acid or its Derivatives") or any dehydration catalyst precursor mixture disclosed in Section III ("Catalyst Preparation Method")

of the present invention; wherein the water partial pressure during said contacting step is equal to or greater than the water partial pressure at the triple point of at least one of said one or more amorphous phosphate salts or said one or more precursor phosphate salts in said dehydration catalyst or said dehydration catalyst precursor mixture; wherein said contacting step is performed at a temperature equal to or greater than the temperature at the triple point of at least one of said one or more amorphous phosphate salts or said one or more precursor phosphate salts in said dehydration catalyst or said dehydration catalyst precursor mixture; and whereby one or more alkenes are produced as a result of said water vapor and said one or more aliphatic alcohols being contacted with said dehydration catalyst or said dehydration catalyst precursor mixture. Non limiting examples of alcohols are ethanol, n-propanol, isopropanol, n-butanol, sec-butanol, isobutanol, tert-butanol, pentanol, ethylene glycol, propylene glycol, glycerol, other polyhydric alcohols, and alicyclic alcohols.

V. EXAMPLES

The following examples are provided to illustrate the invention, but are not intended to limit the scope thereof. Examples 1, 2, 5, 7, and 8 describe the preparation of different catalysts in accordance with various embodiments of the present invention. Examples 3, 4, and 6 describe the preparation of catalysts not according to the present invention. Example 9 describes the testing procedure of catalysts of Examples 1 through 6, Example 10 describes the testing procedure of the catalyst of Example 7, and Example 11 describes the testing procedure of the catalyst of Example 8. Examples 12 through 20 describe $(XPO_3)_n$ catalysts and their testing results, where X is Cs, K, Na, Li, and Ba. Examples 21 through 26 describe $K_xP_yO_z$ catalysts and their testing results, where x, y, and z are 5, 3, and 10; 2, 4, and 11; and 4, 2, and 7. Finally, Examples 27, 28, and 29 compare the performance of a $(KPO_3)_n$ and fused silica catalyst with that of a $(KPO_3)_n$ and alumina catalyst.

Example 1—$(KPO_3)_n$ and $BaSO_4$ Catalyst

Barium sulfate ($BaSO_4$, 100 wt %, 30.0 g, 128.5 mmol; Aldrich, St. Louis, Mo.; catalog #202762) and potassium phosphate monobasic ($KH_2PO_4$, 99.995 wt %, 23.33 g, 171.4 mmol; Fluka, St. Louis, Mo.; catalog #60216) were combined and ground together for 15 min at 500 rpm using a planetary ball mill PM 100 (Retsch, Haan, Germany; catalog #20.540.0003), a 125 mL grinding jar (Retsch, Haan, Germany; catalog #01.462.0136), and 7 grinding balls (Retsch, Haan, Germany, catalog #05.368.0028) to obtain a fine solid. The solid was transferred to a 600 mL glass beaker and calcined at 450° C. for 12 h with a heating ramp of 2° C./min and using a Nabertherm furnace N30/85 HA with P300 controller (Nabertherm, Lilienthal, Germany, catalog # N30/85 HA). After calcination, the material was kept inside the oven until it reached a temperature below 80° C.

The calcined solid was ground gently using a mortar and pestle to obtain particles of less than about 1 cm, followed by grinding for 90 s at 300 rpm using a planetary ball mill PM 100 (Retsch, Haan, Germany; catalog #20.540.0003), a 125 mL grinding jar (Retsch, Haan, Germany; catalog #01.462.0136), and 3 grinding balls (Retsch, Haan, Germany, catalog #05.368.0028). Then, the solids were sieved for 5 min using a vibratory sieve shaker AS 200 control (Retsch, Haan, Germany; catalog #30.018.0001), and sieves No. 70 and 140 (USA standard testing sieve, ASTM E-11 specifications; Gilson Company, Lewis Center, Ohio). The process of grinding particles retained on sieve No. 70 followed by sieving was repeated until all the material passed sieve No. 70. Finally, the solid retained on sieve No. 140 was re-sieved for 30 min to obtain a catalyst with particle size between 106 μm and 212 μm (28.5 g). The material was analyzed by XRD and $BaSO_4$ and T-$(KPO_3)_n$ were identified as the components of the dehydration catalyst precursor mixture.

Example 2—$(KPO_3)_n$ and $BaSO_4$ Catalyst

Barium sulfate ($BaSO_4$, 100 wt %, 50.0 g, 214.2 mmol; Aldrich, St. Louis, Mo.; catalog #202762) and potassium phosphate monobasic ($KH_2PO_4$, 100 wt %, 19.44 g, 142.8 mmol; Fluka, St. Louis, Mo.; catalog #60216) were combined and ground together for 15 min at 500 rpm using a planetary ball mill PM 100 (Retsch, Haan, Germany; catalog #20.540.0003), a 125 mL grinding jar (Retsch, Haan, Germany; catalog #01.462.0136), and 7 grinding balls (Retsch, Haan, Germany, catalog #05.368.0028) to obtain a fine solid. The solid was transferred to a 600 mL glass beaker and calcined at 450° C. for 12 h with a heating ramp of 2° C./min and using a Nabertherm furnace N30/85 HA with P300 controller (Nabertherm, Lilienthal, Germany, catalog # N30/85 HA). After calcination, the material was kept inside the oven until it reached a temperature below 80° C.

The calcined solid was ground gently using a mortar and pestle to obtain particles of less than about 1 cm, followed by grinding for 30 s at 300 rpm using a planetary ball mill PM 100 (Retsch, Haan, Germany; catalog #20.540.0003), a 125 mL grinding jar (Retsch, Haan, Germany; catalog #01.462.0136), and 3 grinding balls (Retsch, Haan, Germany, catalog #05.368.0028). Then, the solids were sieved for 5 min using a vibratory sieve shaker AS 200 control (Retsch, Haan, Germany; catalog #30.018.0001), and sieves No. 70 and 140 (USA standard testing sieve, ASTM E-11 specifications; Gilson Company, Lewis Center, Ohio). The process of grinding particles retained on sieve No. 70 followed by sieving was repeated until all the material passed sieve No. 70. Finally, the solids retained on sieve No. 140 were re-sieved for 30 min to obtain a catalyst with particle size between 106 μm and 212 μm (24.2 g). The material was analyzed by XRD and $BaSO_4$ and T-$(KPO_3)_n$ were identified as the components of the dehydration catalyst precursor mixture.

Example 3 (Comparative)—$BaSO_4$ Catalyst

Barium sulfate ($BaSO_4$, 100 wt %, 30.0 g, 128.5 mmol; Aldrich, St. Louis, Mo.; catalog #202762) was weighed, transferred to a 600 mL glass beaker, and calcined at 450° C. for 12 h with a heating ramp of 2° C./min and using a Nabertherm furnace N30/85 HA with P300 controller (Nabertherm, Lilienthal, Germany, catalog # N30/85 HA). After calcination, the material was kept inside the oven until it reached a temperature below 80° C.

The calcined solid was sieved using a vibratory sieve shaker AS 200 control (Retsch, Haan, Germany; catalog #30.018.0001), and sieves No. 70 and 400 (USA standard testing sieve, ASTM E-11 specifications; Gilson Company, Lewis Center, Ohio) until constant weight. The material with particle size over 38 m (3.4 g) was used as catalyst. After XRD analysis, $BaSO_4$ was identified as the only component.

Example 4 (Comparative)—$(KPO_3)_n$ and $K_2SO_4$ Catalyst

Potassium sulfate ($K_2SO_4$, 99.99 wt %, 30.0 g, 172.1 mmol; Aldrich, St. Louis, Mo., catalog #204129) and potassium phosphate monobasic ($KH_2PO_4$, 99.995 wt %, 31.24 g, 229.5 mmol; Fluka, St. Louis, Mo., catalog #60216) were combined and ground together for 15 min at 500 rpm using a planetary ball mill PM 100 (Retsch, Haan, Germany; catalog #20.540.0003), a 125 mL grinding jar (Retsch, Haan, Germany; catalog #01.462.0136), and 7 grinding balls (Retsch, Haan, Germany, catalog #05.368.0028) to obtain a fine solid. The solid was transferred to a 600 mL glass beaker and calcined at 450° C. for 12 h with a heating ramp of 2° C./min and using a Nabertherm furnace N30/85 HA with P300 controller (Nabertherm, Lilienthal, Germany, catalog # N30/85 HA). After calcination, the material was kept inside the oven until it reached a temperature below 80° C.

The calcined solid was ground gently using a mortar and pestle to obtain particles of less than about 1 cm, followed by grinding for 90 s at 300 rpm using a planetary ball mill PM 100 (Retsch, Haan, Germany; catalog #20.540.0003), a 125 mL grinding jar (Retsch, Haan, Germany; catalog #01.462.0136), and 3 grinding balls (Retsch, Haan, Germany, catalog #05.368.0028). Then, the solids were sieved for 5 min using a vibratory sieve shaker AS 200 control (Retsch, Haan, Germany; catalog #30.018.0001), and sieves No. 70 and 140 (USA standard testing sieve, ASTM E-11 specifications; Gilson Company, Lewis Center, Ohio). The process of grinding particles retained on sieve No. 70 followed by sieving was repeated until all the material passed sieve No. 70. Finally, the solid retained on sieve No. 140 was re-sieved until constant weight to obtain a catalyst with particle size between 106 m and 212 m (11.8 g). The material was analyzed by XRD and $K_2SO_4$ and T-$(KPO_3)_n$ were identified as the components of the dehydration catalyst precursor mixture.

Example 5—$(KPO_3)_n$ and $BaTa_2O_6$ and $Ba_3Ta_5O_{15}$ and $Ba_3Ta_2O_8$ Catalyst Barium tantalate ($BaTa_2O_6$, 97.1 wt %, 40.0 g, 65.3 mmol; Alfa, Ward Hill, Mass., catalog #39179) and potassium phosphate monobasic ($KH_2PO_4$, 99.995 wt %, 11.84 g, 87.0 mmol; Fluka, St. Louis, Mo., catalog #60216) were combined and ground together for 15 min at 500 rpm using a planetary ball mill PM 100 (Retsch, Haan, Germany; catalog #20.540.0003), a 125 mL grinding jar (Retsch, Haan, Germany; catalog #01.462.0136), and 7 grinding balls (Retsch, Haan, Germany, catalog #05.368.0028) to obtain a fine solid. The solid was transferred to a 600 mL glass beaker and calcined at 450° C. for 12 h with a heating ramp of 2° C./min and using a Nabertherm furnace N30/85 HA with P300 controller (Nabertherm, Lilienthal, Germany, catalog # N30/85 HA). After calcination, the material was kept inside the oven until it reached a temperature below 80° C.

The calcined solid was ground gently using a mortar and pestle to obtain particles of less than about 1 cm, followed by grinding for 30 s at 300 rpm using a planetary ball mill PM 100 (Retsch, Haan, Germany; catalog #20.540.0003), a 125 mL grinding jar (Retsch, Haan, Germany; catalog #01.462.0136), and 3 grinding balls (Retsch, Haan, Germany, catalog #05.368.0028). Then, the solids were sieved for 5 min using a vibratory sieve shaker AS 200 control (Retsch, Haan, Germany; catalog #30.018.0001), and sieves No. 70 and 140 (USA standard testing sieve, ASTM E-11 specifications; Gilson Company, Lewis Center, Ohio). The process of grinding particles retained on sieve No. 70 followed by sieving was repeated until all the material passed sieve No. 70. Finally, the solid retained on sieve No. 140 was re-sieved for 30 min to obtain a catalyst with particle size between 106 m and 212 m (21.2 g). The material was analyzed by XRD and $BaTa_2O_6$, $Ba_3Ta_5O_{15}$, $Ba_3Ta_2O_8$, and T-$(KPO_3)_n$ were identified as the components of the dehydration catalyst precursor mixture.

Example 6 (Comparative)—$BaTa_2O_6$ and $Ba_3Ta_5O_{15}$ and $Ba_3Ta_2O_8$ Catalyst Barium tantalate ($BaTa_2O_6$, 97.1 wt %, 40.0 g, 65.3 mmol; Alfa, Ward Hill, Mass., catalog #39179) was weighed, transferred to a 600 mL glass beaker, and calcined at 450° C. for 12 h with a heating ramp of 2° C./min and using a Nabertherm furnace N30/85 HA with P300 controller (Nabertherm, Lilienthal, Germany, catalog # N30/85 HA). After calcination, the material was kept inside the oven until it reached a temperature below 80° C.

The calcined solid was sieved using a vibratory sieve shaker AS 200 control (Retsch, Haan, Germany; catalog #30.018.0001), and sieves No. 70 and 400 (USA standard testing sieve, ASTM E-11 specifications; Gilson Company, Lewis Center, Ohio) until constant weight. The material with particle size over 38 m (41.5 g) was used as catalyst. After XRD analysis, $BaTa_2O_6$, $Ba_3Ta_5O_{15}$, and $Ba_3Ta_2O_8$ were identified as the components of the dehydration catalyst precursor mixture.

Example 7—$(KPO_3)_n$ and Quartz Silica Catalyst

Potassium phosphate monobasic ($KH_2PO_4$, 99.995 wt %, 20.00 g, 147.0 mmol; Fluka, St. Louis, Mo., catalog #60216) and silicon oxide quartz (crystalline $SiO_2$, 49.44 g; Alfa, Ward Hill, Mass., catalog #13024) were combined and ground together using a mortar and pestle to obtain a fine solid. Then, the material was transferred to a 600 mL glass beaker and calcined at 450° C. for 12 h with a heating ramp of 2° C./min and using a Nabertherm furnace N30/85 HA with P300 controller (Nabertherm, Lilienthal, Germany, catalog # N30/85 HA). After calcination, the material was kept inside the oven until it reached a temperature below 80° C.

The calcined solid was ground gently using a mortar and pestle. Then, the solids were sieved for 5 min using a vibratory sieve shaker AS 200 control (Retsch, Haan, Germany; catalog #30.018.0001), and sieves No. 70 and 140 (USA standard testing sieve, ASTM E-11 specifications; Gilson Company, Lewis Center, Ohio). The process of grinding particles retained on sieve No. 70 followed by sieving was repeated until all the material passed sieve No. 70. Finally, the solid retained on sieve No. 140 was re-sieved for 30 min to obtain a catalyst with particle size between 106 μm and 212 μm (20.7 g). The material was analyzed by XRD and T-$(KPO_3)_n$ and $SiO_2$ were identified as the components of the dehydration catalyst precursor mixture.

Example 8—26 wt % $(KPO_3)_n$ and 74 wt % Fused Silica Catalyst

Dipotassium phosphate ($K_2HPO_4$, 100 wt %, 40.00 g, 229.6 mmol; Fluka, St. Louis, Mo., catalog #60347), ammonium phosphate dibasic (($NH_4$)$_2$$HPO_4$, 97.7 wt %, 31.04 g, 229.6 mmol; Aldrich, St. Louis, Mo., catalog #379980), and amorphous silicon oxide (fused silica; $SiO_2$, 154.34 g; Aldrich, St. Louis, Mo., catalog #342831) were combined and ground together for 15 min at 500 rpm using a planetary ball mill PM 100 (Retsch, Haan, Germany; catalog #20.540.0003), a 500 mL grinding jar (Retsch, Haan, Germany; catalog #01.462.0227), and 25 grinding balls (Retsch, Haan, Germany, catalog #05.368.0093) to obtain a fine solid.

The solid was transferred to a 1000 mL glass beaker and calcined at 450° C. for 12 h with a heating ramp of 2° C./min and using a Nabertherm furnace N30/85 HA with P300 controller (Nabertherm, Lilienthal, Germany, catalog # N30/85 HA). After calcination, the material was kept inside the oven until it reached room temperature.

The calcined solid was ground gently using a mortar and pestle to obtain particles of less than about 1 cm, followed by grinding for 30 s at 300 rpm using a planetary ball mill PM 100 (Retsch, Haan, Germany; catalog #20.540.0003), a 500 mL grinding jar (Retsch, Haan, Germany; catalog #01.462.0227), and 5 grinding balls (Retsch, Haan, Germany, catalog #05.368.0093). Then, the solids were sieved for 5 min using a vibratory sieve shaker AS 200 control (Retsch, Haan, Germany; catalog #30.018.0001), and sieves No. 70 and 140 (USA standard testing sieve, ASTM E-11 specifications; Gilson Company, Lewis Center, Ohio). The process of grinding particles retained on sieve No. 70 followed by sieving was repeated until all the material passed sieve No. 70. Finally, the solid retained on sieve No. 140 was re-sieved for 30 min to obtain a catalyst with particle size between 106 m and 212 m (40.14 g). The material was analyzed by XRD and T-$(KPO_3)_n$ was identified as a component of the dehydration catalyst precursor mixture.

Example 9

Dehydration catalyst precursor mixtures prepared as described in Examples 1 to 6 were tested for the conversion of lactic acid to acrylic acid as follows. The reactions were carried out in a flow reactor system with temperature and mass flow controllers. The reactors were made of quartz (28 mm L×2 mm I.D.), housed in a heating block, and fed at the top with separate liquid and gas feeds through silica capillaries. These feeds were mixed together and heated gradually to 375° C. at 25 barg before reaching the dehydration catalyst bed. Volumes of dehydration catalyst precursor mixture of about 200 μL, placed on an isothermal heating zone at 375° C. (±1° C.), were used. The gas feed was composed of nitrogen ($N_2$, 6 NmL/min) and helium (He, 0.15 NmL/min), which was added as an internal standard for gas chromatograph (GC) analysis. The liquid feed was an aqueous solution of lactic acid (20 wt % L-lactic acid, 5 μL/min) prepared by mixing a commercial solution of lactic acid (ACS reagent, >85 wt %; Sigma-Aldrich, St. Louis, Mo., catalog #252476) with deionized water, followed by heating at 95° C. for 12 h and cooling to room temperature. The water partial pressure is calculated as 168.1 psi.

The reactor effluent was connected to another nitrogen line, which diluted the effluent by a factor of two. The helium internal standard normalized any variation in this dilution for analytical purposes. The dehydration catalysts were equilibrated for 6 h by contacting them with the mixed liquid and gas feeds, after which the condensed products were collected every 6 h by a liquid sampling system cooled to 10° C. Typically, 48 hour experiments were performed and 5 liquid samples were collected. These liquid samples were analyzed by offline high performance liquid chromatography (HPLC) and offline gas chromatography (GC). The gaseous products accumulated on the overhead space of the collection vials and were analyzed using sampling valves and online gas chromatography (GC).

The offline HPLC analyses were performed using an Agilent 1200 Series instrument equipped with a diode-array detector (Agilent Technologies, Santa Clara, Calif.) and an Atlantis T3 column (250 mm L×4.6 mm I.D.×5 micron; Waters, Milford, Mass.) using methods generally known by those having ordinary skill in the art to determine concentrations of acrylic acid and lactic acid.

The offline GC analyses were performed using a dual Channel TraceGC (Interscience, Breda, Netherlands) equipped with a FID detector and a DB-624 column (30 m L×0.25 mm I.D.×1.4 m; Agilent Technologies, Santa Clara, Calif.) using methods generally known by those having ordinary skill in the art to determine concentrations of acetaldehyde, acetic acid, acetone, acrylic acid, acrylic acid dimer, ethanol, hydroxyacetone, 2,3-pentanedione, 3-pentanone, propanal, propionic acid, and propanol.

The online GC analyses were performed using a CompactGC (Interscience, Breda, Netherlands) with three channels equipped with a FID detector coupled to a Rtx-624 column (30 m L×0.25 mm I.D.×1.4 μm; Restek, Bellefonte, Pa.), a TDC detector coupled to a Rt Q-bond column (30 m L×0.32 mm; Restek, Bellefonte, Pa.), and a TDC detector coupled to a Mol sieve MS5A column (10 m, Restek Corp., Bellefonte, Pa.) using methods generally known by those having ordinary skill in the art to determine concentrations of He, CO, $CO_2$, acetaldehyde, methane, ethylene, ethane, propane, and propylene.

Example 10

The dehydration catalyst precursor mixture prepared as described in Example 7 was tested for the conversion of lactic acid to acrylic acid as follows. A glass-lined stainless steel tube (14" or 356 mm length, 4 mm internal diameter; SGE Analytical Science Pty Ltd., Ringwood, Australia) was packed with glass wool at the bottom (0.64 $cm^3$, 2" or 51 mm, outside the heating zone), followed by dehydration catalyst precursor mixture in the middle (1.9 $cm^3$ bed volume, 6" or 152 mm bed length, inside the heating zone) and free space at the top (0.64 $cm^3$, 2" or 51 mm, inside the heating zone; 1.3 $cm^3$, 4" or 102 mm, outside the heating zone). The tube was placed inside an aluminum block and a clam shell furnace series 3210 (Applied Test Systems, Butler, Pa.) in a down-flow arrangement and the bottom of the reactor was connected to a PTFE-coated catch tank using a fused silica lined stainless steel tubing (⅛" or 3.2 mm external diameter; Supelco, St. Louis, Mo.) and Swagelok™ fittings. The reactor was purged by flowing $N_2$ gas (45 mL/min) at 360 psig (25 barg) using a Brooks gas flow controller (Hatfield, Pa.) and a Brooks back pressure regulator. Then, the reactor was heated (1° C./min ramp) until a final temperature of about 375° C. (tube wall temperature) was reached. A liquid solution of lactic acid in water (20.0 wt %) was fed at the top of the reactor at 0.045 mL/min though polyetheretherketone (PEEK™) tubing (1/16" or 1.6 mm external diameter; Upchurch Scientific, Oak Harbor, Wash.) using an Azura P4.1S Knauer pump (Berlin, Germany). Before contacting the dehydration catalyst, the gas phase concentrations were: nitrogen: 47.9 mol %; lactic acid: 2.5 mol %; and water: 49.6 mol % and the water partial pressure was 185.8 psi (12.8 bar). After contacting the dehydration catalyst, the reactor effluent was cooled and the liquid was collected in the catch tank and sampled periodically for analysis by offline HPLC using an Agilent 1100 system (Santa Clara, Calif.) equipped with a diode array detector and a Waters Atlantis T3 column (250 mm L×4.6 mm I.D.×5 micron; Waters, Milford, Mass.) and by offline GC using a Hewlett Packard HP6890 series system (Santa Clara, Calif.) equipped with a FID detector and Agilent CP-Wax 58 FFAP CB column (Clara, Calif.), using methods generally known by those having ordinary skill in the art.

The uncondensed gas effluents were discharged and analyzed periodically by online GC using an Agilent 7890 system (Santa Clara, Calif.) equipped with a FID detector and Varian CP-Para Bond Q column (Catalog # CP7351; Santa Clara, Calif.).

Time on stream (TOS) was 23 h, acrylic acid yield was 80.4 mol %, lactic acid conversion was 100 mol %, acrylic acid selectivity was 80.4 mol %, and propionic acid selectivity was 0.7 mol %.

Example 11

The dehydration catalyst precursor mixture prepared as described in Example 8 was tested for the conversion of lactic acid to acrylic acid as follows. A sample of dehydration catalyst precursor mixture was manually blended with amorphous silicon oxide ($SiO_2$, 1.37 g; pre-ground and sieved to 106-212 m; Aldrich, St. Louis, Mo., catalog #342831). A glass-lined stainless steel tube (14" or 356 mm length, 4 mm internal diameter; SGE Analytical Science Pty Ltd., Ringwood, Australia) was packed with glass wool at the bottom (0.80 cm$^3$, 2.5" or 64 mm, outside the heating zone), followed by the blend of silicon oxide and dehydration catalyst precursor mixture in the middle (2.55 cm$^3$ bed volume, 8" or 203 mm bed length, inside the heating zone) and free space at the top (1.10 cm$^3$, 3.5" or 89 mm, outside the heating zone). The tube was placed inside an aluminum block and a clam shell furnace series 3210 (8" length heating zone; Applied Test Systems, Butler, Pa.) in a down-flow arrangement and the bottom of the reactor was connected to a PTFE-coated catch tank using a fused silica lined stainless steel tubing (⅛" or 3.2 mm external diameter; Supelco, St. Louis, Mo.) and Swagelok™ fittings. The reactor was pressurized to 360 psig (25 barg) using a Brooks gas flow controller (Hatfield, Pa.) and a Brooks back pressure regulator and purged by flowing $N_2$ gas (45 mL/min). Then, the reactor was heated (1° C./min ramp) until a final temperature of about 375° C. (tube wall temperature) was reached. A liquid solution of lactic acid in water (20.0 wt %) was fed at the top of the reactor at 0.045 mL/min though polyetheretherketone (PEEK™) tubing (¹⁄₁₆" or 1.6 mm external diameter; Aldrich, St. Louis, Mo., catalog # ZA227293) using a Smartline 100 Knauer pump (Berlin, Germany). Before contacting the dehydration catalyst, the gas phase concentrations were: 47.9 mol % nitrogen, 2.5 mol % lactic acid, and 49.6 mol % water; and the water partial pressure was 185.8 psi (12.8 bar). After contacting the dehydration catalyst, the reactor effluent was cooled and the liquid was collected in the catch tank and sampled periodically for analysis by offline HPLC using an Agilent 1100 system (Santa Clara, Calif.) equipped with a diode array detector and a Waters Atlantis T3 column (250 mm L×4.6 mm I.D.×5 micron; Waters, Milford, Mass.) and by offline GC using a Hewlett Packard HP6890 series system (Santa Clara, Calif.) equipped with a FID detector and Agilent CP-Wax 58 FFAP CB column (Clara, Calif.), using methods generally known by those having ordinary skill in the art.

The uncondensed gas effluents were discharged and analyzed periodically by online GC using an Agilent 7890 system (Santa Clara, Calif.) equipped with a FID detector and Varian CP-Para Bond Q column (Catalog # CP7351; Santa Clara, Calif.).

Time on stream (TOS) was 50.4 h, acrylic acid yield was 85.1 mol %, lactic acid conversion was 98.3 mol %, acrylic acid selectivity was 86.6 mol %, and propionic acid selectivity was 0.3 mol %.

Table 1 describes the results for the different lactic acid conversion reactions using catalysts prepared as described in Examples 1 through 8. Table 1 provides a convenient comparison of the conversion of lactic acid to acrylic acid using catalysts according to the invention (i.e., Examples 1, 2, 5, 7, and 8) and those not according to the invention (i.e., Examples 3, 4, and 6).

TABLE 1

Results from testing of various catalysts

| Catalyst Example | Catalyst Precursor Composition | TOS, [h] | AAY, [mol %] | LAC, [mol %] | AAS, [mol %] | PAS, [mol %] | Water Partial Pressure, [psi] |
|---|---|---|---|---|---|---|---|
| Examples according to the present invention ||||||||
| 1 | $(KPO_3)_n$ + $BaSO_4$ | 67 | 74.7 | 90.8 | 82.2 | 0.7 | 168.1 |
| 2 | $(KPO_3)_n$ + $BaSO_4$ | 117 | 71.0 | 91.9 | 77.2 | 0.8 | 168.1 |
| 5 | $(KPO_3)_n$ + $BaTa_2O_6$ + $Ba_3Ta_5O_{15}$ + $Ba_3Ta_2O_8$ | 68 | 63.3 | 94.9 | 67.2 | 1.7 | 168.1 |
| 7 | $(KPO_3)_n$ + quartz $SiO_2$ | 23 | 80.4 | 100 | 80.4 | 0.7 | 185.8 |
| 8 | $(KPO_3)_n$ + amorphous $SiO_2$ | 50.4 | 85.1 | 98.3 | 86.6 | 0.3 | 185.8 |
| Examples not according to the present invention ||||||||
| 3 | $BaSO_4$ | 118 | 2.3 | 36.2 | 6.5 | 6.5 | 168.1 |
| 4 | $(KPO_3)_n$ + $K_2SO_4$ | 117 | 1.4 | 30.5 | 4.5 | 5.7 | 168.1 |
| 6 | $BaTa_2O_6$ + $Ba_3Ta_5O_{15}$ + $Ba_3Ta_2O_8$ | 117 | 2.6 | 40.9 | 6.4 | 9.9 | 168.1 |

Example 12—26 wt % (CsPO$_3$)$_n$ and 74 wt % Fused Silica Catalyst

Cesium nitrate (CsNO$_3$, 99.99 wt %, 30.00 g; Aldrich, St. Louis, Mo., catalog #202150), ammonium phosphate dibasic ((NH$_4$)$_2$HPO$_4$, 97.7 wt %, 20.80 g; Aldrich, St. Louis, Mo., catalog #379980), and amorphous silicon oxide (SiO$_2$, 72.03 g; Aldrich, St. Louis, Mo., catalog #342831) were combined and ground together for 15 min at 500 rpm using a planetary ball mill PM 100 (Retsch, Haan, Germany; catalog #20.540.0003), a 500 mL grinding jar (Retsch, Haan, Germany; catalog #01.462.0227), and 25 grinding balls (Retsch, Haan, Germany, catalog #05.368.0093) to obtain a fine solid. The solid was transferred to a 600 mL glass beaker and calcined at 450° C. for 12 h with a heating ramp of 2° C./min and using a Nabertherm furnace N30/85 HA with P300 controller (Nabertherm, Lilienthal, Germany, catalog # N30/85 HA).

After calcination, the material was kept inside the oven until it reached room temperature. The calcined solid was ground gently using a mortar and pestle to obtain particles of less than about 1 cm, followed by grinding for 30 s at 300 rpm using a planetary ball mill PM 100 (Retsch, Haan, Germany; catalog #20.540.0003), a 500 mL grinding jar (Retsch, Haan, Germany), and 6 grinding balls (Retsch, Haan, Germany). Then, the solids were sieved for 5 min using a vibratory sieve shaker AS 200 control (Retsch, Haan, Germany; catalog #30.018.0001), and sieves No. 70 and 140 (USA standard testing sieve, ASTM E-11 specifications; Gilson Company, Lewis Center, Ohio). The process of grinding particles retained on sieve No. 70 followed by sieving was repeated until all the material passed sieve No. 70. Finally, the solid retained on sieve No. 140 was re-sieved for 30 min to obtain a catalyst with particle size between 106 μm and 212 μm (34.1 g). The material was analyzed by XRD and (CsPO$_3$)$_n$ and Cs$_4$P$_2$O$_7$ were identified as components of the dehydration catalyst precursor mixture.

Example 13

A stainless steel glass-lined tube reactor (SGE Analytical Science Pty Ltd., Ringwood, Australia; P/N: 0827671) with 6.4 mm (¼ in.) OD, 4 mm ID, and 35.6 cm (14 in.) length was packed in 3 zones as follows: 1) bottom zone: quartz wool was packed to give a bottom zone length of 7.6 cm (3 in.); 2) middle zone/dehydration zone: 1.4 g of the catalyst prepared in Example 12 were mixed with 1.4 g of fused silica (Sigma-Aldrich Co., St. Louis, Mo.; catalog #: 342831; ground and sieved to 102-212 μm) to form a 13 wt % (CsPO$_3$)$_n$ and 87 wt % fused silica catalyst and then packed to give a catalyst bed length of 20.3 cm (8 in.; 2.5 mL catalyst bed volume); and 3) top zone/evaporator zone was empty and 7.6 cm (3 in.) in length.

The reactor was first placed inside an 8 in. long aluminum block such that the top of the catalyst bed and the top of the aluminum block are aligned. Then, the aluminum block and the reactor were placed in a Series 3210 8 in. long clam shell furnace (Applied Test Systems, Butler, Pa.). The reactor was set-up in a down-flow arrangement and was equipped with a Knauer Smartline 100 feed pump (Knauer GmbH, Berlin, Germany), a Brooks 0254 gas flow controller (Brooks Instrument LLC, Hatfield, Pa.), a Brooks back pressure regulator, and a Teflon-lined catch tank. The head of the reactor was fitted with a 1.6 mm (¹⁄₁₆ in.) stainless steel line, as a nitrogen feed line, and a 1.6 mm (¹⁄₁₆ in.) polyetheretherketone (PEEK™) tubing (Supelco Inc., Bellefonte, Pa.), as a liquid feed supply line connected to the feed pump. The bottom of the reactor was connected to the catch tank using a 3.2 mm (⅛ in.) fused silica lined stainless steel tubing and Swagelok™ fittings. The clam shell furnace was heated such that the reactor wall temperature was kept constant at about 375° C. during the course of the reaction.

The reactor was fed with separate liquid and gas feeds, which were mixed together before reaching the catalyst bed. The inert gas was nitrogen at 24.8 barg (360 psig) pressure and was fed into the reactor at a rate of 45 mL/min (under STP conditions). The liquid feed was an aqueous solution of lactic acid (20 wt % L-lactic acid) and was fed into the reactor at a rate of 0.045 mL/min. After the evaporation zone, the resulting gas feed stream had the following composition: 49.8 mol % water, 47.8 mol % nitrogen, and 2.5 mol % lactic acid. In the dehydration zone, the GHSV was about 2,215 h$^{-1}$, WHSV was about 0.4 h$^{-1}$, and water partial pressure was about 13 bar (186 psi).

The gas product stream was cooled and analyzed on-line by an Agilent 7890A GC (Agilent Technologies, Inc., Santa Clara, Calif.) equipped with a FID detector and Varian CP-PoraBond Q column (Agilent Technologies, Inc., Santa Clara, Calif.; Catalog # CP7351). The liquid product stream was collected in the catch tank and analyzed off-line (using methods generally known by those having ordinary skill in the art) using an Agilent 1100 HPLC (Agilent Technologies, Inc., Santa Clara, Calif.), equipped with a diode array detector (DAD) and an Atlantis T3 column (Waters Corp., Milford, Mass.; Catalog #186003748), and a Hewlett Packard HP6890 series GC (Agilent Technologies, Inc., Santa Clara, Calif.), equipped with an FID detector and Agilent CP-Wax 58 FFAP CB column (Agilent Technologies, Inc., Santa Clara, Calif.; Catalog # CP7717).

The liquid product stream was cooled and collected over a period of about 3 h. The overall acrylic acid yield (AAY) was 83.3 mol %, acrylic acid selectivity (AAS) was 83.3 mol %, lactic acid conversion (LAC) was 100 mol %, and propionic acid selectivity (PAS) was 0.21 mol %.

Then, with all other conditions remaining the same as above, we varied the nitrogen and water partial pressures at various reaction temperatures and the results are shown in Table 2 below. The time on stream (TOS) for each of these conditions was about 3 h.

TABLE 2

Results from testing of the catalyst:
13 wt % (CsPO$_3$)$_n$ and 87 wt % fused silica

| Reaction T, [° C.] | Nitrogen Pressure, [psi] | Water Partial Pressure, [psi] | AAY, [mol %] | LAC, [mol %] | AAS, [mol %] | PAS, [mol %] |
|---|---|---|---|---|---|---|
| 350 | 360 | 186.4 | 77.7 | 92.5 | 84 | 0.36 |
|  | 160 | 86.9 | 79.1 | 89.6 | 88.3 | 0.28 |
|  | 20 | 17.2 | 61.8 | 76.1 | 81.4 | 0.40 |
| 375 | 360 | 186.4 | 83.3 | 100 | 83.3 | 0.21 |
|  | 160 | 86.9 | 87.4 | 100 | 87.4 | 0.29 |
|  | 80 | 47 | 88.4 | 100 | 88.4 | 0.42 |
|  | 40 | 27.1 | 85.1 | 95.9 | 88.8 | 0.53 |
|  | 20 | 17.2 | 83.8 | 95.1 | 88.2 | 0.61 |
| 400 | 360 | 186.4 | 79 | 100 | 79 | 0.82 |
|  | 160 | 86.9 | 89.3 | 100 | 89.3 | 0.79 |
|  | 20 | 17.2 | 78.7 | 94 | 83.8 | 1.58 |

Example 14

1.315 g of the catalyst prepared in Example 8 were mixed with 1.315 g of fused silica (Sigma-Aldrich Co., St. Louis, Mo.; catalog #: 342831; ground and sieved to 102-212 μm) to form a 13 wt % $(KPO_3)_n$ and 87 wt % fused silica catalyst and tested in the experimental setup of and using the same procedure as in Example 13. The results are shown in Table 3 below.

TABLE 3

Results from testing of the catalyst:
13 wt % $(KPO_3)_n$ and 87 wt % fused silica

| Reaction T, [° C.] | Nitrogen Pressure, [psi] | Water Partial Pressure, [psi] | AAY, [mol %] | LAC, [mol %] | AAS, [mol %] | PAS, [mol %] |
|---|---|---|---|---|---|---|
| 350 | 360 | 186.4 | 77.6 | 84.6 | 91.8 | 0.05 |
|  | 160 | 86.9 | 72.7 | 78.9 | 92.2 | 0 |
| 375 | 360 | 186.4 | 84.7 | 100 | 84.7 | N/A |
|  | 160 | 86.9 | 85.8 | 100 | 85.8 | N/A |
|  | 80 | 47 | 45.9 | 56.5 | 81.2 | 0.33 |
| 400 | 360 | 186.4 | 89.4 | 97.1 | 92.1 | 0.18 |
|  | 160 | 86.9 | 89.8 | 100 | 89.8 | 0.15 |

Example 15—26 wt % $(NaPO_3)_n$ and 74 wt % Fused Silica Catalyst

Disodium phosphate ($Na_2HPO_4$, 99.999 wt %, 20.00 g; Fluka, St. Louis, Mo., catalog #71629), ammonium phosphate dibasic (($NH_4$)$_2HPO_4$, 97.7 wt %, 19.04 g; Aldrich, St. Louis, Mo., catalog #379980), and amorphous silicon oxide ($SiO_2$, 81.77 g; Aldrich, St. Louis, Mo., catalog #342831) were combined and ground together for 15 min at 500 rpm using a planetary ball mill PM 100 (Retsch, Haan, Germany; catalog #20.540.0003), a 500 mL grinding jar (Retsch, Haan, Germany; catalog #01.462.0227), and 25 grinding balls (Retsch, Haan, Germany, catalog #05.368.0093) to obtain a fine solid. The solid was transferred to a 600 mL glass beaker and calcined at 450° C. for 12 h with a heating ramp of 2° C./min and using a Nabertherm furnace N30/85 HA with P300 controller (Nabertherm, Lilienthal, Germany, catalog # N30/85 HA). After calcination, the material was kept inside the oven until it reached room temperature.

The calcined solid was ground gently using a mortar and pestle to obtain particles of less than about 1 cm, followed by grinding for 30 s at 300 rpm using a planetary ball mill PM 100 (Retsch, Haan, Germany; catalog #20.540.0003), a 125 mL grinding jar (Retsch, Haan, Germany; catalog #01.462.0136), and 3 grinding balls (Retsch, Haan, Germany; catalog #05.368.0028). Then, the solids were sieved for 5 min using a vibratory sieve shaker AS 200 control (Retsch, Haan, Germany; catalog #30.018.0001), and sieves No. 70 and 140 (USA standard testing sieve, ASTM E-11 specifications; Gilson Company, Lewis Center, Ohio). The process of grinding particles retained on sieve No. 70 followed by sieving was repeated until all the material passed sieve No. 70. Finally, the solid retained on sieve No. 140 was re-sieved for 30 min to obtain a catalyst with particle size between 106 m and 212 m (45.0 g). The material was analyzed by XRD and $Na_3P_3O_9$ and $(NaPO_3)_n$ were identified as components of the dehydration catalyst precursor mixture.

Example 16

1.35 g of the catalyst prepared in Example 15 were mixed with 1.35 g of fused silica (Sigma-Aldrich Co., St. Louis, Mo.; catalog #: 342831; ground and sieved to 102-212 μm) to form a 13 wt % $(NaPO_3)_n$ and 87 wt % fused silica catalyst and tested in the experimental setup of and using the same procedure as in Example 13. The results are shown in Table 4 below.

TABLE 4

Results from testing of the catalyst:
13 wt % $(NaPO_3)_n$ and 87 wt % fused silica

| Reaction T, [° C.] | Nitrogen Pressure, [psi] | Water Partial Pressure, [psi] | AAY, [mol %] | LAC, [mol %] | AAS, [mol %] | PAS, [mol %] |
|---|---|---|---|---|---|---|
| 350 | 360 | 186.4 | 35.6 | 54.6 | 65.3 | 0 |
|  | 160 | 86.9 | 23.3 | 40.3 | 57.8 | 0 |
|  | 80 | 47 | 9.3 | 29.8 | 31.4 | 0.21 |
| 375 | 360 | 186.4 | 56.7 | 88.6 | 64.1 | 0.02 |
|  | 160 | 86.9 | 42.6 | 68.4 | 62.3 | 0.08 |
| 400 | 460 | 236.2 | 62 | 90.9 | 68.2 | 0.14 |
|  | 360 | 186.4 | 57.2 | 89.5 | 63.9 | 0.12 |
|  | 160 | 86.9 | 47.3 | 81.6 | 57.9 | 0.12 |
|  | 80 | 47 | 38.1 | 79.9 | 47.6 | 49.1 |

Note that an extrapolation of the AAS data at either 400° C. or 375° C. to higher nitrogen pressures yields AAS of 90 mol % at pressure of about 1,200 psi, or equivalently, water partial pressure of about 605 psi. At those pressures, we expect that the LAC would be 100 mol % and the AAY would be 90 mol %.

Example 17 (Comparative)—26 wt % $(LiPO_3)_n$ and 74 wt % Fused Silica Catalyst

Lithium nitrate ($LiNO_3$, 92.4 wt %, 20.00 g; Aldrich, St. Louis, Mo., catalog #229741), ammonium phosphate dibasic (($NH_4$)$_2HPO_4$, 97.7 wt %, 36.23 g; Aldrich, St. Louis, Mo., catalog #379980), and amorphous silicon oxide ($SiO_2$, 60.09 g; Aldrich, St. Louis, Mo., catalog #342831) were combined and ground together for 15 min at 500 rpm using a planetary ball mill PM 100 (Retsch, Haan, Germany; catalog #20.540.0003), a 500 mL grinding jar (Retsch, Haan, Germany; catalog #01.462.0227), and 25 grinding balls (Retsch, Haan, Germany, catalog #05.368.0093) to obtain a fine solid. The solid was transferred to a 600 mL glass beaker and calcined at 450° C. for 12 h with a heating ramp of 2° C./min and using a Nabertherm furnace N30/85 HA with P300 controller (Nabertherm, Lilienthal, Germany, catalog # N30/85 HA). After calcination, the material was kept inside the oven until it reached room temperature.

The calcined solid was ground gently using a mortar and pestle to obtain particles of less than about 1 cm, followed by grinding for 30 s at 300 rpm using a planetary ball mill PM 100 (Retsch, Haan, Germany; catalog #20.540.0003), a 125 mL grinding jar (Retsch, Haan, Germany; catalog #01.462.0136), and 3 grinding balls (Retsch, Haan, Germany; catalog #05.368.0028). Then, the solids were sieved for 5 min using a vibratory sieve shaker AS 200 control (Retsch, Haan, Germany; catalog #30.018.0001), and sieves No. 70 and 140 (USA standard testing sieve, ASTM E-11 specifications; Gilson Company, Lewis Center, Ohio). The process of grinding particles retained on sieve No. 70 followed by sieving was repeated until all the material passed sieve No. 70. Finally, the solid retained on sieve No. 140 was re-sieved for 30 min to obtain a catalyst with particle size between 106 μm and 212 μm (36.3 g). The material was analyzed by XRD and $(LiPO_3)_n$ was identified as a component of the dehydration catalyst precursor mixture.

Example 18 (Comparative)

1.44 g of the catalyst prepared in Example 17 were mixed with 1.44 g of fused silica (Sigma-Aldrich Co., St. Louis, Mo.; catalog #: 342831; ground and sieved to 102-212 μm) to form a 13 wt % $(LiPO_3)_n$ and 87 wt % fused silica catalyst and tested in the experimental setup of and using the same procedure as in Example 13 (in this Example 18, the WHSV was about 0.38 $h^{-1}$). The results are shown in Table 5 below.

TABLE 5

Results from testing of the catalyst:
13 wt % $(LiPO_3)_n$ and 87 wt % fused silica

| Reaction T, [° C.] | Nitrogen Pressure, [psi] | Water Partial Pressure, [psi] | AAY, [mol %] | LAC, [mol %] | AAS, [mol %] | PAS, [mol %] |
|---|---|---|---|---|---|---|
| 350 | 360 | 186.4 | 1.3 | 68.6 | 1.9 | 0.13 |
|  | 160 | 86.9 | 0.8 | 69.5 | 1.2 | 0.18 |
| 375 | 450 | 231.3 | 4.7 | 100 | 4.7 | 0.28 |
|  | 360 | 186.4 | 11.8 | 100 | 11.8 | 0.03 |
|  | 160 | 86.9 | 1.6 | 93.7 | 1.7 | 0.35 |
| 400 | 360 | 186.4 | 6.6 | 100 | 6.6 | 1.1 |

Example 19 (Comparative)—26 wt % $(Ba(PO_3)_2)_n$ and 74 wt % Fused Silica Catalyst Barium nitrate $(Ba(NO_3)_2$, 95.91 wt %, 25.00 g; Aldrich, St. Louis, Mo., catalog #202754), ammonium phosphate dibasic $((NH_4)_2HPO_4$, 97.7 wt %, 24.80 g; Aldrich, St. Louis, Mo., catalog #379980), and amorphous silicon oxide $(SiO_2$, 77.10 g; Aldrich, St. Louis, Mo., catalog #342831) were combined and ground together for 15 min at 500 rpm using a planetary ball mill PM 100 (Retsch, Haan, Germany; catalog #20.540.0003), a 500 mL grinding jar (Retsch, Haan, Germany; catalog #01.462.0227), and 25 grinding balls (Retsch, Haan, Germany, catalog #05.368.0093) to obtain a fine solid. The solid was transferred to a 600 mL glass beaker and calcined at 450° C. for 12 h with a heating ramp of 2° C./min and using a Nabertherm furnace N30/85 HA with P300 controller (Nabertherm, Lilienthal, Germany, catalog # N30/85 HA). After calcination, the material was kept inside the oven until it reached room temperature.

The calcined solid was ground gently using a mortar and pestle to obtain particles of less than about 1 cm, followed by grinding for 30 s at 300 rpm using a planetary ball mill PM 100 (Retsch, Haan, Germany; catalog #20.540.0003), a 125 mL grinding jar (Retsch, Haan, Germany; catalog #01.462.0136), and 3 grinding balls (Retsch, Haan, Germany; catalog #05.368.0028). Then, the solids were sieved for 5 min using a vibratory sieve shaker AS 200 control (Retsch, Haan, Germany; catalog #30.018.0001), and sieves No. 70 and 140 (USA standard testing sieve, ASTM E-11 specifications; Gilson Company, Lewis Center, Ohio). The process of grinding particles retained on sieve No. 70 followed by sieving was repeated until all the material passed sieve No. 70. Finally, the solid retained on sieve No. 140 was re-sieved for 30 min to obtain a catalyst with particle size between 106 μm and 212 μm (22.7 g). The material was analyzed by XRD and $(Ba(PO_3)_2)_n$ was identified as a component of the dehydration catalyst precursor mixture.

Example 20 (Comparative)

1.3 g of the catalyst prepared in Example 19 were mixed with 1.3 g of fused silica (Sigma-Aldrich Co., St. Louis, Mo.; catalog #: 342831; ground and sieved to 102-212 μm) to form a 13 wt % $(Ba(PO_3)_2)_n$ and 87 wt % fused silica catalyst and tested in the experimental setup of and using the same procedure as in Example 13 (in this Example 20, the bottom zone was 6.4 cm (2.5 in.) in length). The liquid product stream was cooled and collected over a period of about 5 h. The overall acrylic acid yield (AAY) was 2 mol %, acrylic acid selectivity (AAS) was 2 mol %, lactic acid conversion (LAC) was 100 mol %, propionic acid selectivity (PAS) was 0.37 mol %, and acetaldehyde yield was about 95 mol %.

Table 6 below shows selective results from Tables 2 through 5, and Examples 19 and 20 to compare the effect of metal X in the catalyst $(XPO_3)_n$ on the performance.

TABLE 6

Results from catalysts $(XPO_3)_n$ and fused silica at 375° C. and various pressures.

| Metal X; Catalyst | Nitrogen Pressure, [psi] | Water Partial Pressure, [psi] | AAY, [mol %] | LAC, [mol %] | AAS, [mol %] | PAS, [mol %] |
|---|---|---|---|---|---|---|
| Example not according to the present invention ||||||||
| X = Li; $(LiPO_3)_n$ | 360 | 186.4 | 11.8 | 100 | 11.8 | 0.03 |
|  | 160 | 86.9 | 1.6 | 93.7 | 1.7 | 0.35 |
| Examples according to the present invention ||||||||
| X = Na; $(NaPO_3)_n$ | 360 | 186.4 | 56.7 | 88.6 | 64.1 | 0.02 |
|  | 160 | 86.9 | 42.6 | 68.4 | 62.3 | 0.08 |
| X = K; $(KPO_3)_n$ | 360 | 186.4 | 84.7 | 100 | 84.7 | N/A |
|  | 160 | 86.9 | 85.8 | 100 | 85.8 | N/A |
| X = Cs; $(CsPO_3)_n$ | 360 | 186.4 | 83.3 | 100 | 83.3 | 0.21 |
|  | 160 | 86.9 | 87.4 | 100 | 87.4 | 0.29 |
| Example not according to the present invention ||||||||
| X = Ba; $(Ba(PO_3)_2)_n$ | 360 | 186.4 | 2 | 100 | 2 | 0.37 |

Example 21—26 wt % $K_5P_3O_{10}$ and 74 wt % Fused Silica Catalyst

Dipotassium phosphate $(K_2HPO_4$, 100 wt %, 30.00 g; Fluka, St. Louis, Mo., catalog #60347), ammonium phosphate dibasic ((NH$_4$)$_2$HPO$_4$, 97.7 wt %, 4.66 g; Aldrich, St. Louis, Mo., catalog #379980), and amorphous silicon oxide (SiO$_2$, 87.93 g; Aldrich, St. Louis, Mo., catalog #342831) were combined and ground together for 15 min at 500 rpm using a planetary ball mill PM 100 (Retsch, Haan, Germany; catalog #20.540.0003), a 500 mL grinding jar (Retsch, Haan, Germany; catalog #01.462.0227), and 25 grinding balls (Retsch, Haan, Germany, catalog #05.368.0093) to obtain a fine solid. The solid was transferred to a 600 mL glass beaker and calcined at 450° C. for 12 h with a heating ramp of 2° C./min and using a Nabertherm furnace N30/85 HA with P300 controller (Nabertherm, Lilienthal, Germany, catalog # N30/85 HA). After calcination, the material was kept inside the oven until it reached room temperature.

The calcined solid was ground gently using a mortar and pestle to obtain particles of less than about 1 cm, followed by grinding for 30 s at 300 rpm using a planetary ball mill PM 100 (Retsch, Haan, Germany; catalog #20.540.0003), a 125 mL grinding jar (Retsch, Haan, Germany; catalog #01.462.0136), and 3 grinding balls (Retsch, Haan, Germany; catalog #05.368.0028). Then, the solids were sieved for 5 min using a vibratory sieve shaker AS 200 control (Retsch, Haan, Germany; catalog #30.018.0001), and sieves No. 70 and 140 (USA standard testing sieve, ASTM E-11 specifications; Gilson Company, Lewis Center, Ohio). The process of grinding particles retained on sieve No. 70 followed by sieving was repeated until all the material passed sieve No. 70. Finally, the solid retained on sieve No. 140 was re-sieved for 30 min to obtain a catalyst with particle size between 106 μm and 212 μm (12.9 g). The material was analyzed by XRD and K$_5$P$_3$O$_{10}$.2H$_2$O was identified as a component of the dehydration catalyst precursor mixture.

Example 22

1.155 g of the catalyst prepared in Example 21 were mixed with 1.155 g of fused silica (Sigma-Aldrich Co., St. Louis, Mo.; catalog #: 342831; ground and sieved to 102-212 μm) to form a 13 wt % K$_5$P$_3$O$_{10}$ and 87 wt % fused silica catalyst and tested in the experimental setup of and using the same procedure as in Example 13 (in this Example 22, the WHSV was about 0.47 h$^{-1}$). The results are shown in Table 7 below.

TABLE 7

Results from testing of the catalyst: 13 wt % K$_5$P$_3$O$_{10}$ and 87 wt % fused silica

| Reaction T, [° C.] | Nitrogen Pressure, [psi] | Water Partial Pressure, [psi] | AAY, [mol %] | LAC, [mol %] | AAS, [mol %] | PAS, [mol %] |
|---|---|---|---|---|---|---|
| 350 | 360 | 186.4 | 25.7 | 100 | 25.7 | 2.57 |
|  | 160 | 86.9 | 39.8 | 100 | 39.8 | 2.52 |
| 375 | 360 | 186.4 | 32.5 | 100 | 32.5 | 2.67 |
|  | 160 | 86.9 | 58.6 | 100 | 58.6 | 3.08 |
|  | 80 | 47 | 56.4 | 100 | 56.4 | 3.32 |
|  | 40 | 27.1 | 53.8 | 89.9 | 59.8 | 2.59 |
| 400 | 360 | 186.4 | 32.5 | 100 | 32.5 | 8.23 |

Example 23 (Comparative)—26 wt % K$_2$P$_4$O$_{11}$ and 74 wt % Fused Silica Catalyst Dipotassium phosphate (K$_2$HPO$_4$, 100 wt %, 15.00 g; Fluka, St. Louis, Mo., catalog #60347), ammonium phosphate dibasic ((NH$_4$)$_2$HPO$_4$, 97.7 wt %, 34.92 g; Aldrich, St. Louis, Mo., catalog #379980), and amorphous silicon oxide (SiO$_2$, 92.67 g; Aldrich, St. Louis, Mo., catalog #342831) were combined and ground together for 15 min at 500 rpm using a planetary ball mill PM 100 (Retsch, Haan, Germany; catalog #20.540.0003), a 500 mL grinding jar (Retsch, Haan, Germany; catalog #01.462.0227), and 25 grinding balls (Retsch, Haan, Germany, catalog #05.368.0093) to obtain a fine solid. The solid was transferred to a 600 mL glass beaker and calcined at 450° C. for 12 h with a heating ramp of 2° C./min and using a Nabertherm furnace N30/85 HA with P300 controller (Nabertherm, Lilienthal, Germany, catalog # N30/85 HA). After calcination, the material was kept inside the oven until it reached room temperature.

The calcined solid was ground gently using a mortar and pestle to obtain particles of less than about 1 cm, followed by grinding for 30 s at 300 rpm using a planetary ball mill PM 100 (Retsch, Haan, Germany; catalog #20.540.0003), a 125 mL grinding jar (Retsch, Haan, Germany; catalog #01.462.0136), and 3 grinding balls (Retsch, Haan, Germany; catalog #05.368.0028). Then, the solids were sieved for 5 min using a vibratory sieve shaker AS 200 control (Retsch, Haan, Germany; catalog #30.018.0001), and sieves No. 70 and 140 (USA standard testing sieve, ASTM E-11 specifications; Gilson Company, Lewis Center, Ohio). The process of grinding particles retained on sieve No. 70 followed by sieving was repeated until all the material passed sieve No. 70. Finally, the solid retained on sieve No. 140 was re-sieved for 30 min to obtain a catalyst with particle size between 106 m and 212 μm (61.0 g). The material was analyzed by XRD and an unknown phase, presumably K$_2$P$_4$O$_{11}$, was identified as a component of the dehydration catalyst precursor mixture.

Example 24 (Comparative)

1.6 g of the catalyst prepared in Example 23 were mixed with 1.6 g of fused silica (Sigma-Aldrich Co., St. Louis, Mo.; catalog #: 342831; ground and sieved to 102-212 μm) to form a 13 wt % K$_2$P$_4$O$_{11}$ and 87 wt % fused silica catalyst and tested in the experimental setup of and using the same procedure as in Example 13 (in this Example 24, the OD of the reactor tube was 1.3 cm (½ in.)). The results are shown in Table 8 below.

TABLE 8

Results from testing of the catalyst: 13 wt % K$_2$P$_4$O$_{11}$ and 87 wt % fused silica

| Reaction T, [° C.] | Nitrogen Pressure, [psi] | Water Partial Pressure, [psi] | AAY, [mol %] | LAC, [mol %] | AAS, [mol %] | PAS, [mol %] |
|---|---|---|---|---|---|---|
| 250 | 360 | 186.4 | 0.7 | 9.5 | 7.6 | 0 |
|  | 80 | 47 | 1.5 | 36.3 | 4.1 | 0 |
| 300 | 80 | 47 | 7.3 | 91.6 | 8 | 0 |
| 375 | 360 | 186.4 | 5.8 | 100 | 5.8 | 0 |
|  | 160 | 86.9 | 13.1 | 100 | 13.1 | 0 |
|  | 80 | 47 | 17.4 | 100 | 17.4 | 0 |

Example 25 (Comparative)—26 wt % K$_4$P$_2$O$_7$ and 74 wt % Fused Silica Catalyst Dipotassium phosphate (K$_2$HPO$_4$, 100 wt %, 30.00 g; Fluka, St. Louis, Mo., catalog #60347) and amorphous silicon oxide (SiO$_2$, 80.97 g; Aldrich, St. Louis, Mo., catalog #342831) were combined and ground together for 15 min at 500 rpm using a planetary ball mill PM 100 (Retsch, Haan, Germany; catalog #20.540.0003), a 500 mL grinding jar (Retsch, Haan, Germany; catalog #01.462.0227), and 25 grinding balls (Retsch, Haan, Germany, catalog #05.368.0093) to obtain a fine solid. The solid was transferred to a 600 mL glass beaker and calcined at 450° C. for 12 h with a heating ramp of 2° C./min and using a Nabertherm furnace N30/85 HA with P300 controller (Nabertherm, Lilienthal, Germany, catalog # N30/85 HA). After calcination, the material was kept inside the oven until it reached room temperature.

The calcined solid was ground gently using a mortar and pestle to obtain particles of less than about 1 cm, followed by grinding for 30 s at 300 rpm using a planetary ball mill PM 100 (Retsch, Haan, Germany; catalog #20.540.0003), a 125 mL grinding jar (Retsch, Haan, Germany; catalog #01.462.0136), and 3 grinding balls (Retsch, Haan, Germany; catalog #05.368.0028). Then, the solids were sieved for 5 min using a vibratory sieve shaker AS 200 control (Retsch, Haan, Germany; catalog #30.018.0001), and sieves No. 70 and 140 (USA standard testing sieve, ASTM E-11 specifications; Gilson Company, Lewis Center, Ohio). The process of grinding particles retained on sieve No. 70 followed by sieving was repeated until all the material passed sieve No. 70. Finally, the solid retained on sieve No. 140 was re-sieved for 30 min to obtain a catalyst with particle size between 106 m and 212 m (7.9 g). The material was analyzed by XRD and $K_4P_2O_7$ was identified as a component of the dehydration catalyst precursor mixture.

Example 26 (Comparative)

1.2 g of the catalyst prepared in Example 25 were mixed with 1.2 g of fused silica (Sigma-Aldrich Co., St. Louis, Mo.; catalog #: 342831; ground and sieved to 102-212 μm) to form a—13 wt % $K_4P_2O_7$ and 87 wt % fused silica catalyst and tested in the experimental setup of and using the same procedure as in Example 13 (in this Example 26, the OD of the reactor tube was 1.3 cm (½ in.)). The results are shown in Table 9 below.

TABLE 9

Results from testing of the catalyst:
13 wt % $K_4P_2O_7$ and 87 wt % fused silica

| Reaction T, [° C.] | Nitrogen Pressure, [psi] | Water Partial Pressure, [psi] | AAY, [mol %] | LAC, [mol %] | AAS, [mol %] | PAS, [mol %] |
|---|---|---|---|---|---|---|
| 250 | 360 | 186.4 | 1.2 | 14.5 | 8.3 | 0 |
|  | 80 | 47 | 2.8 | 41.1 | 6.8 | 0 |
| 300 | 80 | 47 | 20.9 | 88.3 | 23.7 | 0 |
| 350 | 160 | 86.9 | 28.9 | 92 | 31.4 | 1 |
|  | 80 | 47 | 27.6 | 85.9 | 32.1 | 1.04 |
| 375 | 360 | 186.4 | 30.1 | 100 | 30.1 | 1.32 |
|  | 160 | 86.9 | 35.6 | 94 | 37.9 | 1.36 |

Table 10 below shows selective results from Tables 7, 8, and 9; and Examples 8 and 14 to compare the effect of the molar ratio of K and P in the catalyst $K_xP_yO_z$ on the performance.

TABLE 10

Results from catalysts $K_xP_yO_z$ at 375° C. and various pressures.

| Catalyst; Molar Ratio of K and P | Nitrogen Pressure, [psi] | Water Partial Pressure, [psi] | AAY, [mol %] | LAC, [mol %] | AAS, [mol %] | PAS, [mol %] |
|---|---|---|---|---|---|---|
| Example not according to the present invention | | | | | | |
| $K_2P_4O_{11}$; 0.5 | 360 | 186.4 | 5.8 | 100 | 5.8 | 0 |
|  | 160 | 86.9 | 13.1 | 100 | 13.1 | 0 |
| Examples according to the present invention | | | | | | |
| $(KPO_3)_n$; 1 | 360 | 186.4 | 84.7 | 100 | 84.7 | N/A |
|  | 160 | 86.9 | 85.8 | 100 | 85.8 | N/A |
| $K_5P_3O_{10}$; 1.67 | 360 | 186.4 | 32.5 | 100 | 32.5 | 2.67 |
|  | 160 | 86.9 | 58.6 | 100 | 58.6 | 3.08 |
| Example not according to the present invention | | | | | | |
| $K_4P_2O_7$; 2 | 360 | 186.4 | 30.1 | 100 | 30.1 | 1.32 |
|  | 160 | 86.9 | 35.6 | 94 | 37.9 | 1.36 |

Example 27

2.4 g of the catalyst prepared in Example 8 were tested in the experimental setup of and using the same procedure as in Example 13. In this Example the dehydration zone was 22.9 cm (9 in.) long, the evaporator zone was 30.5 cm (12 in.) long and was packed with 5 g of fused silica ground to 425 to 600 m, the GHSV was 4450 $h^{-1}$, the WHSV was 0.58 $h^{-1}$, and the TOS was about 213 h. At TOS of 21.6 h, the overall acrylic acid yield was 81.7 mol %, lactic acid conversion was 93.3 mol %, acrylic acid selectivity was 87.6 mol %, and propanoic acid selectivity was 0.2 mol %.

Example 28 (Comparative)—26 wt % $(KPO_3)_n$ and 74 wt % Alumina Catalyst

Dipotassium phosphate ($K_2HPO_4$, 100 wt %, 20.00 g, 114.8 mmol; Fluka, St. Louis, Mo., catalog #60347), ammonium phosphate dibasic (($NH_4)_2HPO_4$, 97.7 wt %, 15.52 g, 114.8 mmol; Aldrich, St. Louis, Mo., catalog #379980), and aluminum oxide ($Al_2O_3$, 77.17 g; Alfa, Ward Hill, Mass., catalog #43833) were combined and ground together for 15 min at 500 rpm using a planetary ball mill PM 100 (Retsch, Haan, Germany; catalog #20.540.0003), a 500 mL grinding jar (Retsch, Haan, Germany; catalog #01.462.0227), and 25 grinding balls (Retsch, Haan, Germany, catalog #05.368.0093) to obtain a fine solid. The solid was transferred to a 600 mL glass beaker and calcined at 450° C. for 12 h with a heating ramp of 2° C./min and using a Nabertherm furnace N30/85 HA with P300 controller (Nabertherm, Lilienthal, Germany, catalog # N30/85 HA). After calcination, the material was kept inside the oven until it reached room temperature.

The calcined solid was ground gently using a mortar and pestle to obtain particles of less than about 1 cm, followed by grinding for 30 s at 300 rpm using a planetary ball mill PM 100 (Retsch, Haan, Germany; catalog #20.540.0003), a 125 mL grinding jar (Retsch, Haan, Germany; catalog #01.462.0136), and 3 grinding balls (Retsch, Haan, Germany; catalog #05.368.0028). Then, the solids were sieved for 5 min using a vibratory sieve shaker AS 200 control (Retsch, Haan, Germany; catalog #30.018.0001), and sieves No. 70 and 140 (USA standard testing sieve, ASTM E-11 specifications; Gilson Company, Lewis Center, Ohio). The process of grinding particles retained on sieve No. 70 followed by sieving was repeated until all the material passed sieve No. 70. Finally, the solid retained on sieve No. 140 was re-sieved for 30 min to obtain a catalyst with particle size between 106 μm and 212 μm (34.9 g). The material was analyzed by XRD and $K_3Al_2(PO_4)_3$ and $T\text{-}(KPO_3)_n$, were identified as components of the dehydration catalyst precursor mixture.

Example 29 (Comparative)

3.46 g of the catalyst prepared in Example 28 were tested in the experimental setup of and using the same procedure as in Example 13. In this Example the bottom zone was 6.4 cm (2.5 in.) long, the GHSV was 4422 h$^{-1}$, the WHSV was 0.32 h$^{-1}$, and the TOS was 5.7 h. The overall acrylic acid yield was 11.3 mol %, lactic acid conversion was 53.5 mol %, acrylic acid selectivity was 21.2 mol %, and propanoic acid selectivity was 5.05 mol %.

The foregoing description is given for clearness of understanding only, and no unnecessary limitations should be understood therefrom, as modifications within the scope of the invention may be apparent to those having ordinary skill in the art.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, comprising any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method of preparing a dehydration catalyst, comprising contacting a dehydration catalyst precursor mixture consisting essentially of one or more precursor phosphate salts under conditions including a water partial pressure and a temperature; wherein said one or more precursor phosphate salts consist essentially of one or more monovalent cations, and one or more phosphate anions selected from the group represented by molecular formulae (IV) and (V):

$$[H_2P_yO_{(3y+1)}]^{y-} \qquad (IV)$$

$$[PO_3]^{z-}_z \qquad (V);$$

wherein y is any integer equal to or greater than 1 and z is any integer equal to or greater than 3; wherein said one or more precursor phosphate salts are neutrally charged; with a gas mixture comprising water vapor; wherein the water partial pressure in said gas mixture is equal to or greater than the water partial pressure at the triple point of at least one of said one or more precursor phosphate salts; wherein said contacting step between said dehydration catalyst precursor mixture and said gas mixture is performed at a temperature equal to or greater than the temperature at the triple point of at least one of said one or more precursor phosphate salts; and wherein one or more amorphous phosphate salts are produced as a result of said one or more precursor phosphate salts being contacted with said water vapor.

2. The method of claim 1, wherein said one or more monovalent cations are selected from the group consisting of Na$^+$, K$^+$, Rb$^+$, Cs$^+$, and mixtures thereof.

3. The method of claim 1, wherein said water partial pressure is equal to or greater than about 4 bar; and wherein said contacting step between said one or more precursor phosphate salts and said gas mixture is performed at a temperature equal to or greater than about 250° C.

4. The method of claim 3, wherein the water partial pressure is between about 5 bar and about 35 bar.

5. The method of claim 3, wherein said temperature is between about 300° C. and about 450° C.

6. The method of claim 1, wherein said one or more phosphate anions are selected from the group represented by molecular formulae (IVa), (IVb), (IVc), (IVd), (Va), (Vb), (Vc) and mixtures thereof:

$$[H_2PO_4]^- \qquad (IVa)$$

$$[H_2P_2O_7]^{2-} \qquad (IVb)$$

$$[H_2P_3O_{10}]^{3-} \qquad (IVc)$$

$$[H_2P_4O_{13}]^{4-} \qquad (IVd)$$

$$[P_3O_9]^{3-} \qquad (Va)$$

$$[P_6O_{18}]^{6-} \qquad (Vb)$$

$$[PO_3]^{n-}_n \qquad (Vc);$$

and wherein n is any integer equal to or greater than 3.

7. The method of claim 6, wherein said one or more precursor phosphate salts are selected from the group consisting of $KH_2PO_4$, $(KPO_3)_n$, any of their hydrated forms, and mixtures thereof.

8. The method of claim 1, wherein said contacting step is performed under a total pressure between about 4 bar and about 35 bar.

9. A method of claim 1, wherein said dehydration catalyst precursor mixture further comprises amorphous silicon oxide (SiO$_2$); and wherein said amorphous silicon oxide is substantially chemically inert to said one or more precursor phosphate salts.

10. The method of claim 9, wherein the weight ratio between the total amount of said one or more precursor phosphate salts and the total amount of said silicon oxide in said dehydration catalyst precursor mixture is between about 1:10 and about 4:1.

11. A method of preparing a dehydration catalyst, comprising under conditions including a water partial pressure and a temperature, a dehydration catalyst precursor mixture consisting essentially of one or more precursor phosphate salts and one or more oxysalts; wherein said one or more oxysalts are substantially chemically inert to said one or more precursor phosphate salts; wherein said one or more precursor phosphate salts consist essentially of one or more monovalent cations, and one or more phosphate anions selected from the group represented by molecular formulae (IV) and (V):

$$[H_2P_yO_{(3y+1)}]^{y-} \quad (IV)$$

$$[PO_3]_z^{z-} \quad (V);$$

wherein y is any integer equal to or greater than 1 and z is any integer equal to or greater than 3; wherein said one or more precursor phosphate salts are neutrally charged; wherein said one or more oxysalts comprise one or more polyvalent cations, and one or more oxyanions selected from the group represented by molecular formulae (II) and (III):

$$[H_{(a-2b)}S_cO_{(4c-b)}]^{(2c-a)-} \quad (II)$$

$$[Ta_{2d}O_{(5d+e)}]^{2e-} \quad (III);$$

wherein a and b are positive integers or zero; wherein c, d, and e are positive integers; wherein (a−2b) is equal to or greater than zero; wherein (2c−a) is greater than zero; wherein said one or more oxysalts are neutrally charged; with a gas mixture comprising water vapor; wherein the water partial pressure in said gas mixture is equal to or greater than the water partial pressure at the triple point of at least one of said one or more precursor phosphate salts; wherein said contacting step between said dehydration catalyst precursor mixture and said gas mixture is performed at a temperature equal to or greater than the temperature at the triple point of at least one of said one or more precursor phosphate salts; and wherein one or more amorphous phosphate salts are produced as a result of said one or more precursor phosphate salts being contacted with said water vapor.

12. The method of claim 11, wherein said dehydration catalyst precursor mixture further comprises amorphous silicon oxide (SiO2); and wherein said amorphous silicon oxide is substantially chemically inert to said one or more precursor phosphate salts.

* * * * *